US012767641B2

(12) United States Patent
Heo et al.

(10) Patent No.: US 12,767,641 B2
(45) Date of Patent: Oct. 20, 2026

(54) COMPOUND AND ORGANIC LIGHT EMITTING DEVICE COMPRISING THE SAME

(71) Applicant: LG CHEM, LTD., Seoul (KR)

(72) Inventors: Dong Uk Heo, Daejeon (KR); Heekyung Yun, Daejeon (KR); Miyeon Han, Daejeon (KR); Jae Tak Lee, Daejeon (KR); Jung Min Yoon, Daejeon (KR); Hoyoon Park, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 791 days.

(21) Appl. No.: 18/265,294

(22) PCT Filed: Feb. 28, 2022

(86) PCT No.: PCT/KR2022/095044

§ 371 (c)(1),
(2) Date: Jun. 5, 2023

(87) PCT Pub. No.: WO2022/191681

PCT Pub. Date: Sep. 15, 2022

(65) Prior Publication Data

US 2024/0138255 A1 Apr. 25, 2024

(30) Foreign Application Priority Data

Mar. 8, 2021 (KR) ........................ 10-2021-0030417

(51) Int. Cl.
*H10K 85/60* (2023.01)
*C07D 237/08* (2006.01)
(Continued)

(52) U.S. Cl.
CPC ......... *C07D 251/24* (2013.01); *C07D 237/08* (2013.01); *C07D 239/26* (2013.01);
(Continued)

(58) Field of Classification Search
CPC .... H10K 50/16; H10K 50/171; H10K 85/626; H10K 85/654; H10K 85/655; H10K 85/656
See application file for complete search history.

(56) References Cited

U.S. PATENT DOCUMENTS 6,821,643 B1 11/2004 Hu et al.
10,636,990 B2 * 4/2020 Kroeber .................. C09B 57/00
(Continued)

FOREIGN PATENT DOCUMENTS

CN 106554771 A 4/2017
CN 106565434 A 4/2017
(Continued)

OTHER PUBLICATIONS

Mboyi et al., "Bridge-Clamp Bis(tetrazine)s with [N]; TT-Stacking Interactions and Azido-s-Aryl Tetrazines: Two Classes of Doubly Clickable Tetrazines," Angewandte Chemie International Edition, 59:1149-1154 (2020).

(Continued)

*Primary Examiner* — Golam Mowla
(74) *Attorney, Agent, or Firm* — Bryan Cave Leighton Paisner LLP

(57) ABSTRACT

Provided is a compound of Chemical Formula 1 or 2:

[Chemical Formula 1]

(Continued)

-continued

[Chemical Formula 2]

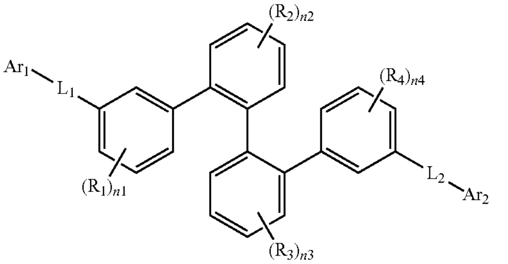

wherein: $R_1$ to $R_4$ are each independently hydrogen or deuterium; n1 to n4 are an integer of 1 to 4; $L_1$ and $L_2$ are each independently a direct bond or a substituted or unsubstituted $C_{6-60}$ arylene; and $Ar_1$ and $Ar_2$ are each independently a substituent of Chemical Formula 3:

[Chemical Formula 3]

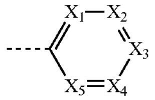

wherein $X_1$ to $X_5$ are each independently N or $C(R_5)$, wherein at least two of $X_1$ to $X_5$ are N; and each $R_5$ is independently hydrogen, deuterium, a substituted or unsubstituted $C_{1-20}$ alkyl, a substituted or unsubstituted $C_{6-60}$ aryl, or a substituted or unsubstituted $C_{2-60}$ heteroaryl containing at least one of N, O and S, or two adjacent $R_5$s combine to form a benzene ring; and an organic light emitting device including the same. The device exhibits significantly superior efficiency and lifespan.

10 Claims, 2 Drawing Sheets

(51) Int. Cl.

| | |
|---|---|
| ***C07D 239/26*** | (2006.01) |
| ***C07D 239/74*** | (2006.01) |
| ***C07D 251/24*** | (2006.01) |
| ***H10K 50/16*** | (2023.01) |
| ***H10K 50/17*** | (2023.01) |

(52) U.S. Cl.

CPC ......... *C07D 239/74* (2013.01); *H10K 85/654* (2023.02); *H10K 50/16* (2023.02); *H10K 50/171* (2023.02)

(56) References Cited

U.S. PATENT DOCUMENTS

2003/0163003 A1 8/2003 Zhang et al.
2004/0251816 A1 12/2004 Leo et al.
2007/0196692 A1 8/2007 Ise et al.
2008/0297037 A1 12/2008 Vestweber et al.
2009/0146554 A1 6/2009 Lee et al.
2012/0104941 A1 5/2012 Jung et al.
2015/0255730 A1 9/2015 Chuang et al.
2017/0098778 A1 4/2017 Oh et al.
2018/0114917 A1 4/2018 Lee et al.
2018/0301635 A1 10/2018 Lee et al.
2019/0181351 A1 6/2019 Jang et al.
2019/0312223 A1 10/2019 Chun et al.
2020/0039903 A1 2/2020 Stoessel et al.
2020/0083463 A1 3/2020 Stoessel et al.
2020/0194706 A1 6/2020 Han et al.
2020/0227650 A1 7/2020 Kim et al.
2021/0198215 A1 7/2021 Galan et al.
2022/0173335 A1 6/2022 Itoi et al.
2023/0354701 A1 11/2023 Stoessel et al.

FOREIGN PATENT DOCUMENTS

CN 111116562 A 5/2020
EP 3674299 A1 7/2020
JP H09-188874 7/1997
JP 2008-195841 8/2008
JP 2009-170818 7/2009
JP 2012-126718 7/2012
JP 2013-115066 6/2013
JP 2018-524276 A 8/2018
JP 2020515602 A 5/2020
KR 10-2000-0051826 8/2000
KR 10-2009-0059842 6/2009
KR 10-2014-0094408 7/2014
KR 10-2017-0045558 4/2017
KR 10-2017-0048159 5/2017
KR 10-2017-0067424 A 6/2017
KR 10-2017-0111802 10/2017
KR 10-1884130 B1 7/2018
KR 10-2019-0024640 3/2019
KR 10-2019-0134675 12/2019
KR 10-2020-0113078 10/2020
KR 10-2021-0009912 1/2021
WO 2001-014299 3/2001
WO 2003-012890 A2 2/2003
WO 2007-065678 6/2007
WO 2011-005060 A2 1/2011
WO 2017-069442 4/2017
WO 2018-021663 2/2018
WO 2018087346 A1 5/2018
WO 2018-182145 10/2018
WO 2019-004584 1/2019
WO 2019-061796 4/2019
WO 2019-238858 12/2019
WO 2020-012685 A1 1/2020
WO 2020-209307 10/2020

OTHER PUBLICATIONS

Zhu et al., "Ruthenium-Catalyzed Reductive Cleavage of Unstrained Aryl-Aryl Bonds: Reaction Development and Mechanistic Study," Journal of The American Chemical Society, 141(46):18630-18640 (2019).
Chen et al., "High-spin enforcement in first-row metal complexes of a constrained polyaromatic ligand: synthesis, structure, and properties," New Journal of Chemistry, 42:18667-18677 (2018).
Sham et al., "Coordination properties of axially unfixed chiral dipyridine ligands towards metal and ammonium ions," Polyhedron, 30(6):1149-1156 (2011).

* cited by examiner

【FIG. 1】
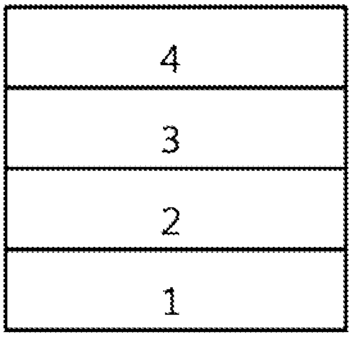
【FIG. 2】
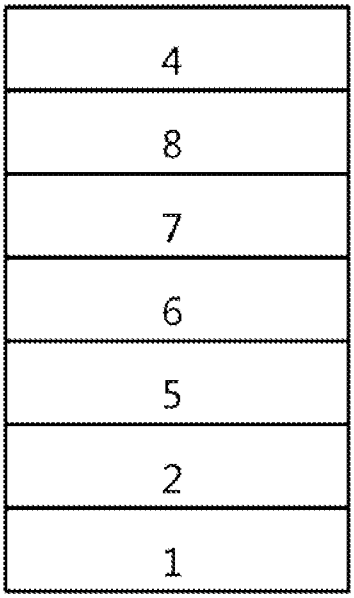

【FIG. 3】
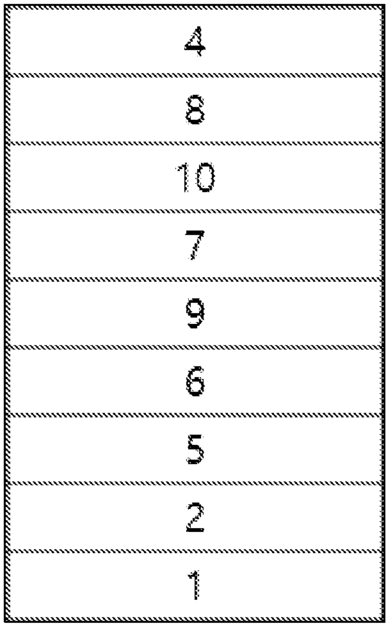

COMPOUND AND ORGANIC LIGHT EMITTING DEVICE COMPRISING THE SAME

CROSS-REFERENCE TO RELATED APPLICATION(s)

This application is a National Stage Application of International Application No. PCT/KR2022/095044 filed on Feb. 28, 2022, which claims priority to and the benefit of Korean Patent Application No. 10-2021-0030417 filed on Mar. 8, 2021 in the Korean Intellectual Property Office, the disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2000-0051826

(Patent Literature 0002) US Patent Publication No. 2007-0196692

(Patent Literature 0003) Korean Unexamined Patent Publication No. 10-2017-0048159

(Patent Literature 0004) U.S. Pat. No. 6,821,643

BRIEF DESCRIPTION

Technical Problem

The present disclosure relates to a novel compound and an organic light emitting device including the same.

Technical Solution

In the present disclosure, provided is a compound of Chemical Formula 1 or 2:

[Chemical Formula 1]

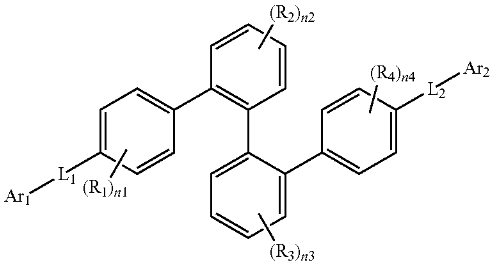

[Chemical Formula 2]

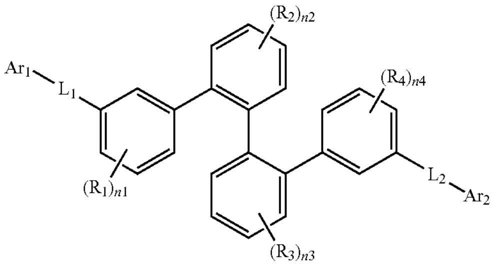

wherein in Chemical Formula 1 or 2:

$R_1$ to $R_4$ are each independently hydrogen or deuterium;

n1 to n4 are an integer of 1 to 4;

$L_1$ and $L_2$ are each independently a direct bond or a substituted or unsubstituted $C_{6-60}$ arylene; and $Ar_1$ and $Ar_2$ are each independently a substituent of Chemical Formula 3:

[Chemical Formula 3]

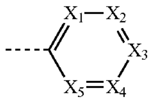

wherein in Chemical Formula 3:

$X_1$ to $X_5$ are each independently N or $C(R_5)$, wherein at least two of $X_1$ to $X_5$ are N; and each $R_5$ is independently hydrogen, deuterium, a substituted or unsubstituted $C_{1-20}$ alkyl, a substituted or unsubstituted $C_{6-60}$ aryl, or a substituted or unsubstituted $C_{2-60}$ heteroaryl containing at least one heteroatom selected from the group consisting of N, O and S, or two adjacent $R_5$s are combined to form a benzene ring.

In addition, provided is an organic light emitting device including: a first electrode; a second electrode that is opposite to the first electrode; and one or more organic material layers that are between the first electrode and the second electrode, wherein at least one layer of the one or more organic material layers includes at least one of the compound of Chemical Formula 1 and the compound of Chemical Formula 2.

Advantageous Effects

The compound of Chemical Formula 1 or Chemical Formula 2 can be used as a material for an organic material layer of an organic light emitting device, and can improve efficiency, low driving voltage, and/or lifespan of the organic light emitting device. In particular, the compound of Chemical Formula 1 can be used as a material for hole injection, hole transport, hole injection and transport, light emission, electron transport, or electron injection.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport and injection layer 8, and a cathode 4.

FIG. 3 shows an example of an organic light emitting device including a substrate 1, an anode 2, a hole injection layer 5, a hole transport layer 6, an electron blocking layer 9, a light emitting layer 7, a hole blocking layer 10, an electron transport and injection layer 8, and a cathode 4.

DETAILED DESCRIPTION

Hereinafter, embodiments of the present disclosure will be described in more detail to facilitate understanding of the invention.

As used herein, the notation

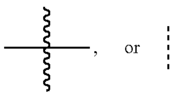

means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent in which two or more substituents of the above-exemplified substituents are connected. For example, "a substituent in which two or more substituents are connected" can be a biphenyl group. Namely, a biphenyl group can be an aryl group, or it can also be interpreted as a substituent in which two phenyl groups are connected.

In the present disclosure, the carbon number of a carbonyl group is not particularly limited, but is preferably 1 to 40. Specifically, the carbonyl group can be a compound having the following structural formulae, but is not limited thereto:

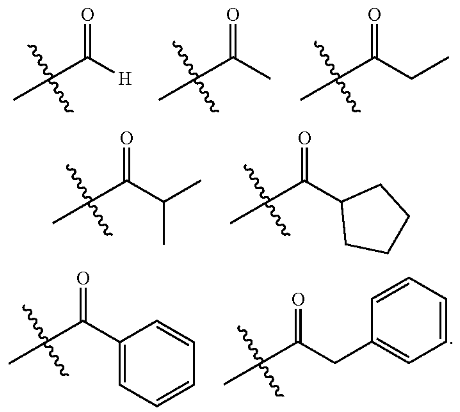

In the present disclosure, an ester group can have a structure in which oxygen of the ester group is substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

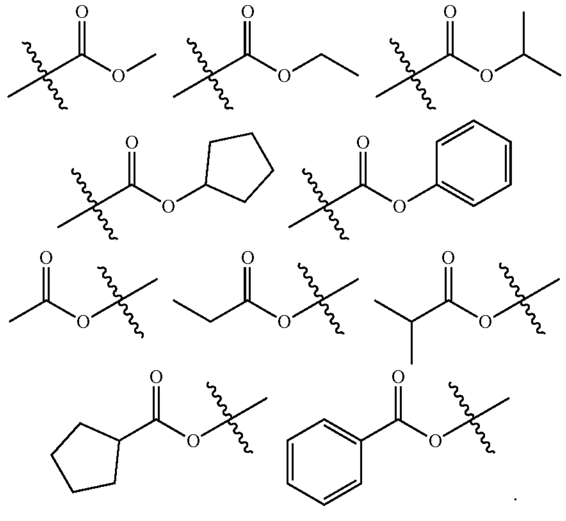

In the present disclosure, the carbon number of an imide group is not particularly limited, but is preferably 1 to 25. Specifically, the imide group can be a compound having the following structural formulae, but is not limited thereto:

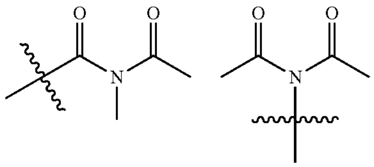

-continued

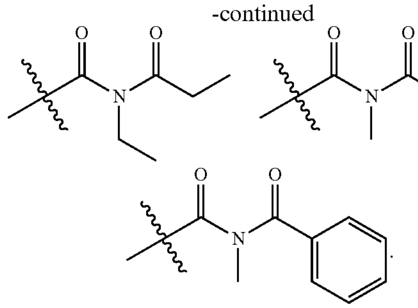

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, a phenylboron group, and the like, but is not limited thereto.

In the present disclosure, examples of a halogen group include fluorine, chlorine, bromine, or iodine.

In the present disclosure, the alkyl group can be straight-chain, or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The monocyclic aryl group includes a phenyl group, a biphenyl group, a terphenyl group and the like, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present disclosure, a fluorenyl group can be substituted, and two substituents can be bonded to each other to form a spiro structure. In the case where the fluorenyl group is substituted,

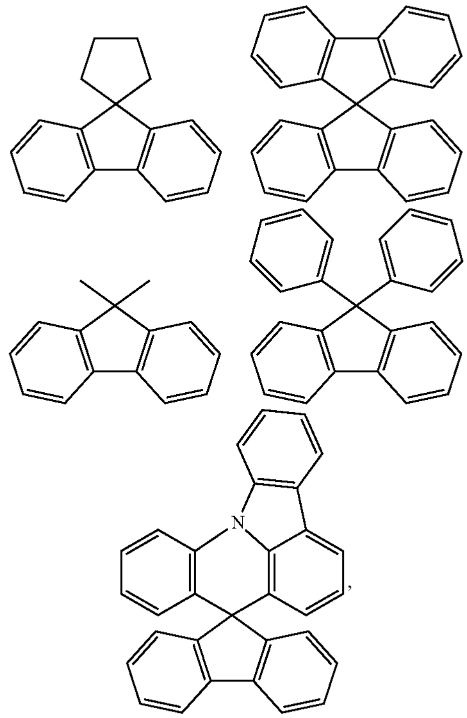

and the like can be formed. However, the structure is not limited thereto.

In the present disclosure, a heterocyclic group is a heterocyclic group containing at least one heteroatom of O, N, Si and S as a heterogeneous element, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can apply the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocycle is not a monovalent group but formed by combining two substituent groups.

(Compound)

In the present disclosure, provided is a compound of Chemical Formula 1 or 2.

Preferably, Chemical Formula 1 can be the following Chemical Formula 1-1, and Chemical Formula 2 can be the following Chemical Formula 2-1:

[Chemical Formula 1-1]

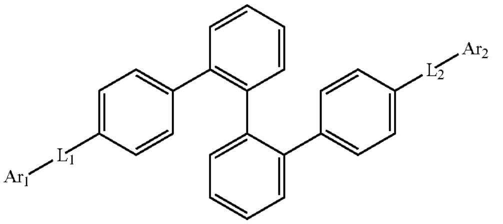

[Chemical Formula 2-1]

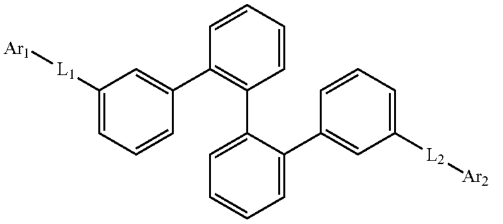

wherein in the Chemical Formula 1-1 or 2-1:

$L_1$, $L_2$, $Ar_1$ and $Ar_2$ are as defined above.

Preferably, $L_1$ and $L_2$ are each independently a direct bond, phenylene, or biphenyldiyl.

Preferably, $Ar_1$ and $Ar_2$ are each independently any one selected from the group consisting of:

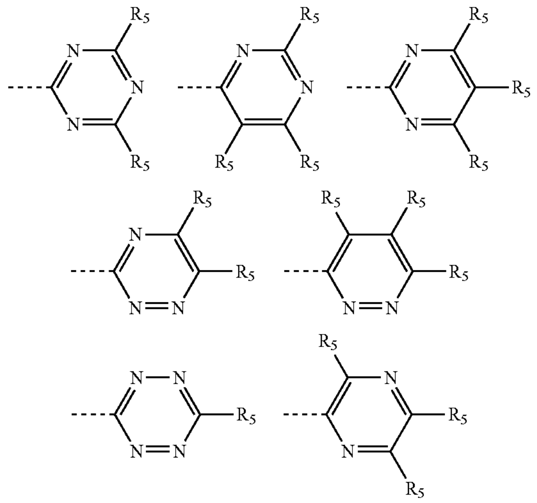

wherein in the above group:

$R_5$ is as defined above.

Preferably, each $R_5$ is independently hydrogen, deuterium, methyl, tert-butyl, phenyl, biphenylyl, terphenylyl, naphthyl, pyridinyl, furanyl, or thiophenyl, or two adjacent $R_5$s are combined to form a benzene ring; and the phenyl, biphenylyl, terphenylyl, naphthyl, pyridinyl, furanyl, or thiophenyl is each independently unsubstituted or substituted with deuterium, methyl, or tert-butyl.

Preferably, $Ar_1$ and $Ar_2$ are each independently any one selected from the group consisting of:

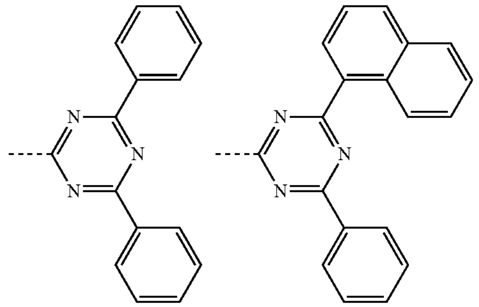

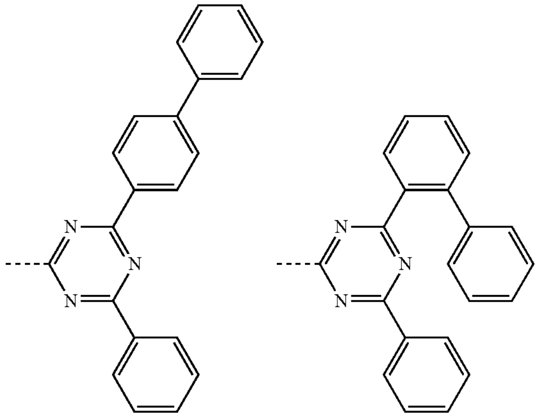

-continued
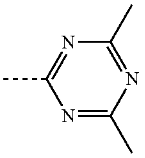
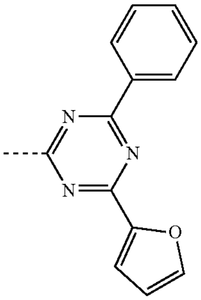
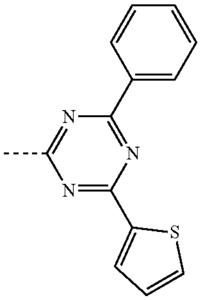
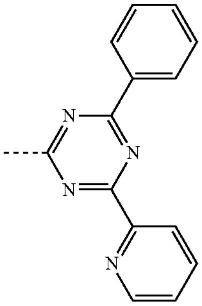
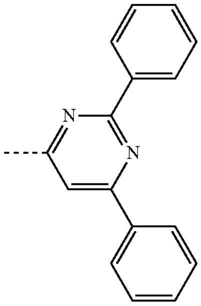
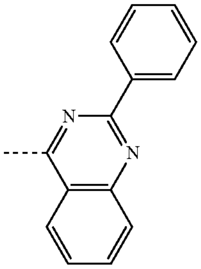
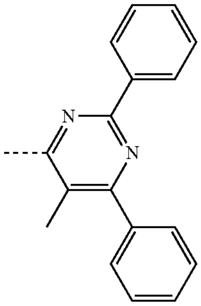
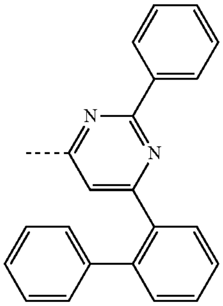
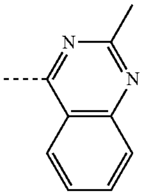
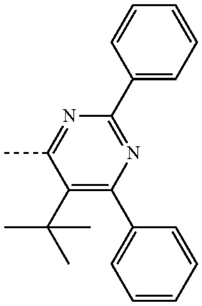
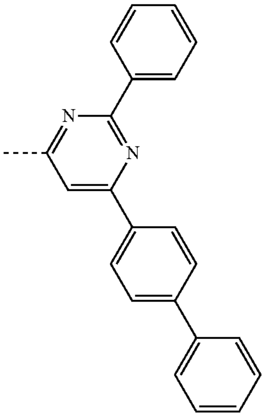
-continued
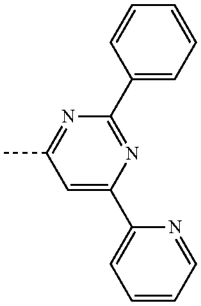
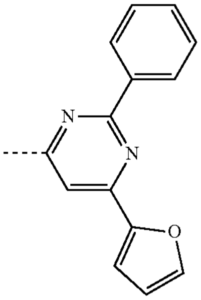
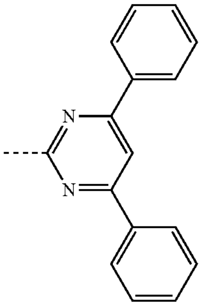
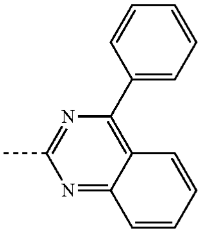
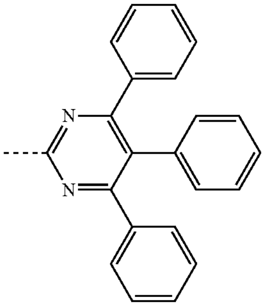
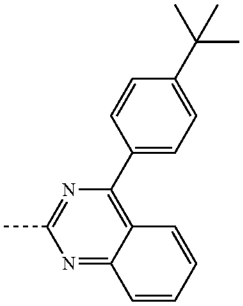
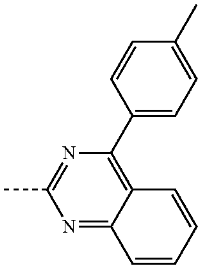
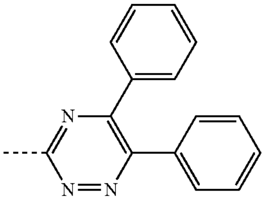
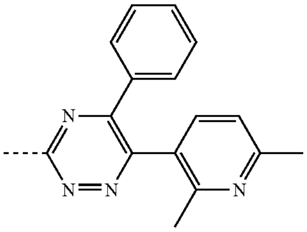
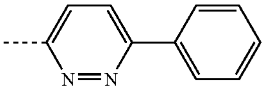
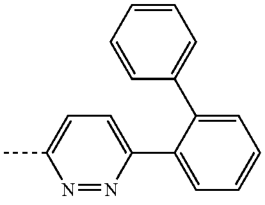
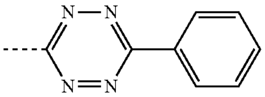

-continued
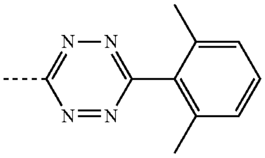
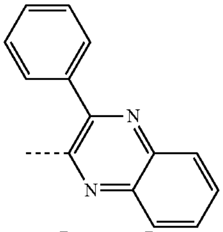
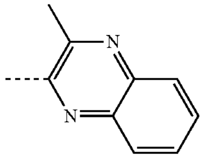
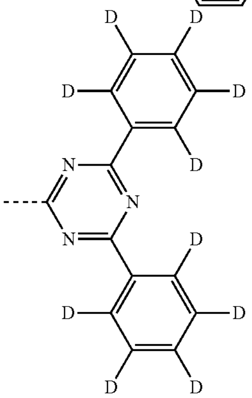
-continued
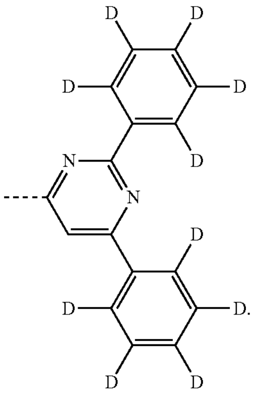
Representative examples of the compound of Chemical Formula 1 or 2 are as follows:
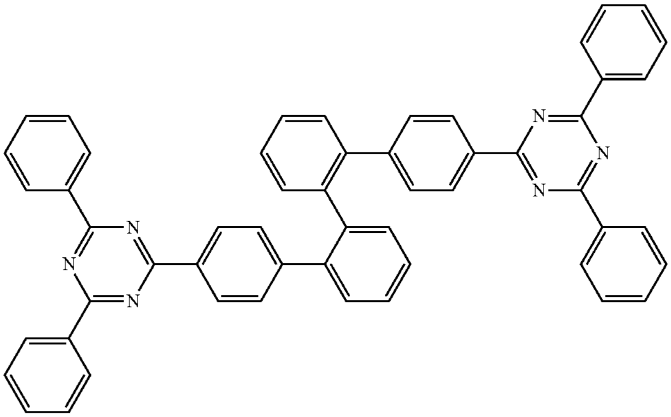
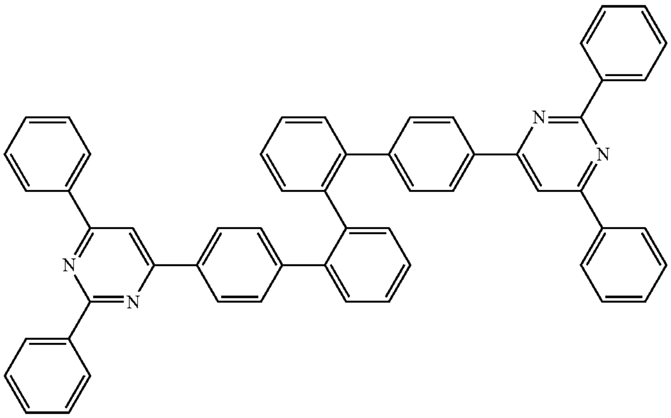

-continued
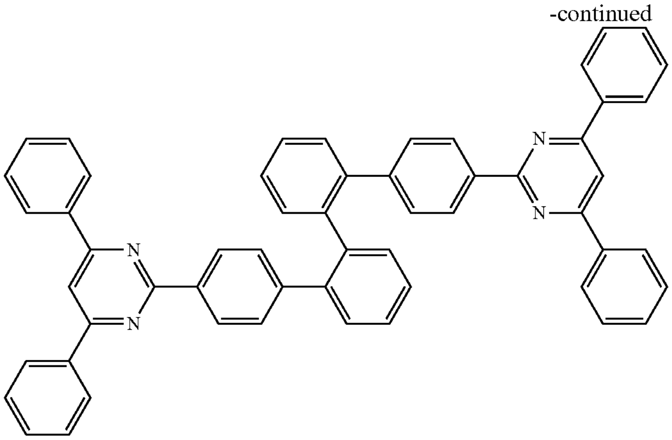
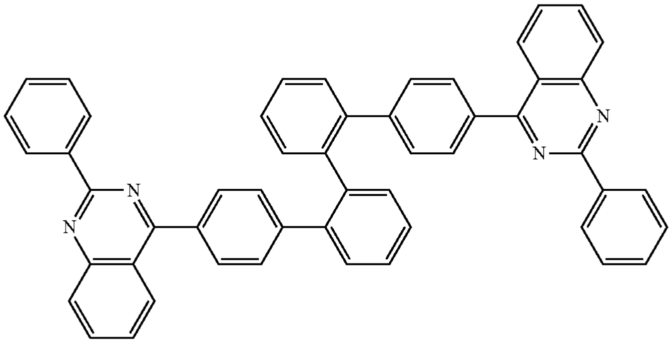
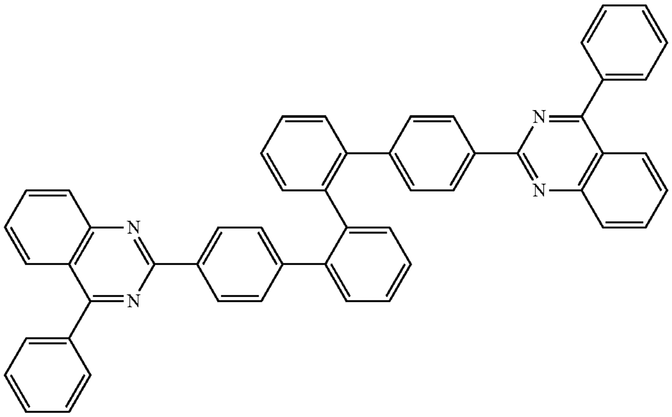
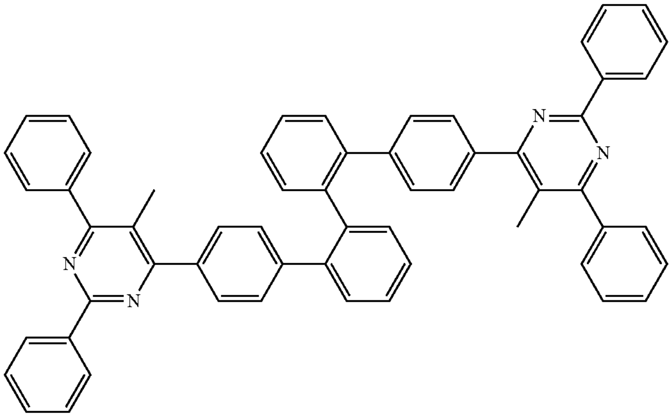

-continued
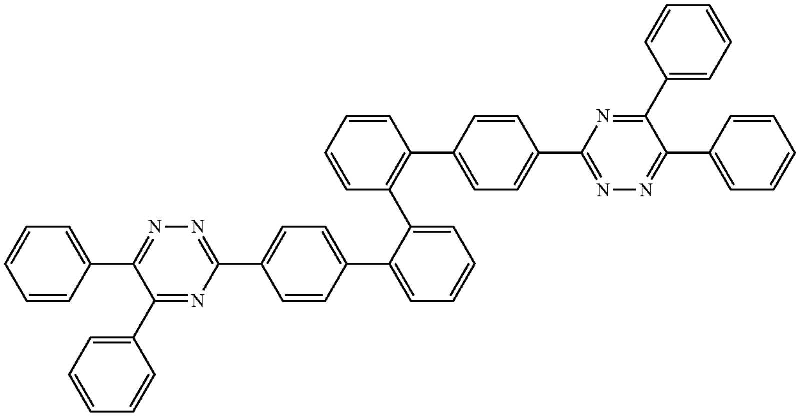
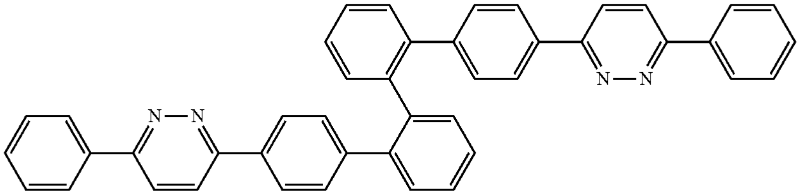
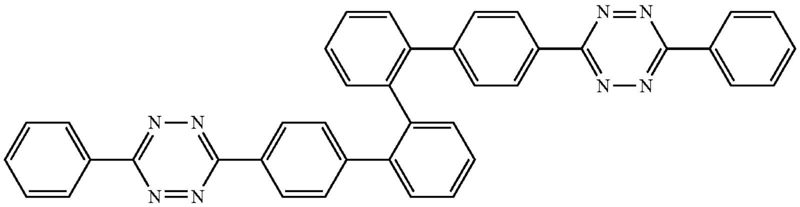
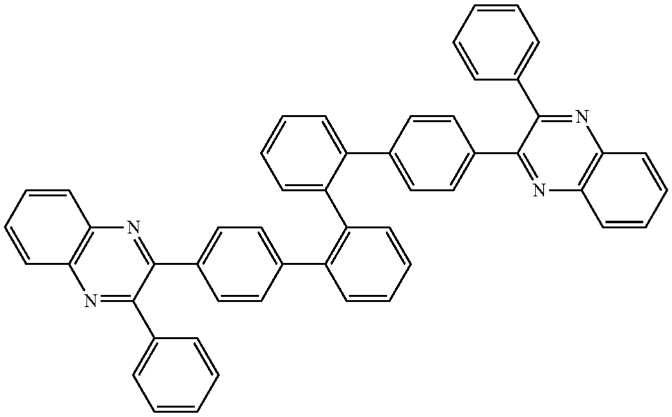
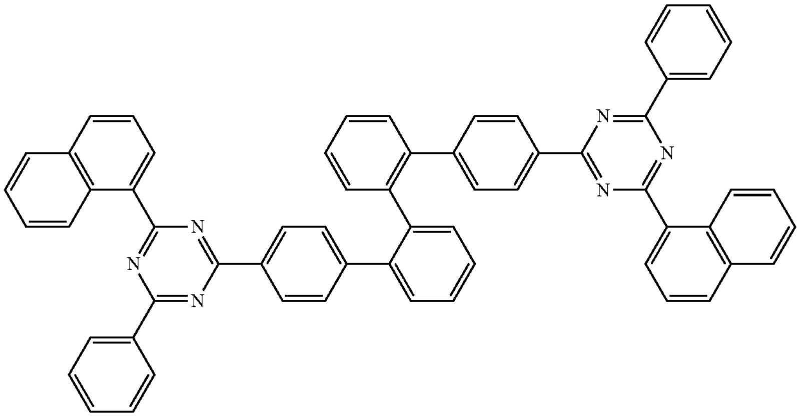

-continued
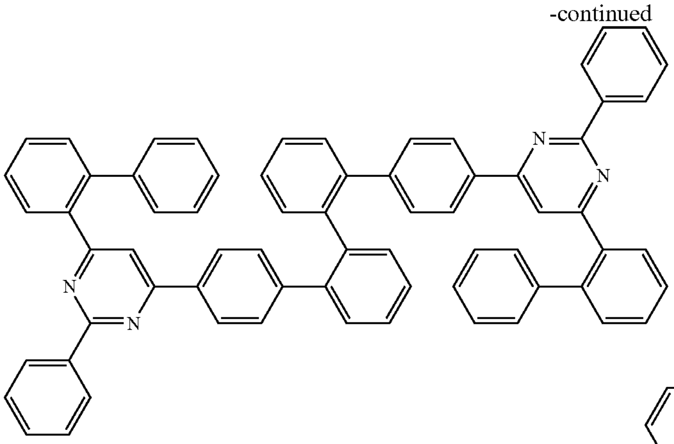
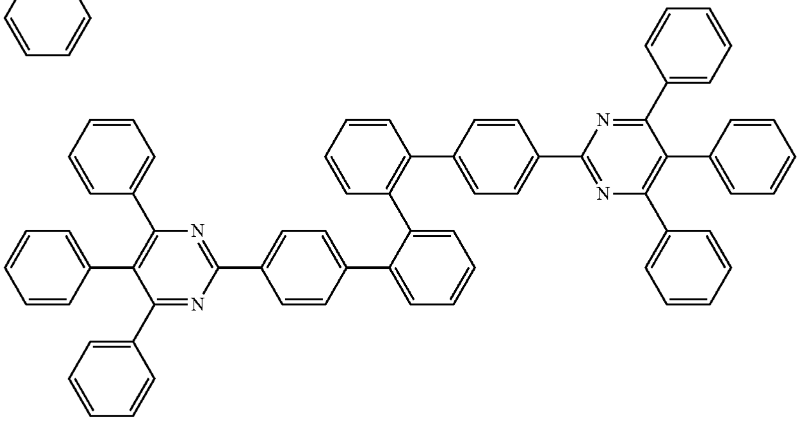
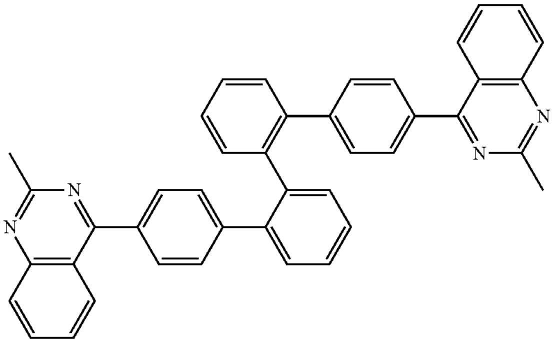
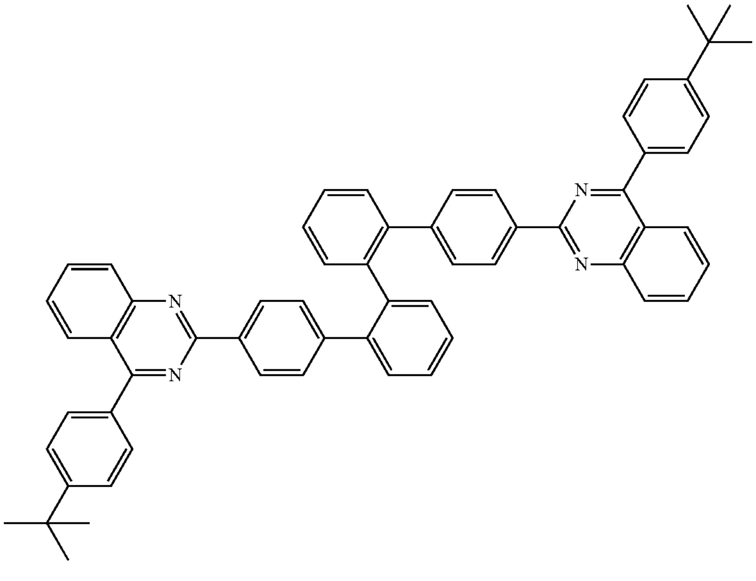

-continued
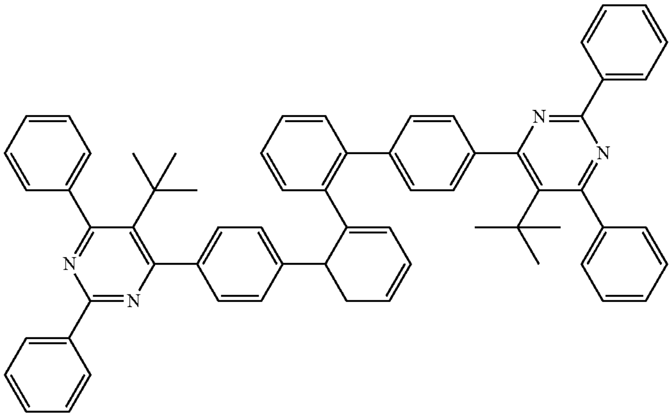
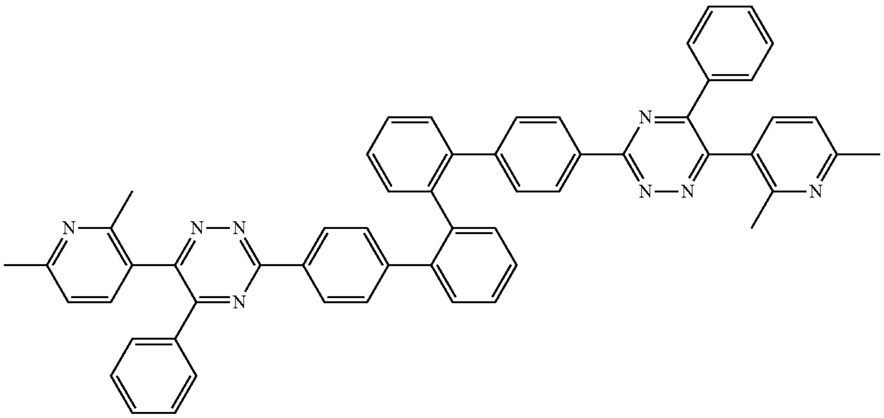
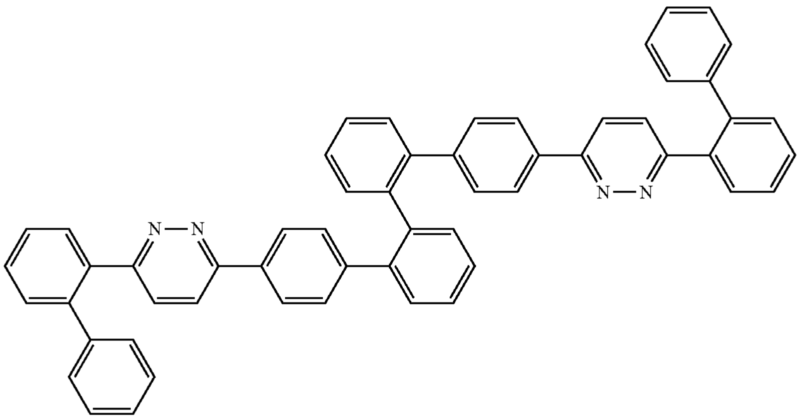
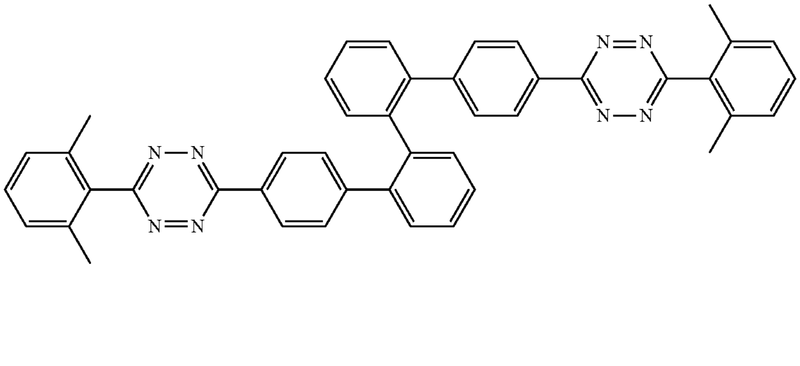

-continued
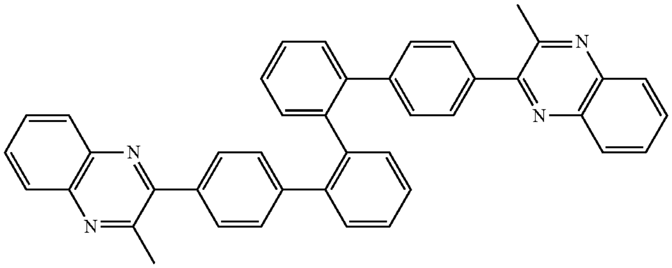
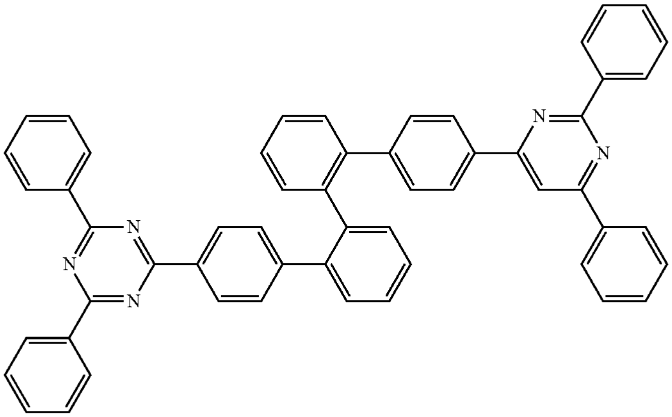
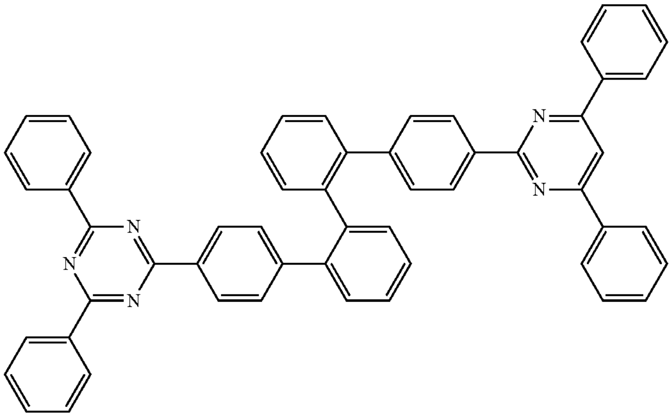
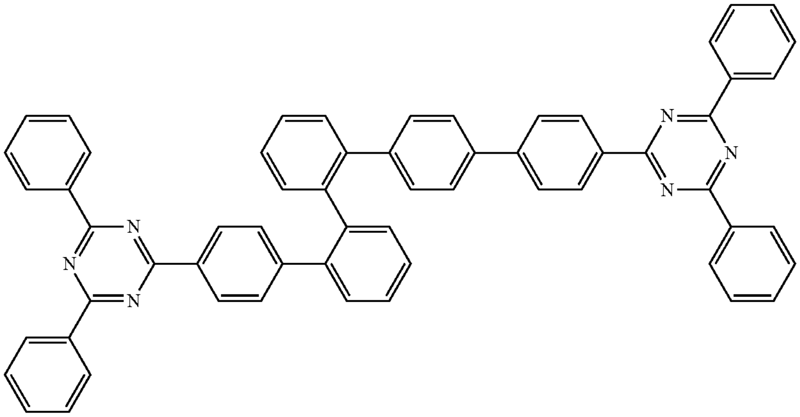

-continued
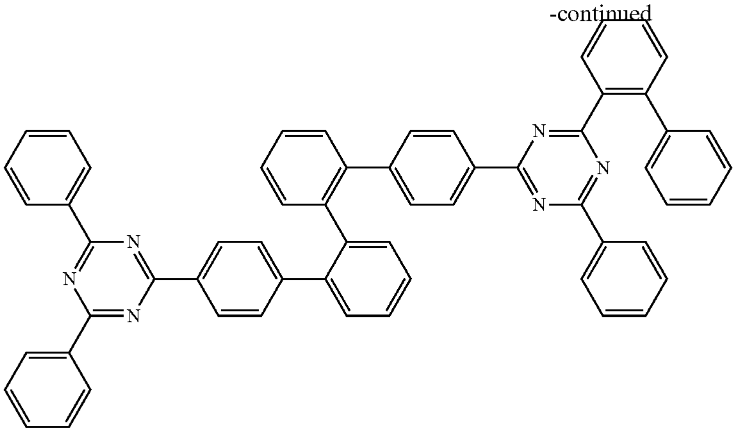
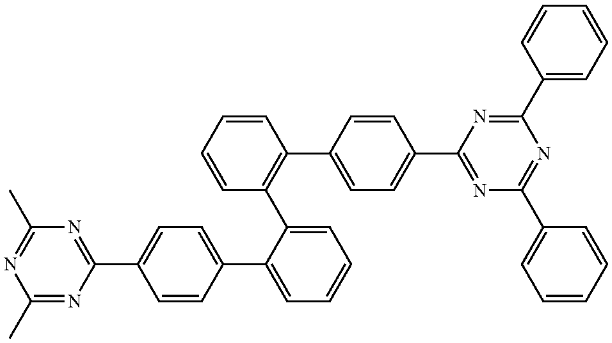
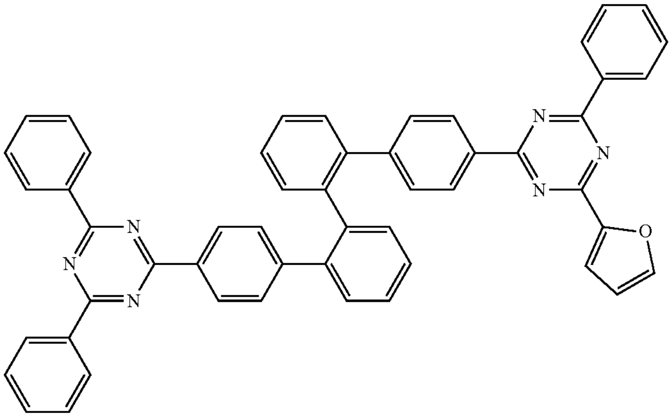
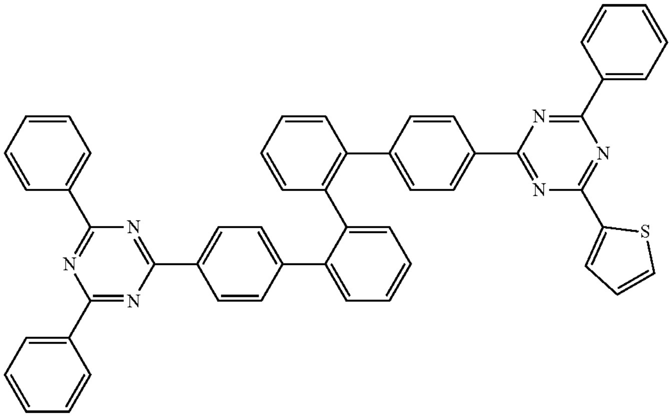

-continued
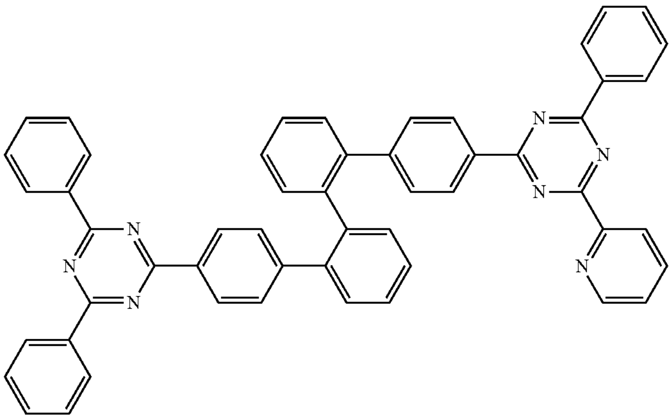
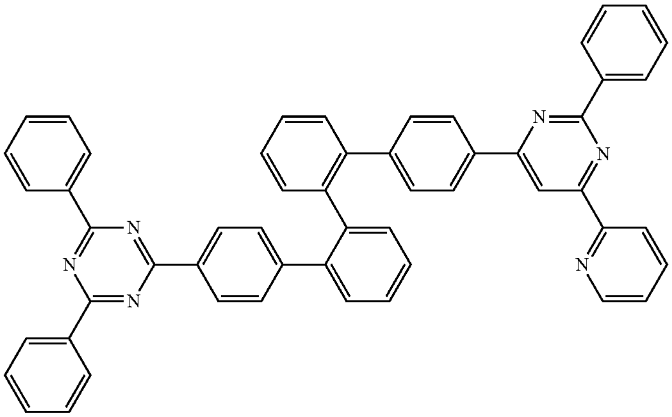
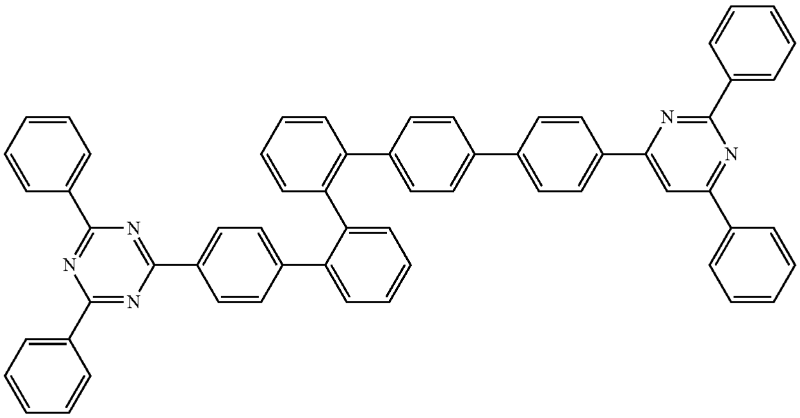
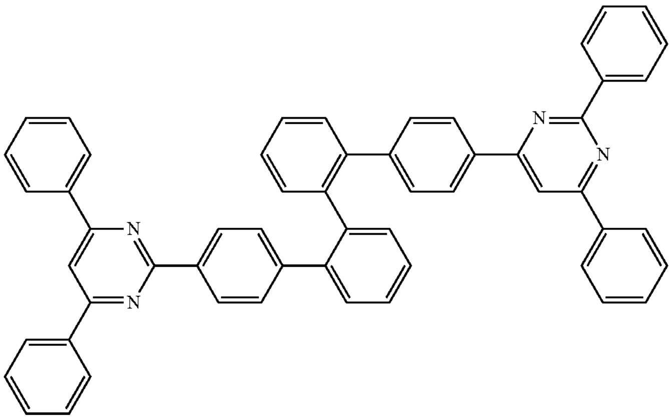

-continued
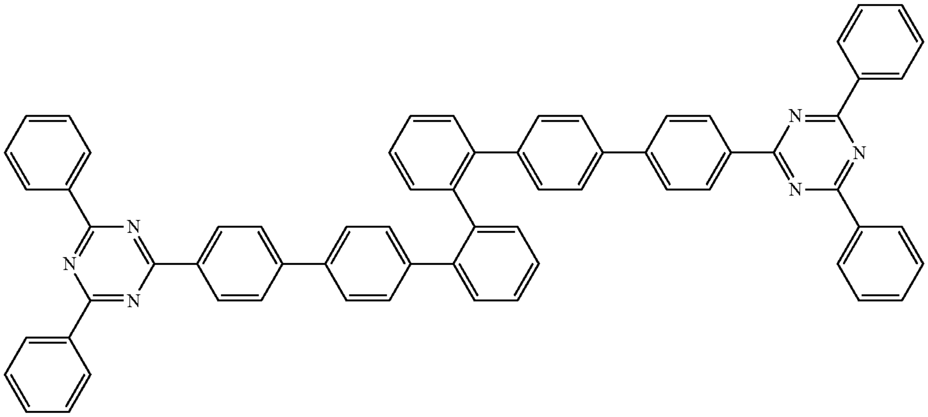
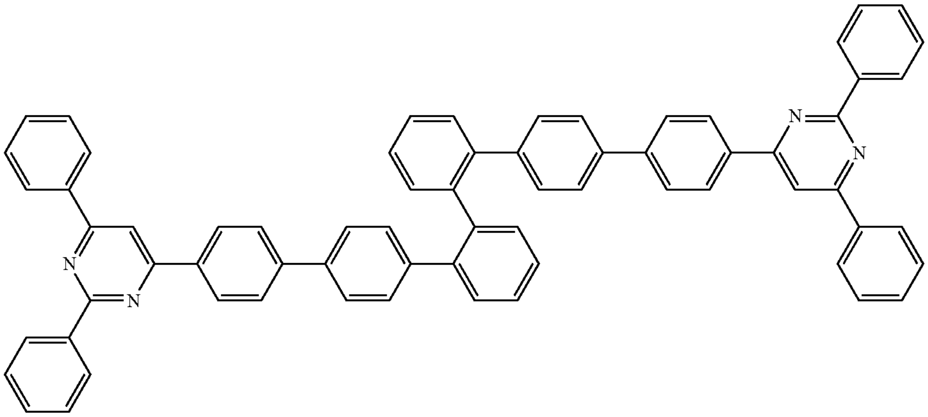
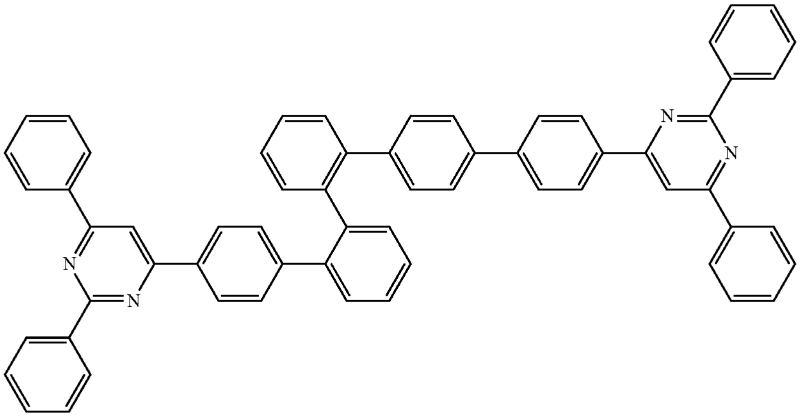
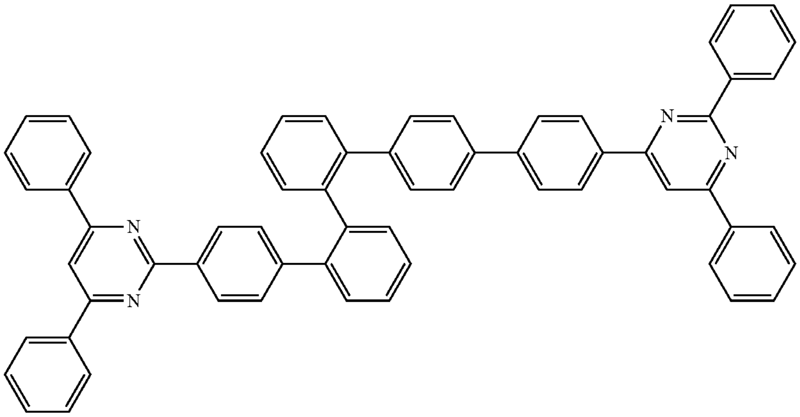

-continued
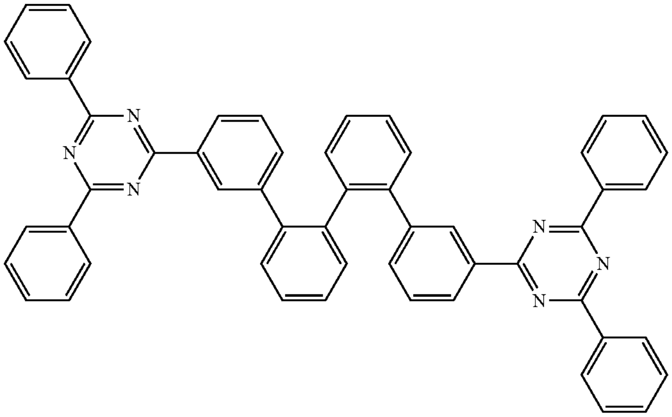
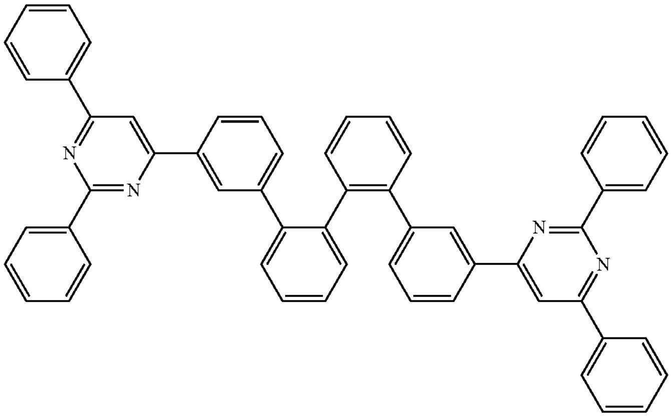
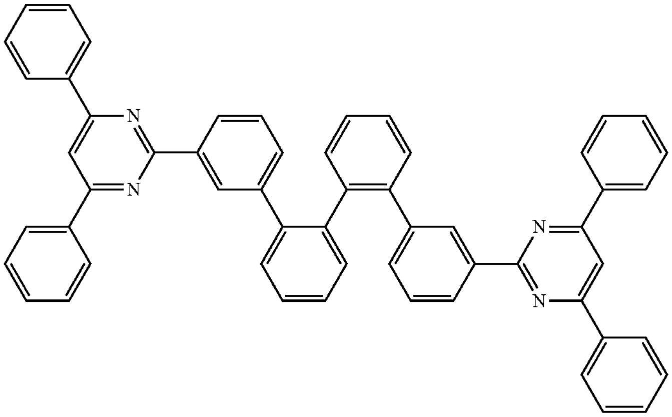
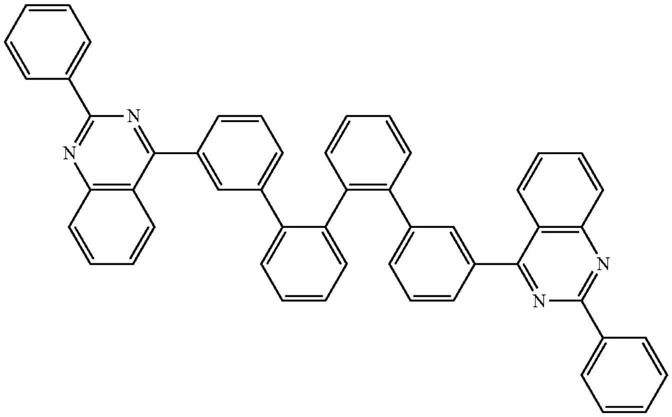

-continued
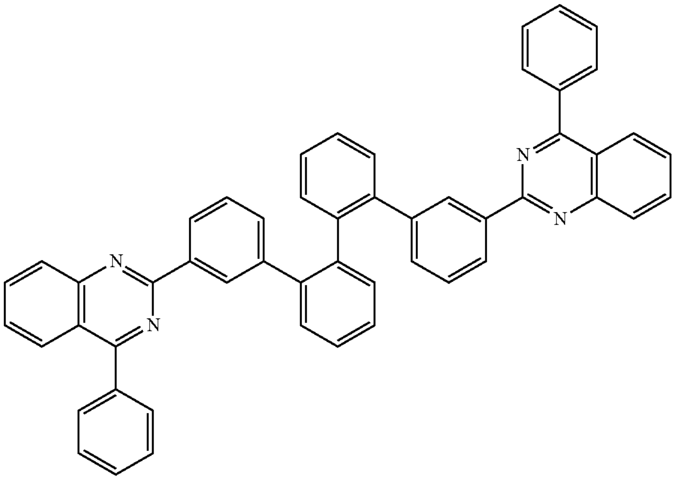
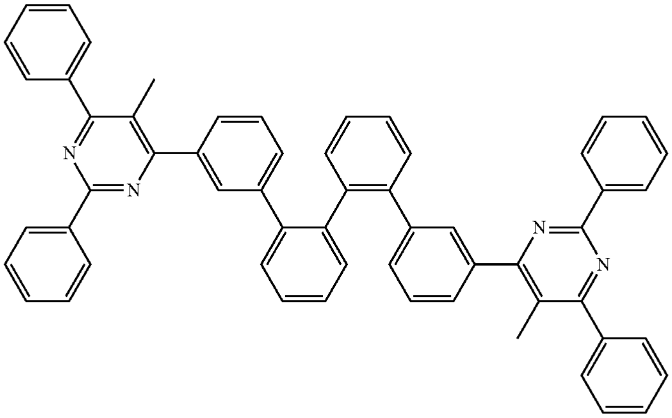
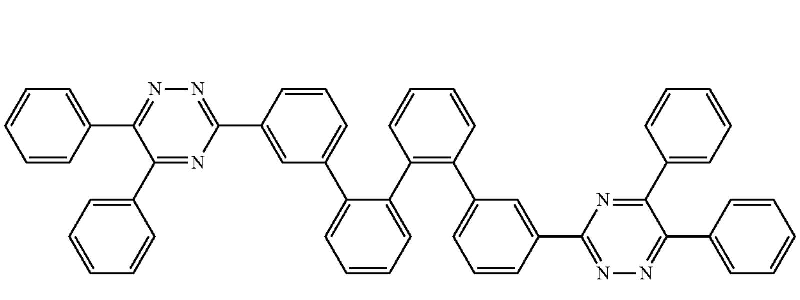

-continued
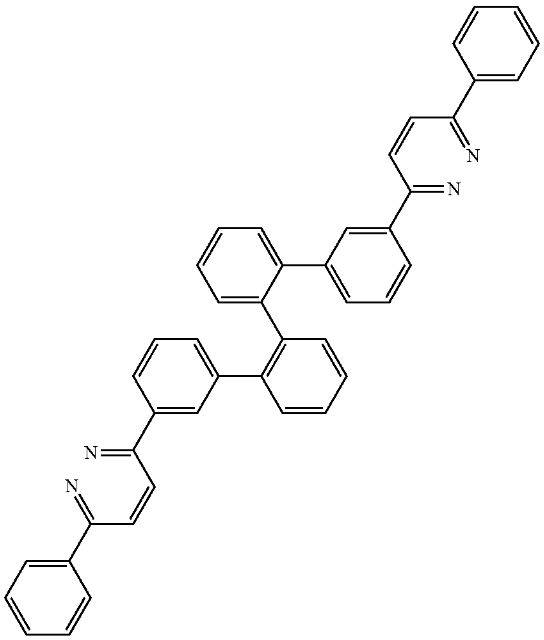
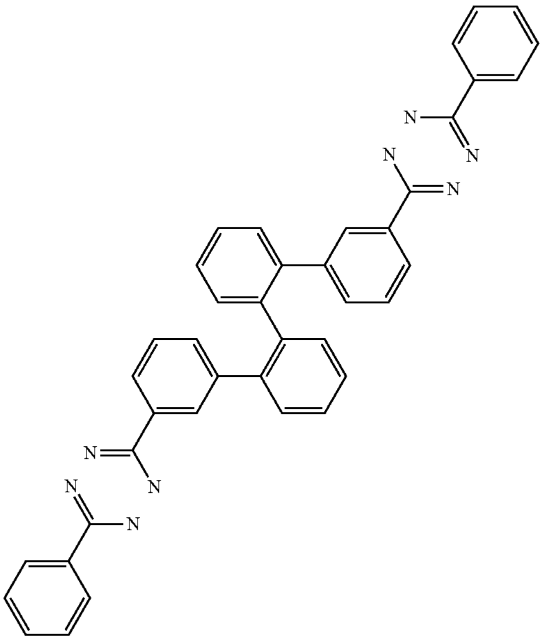
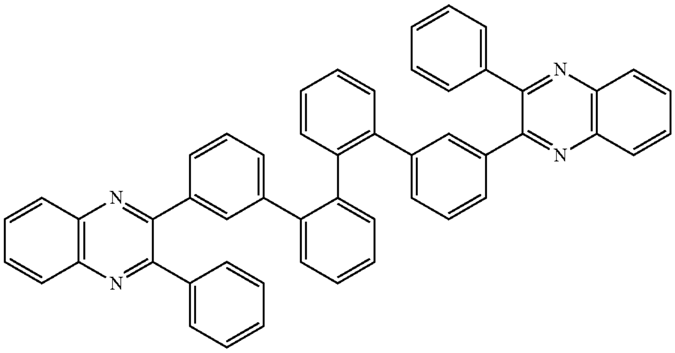
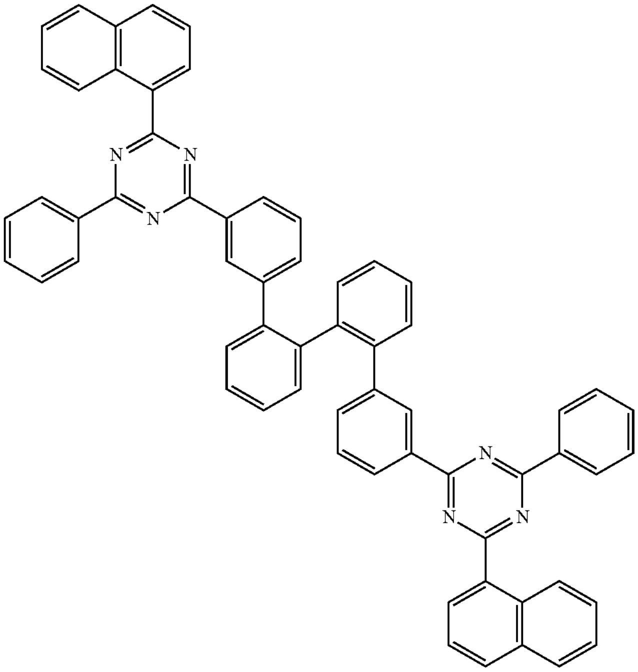

-continued
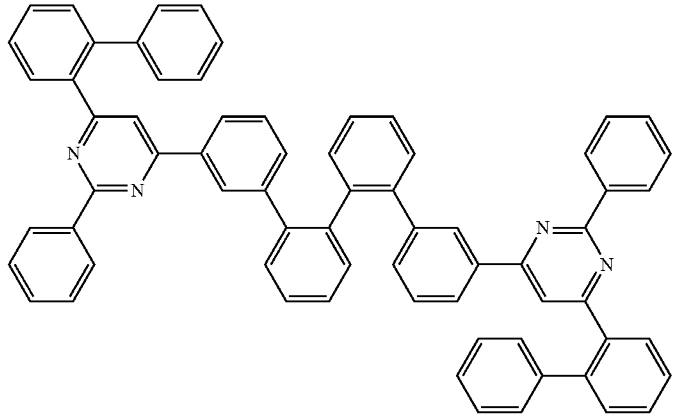
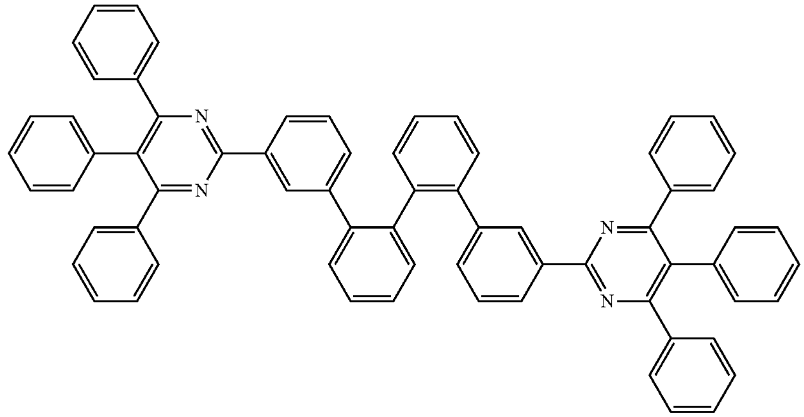
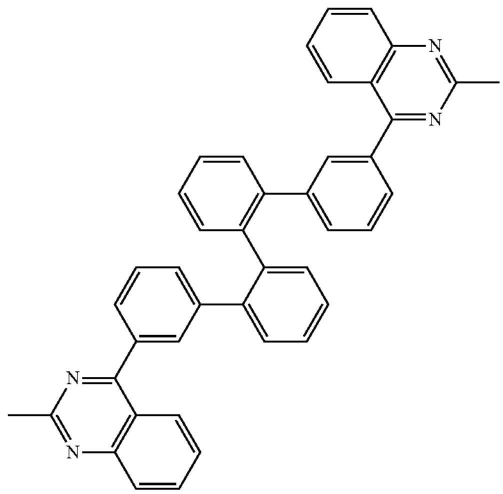
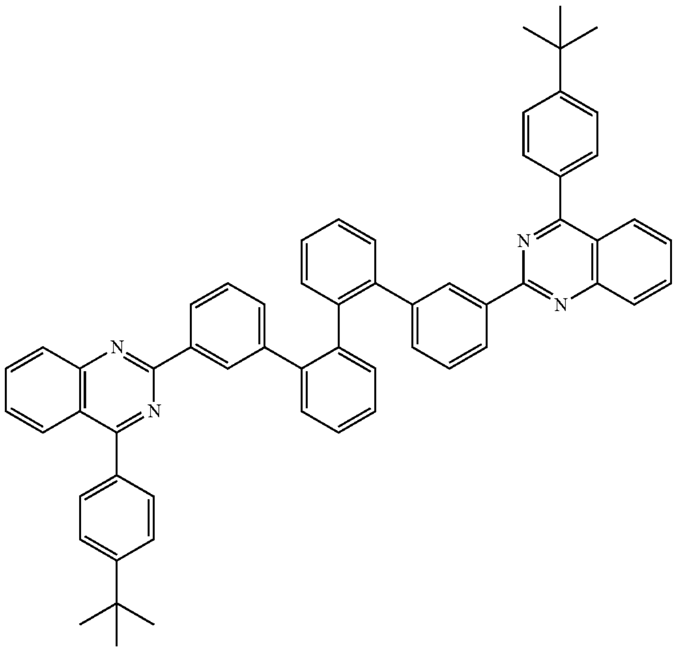

-continued
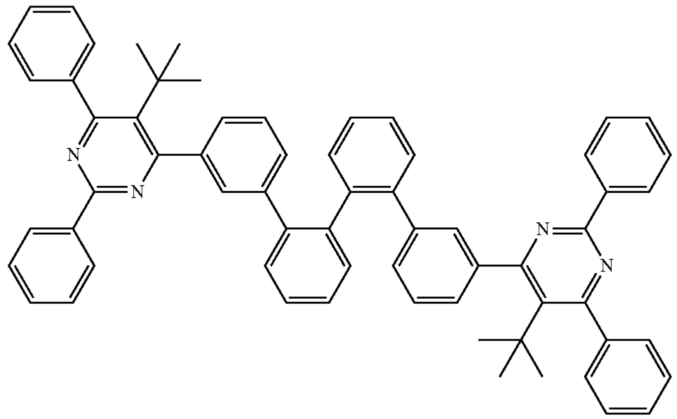
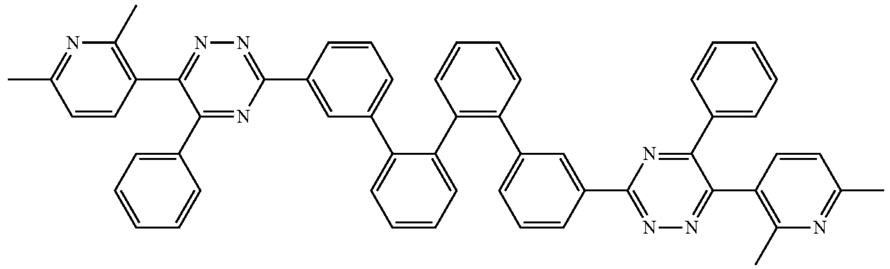
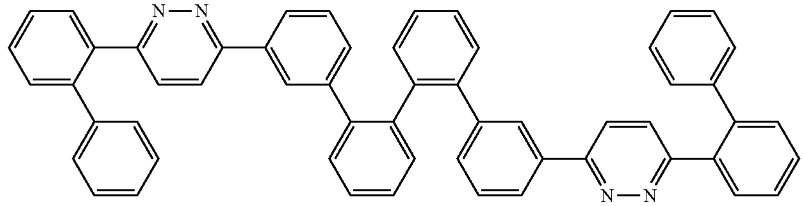
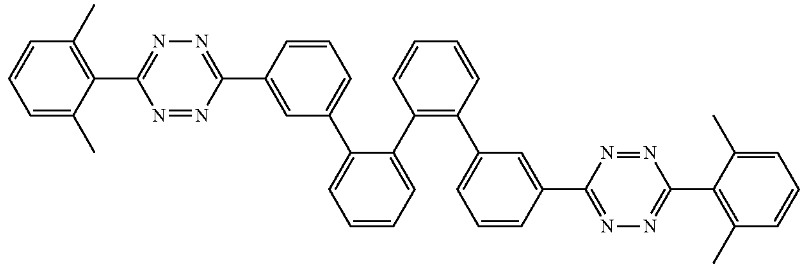
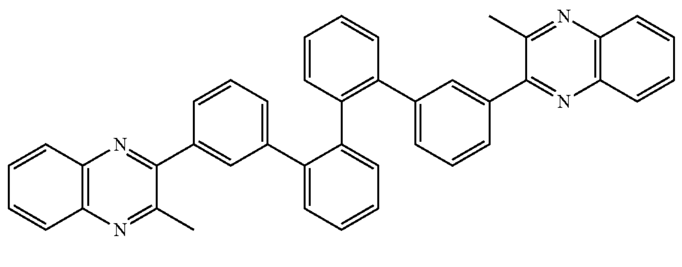

-continued
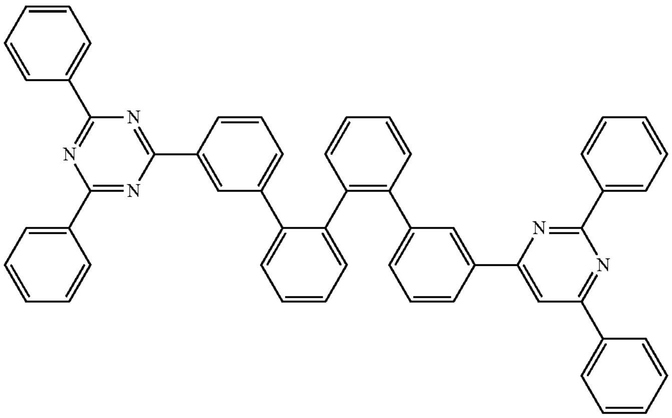
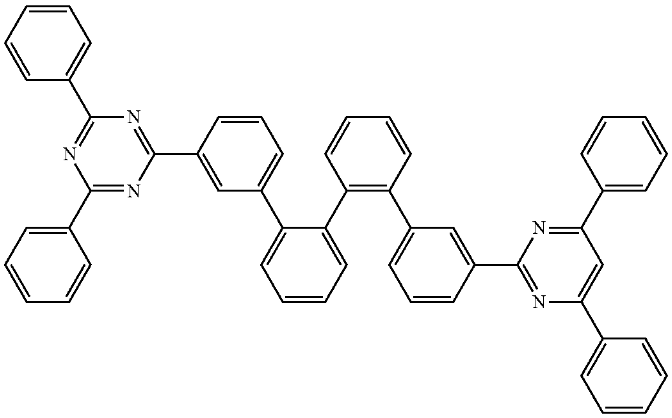
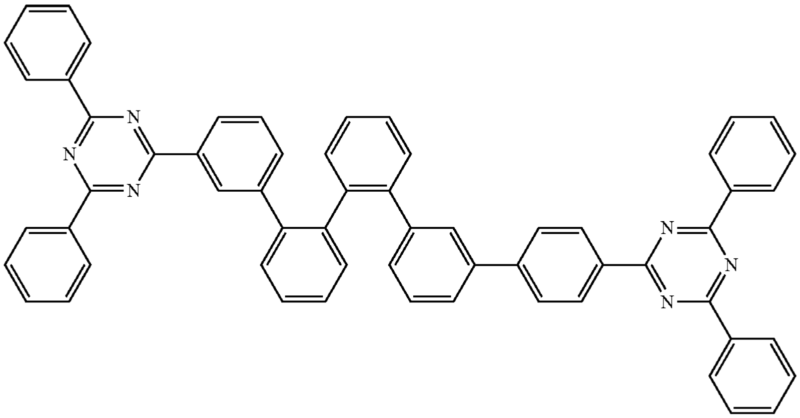
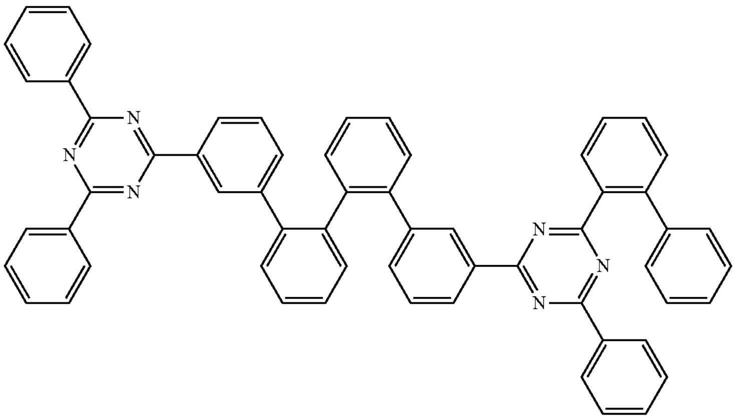

-continued
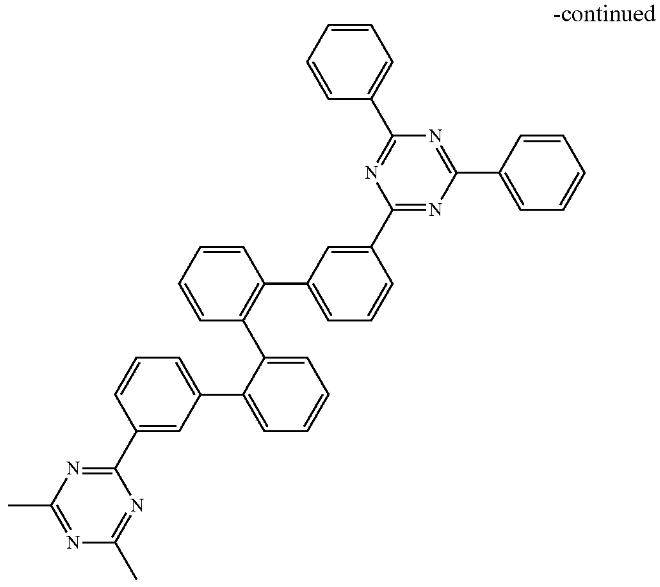
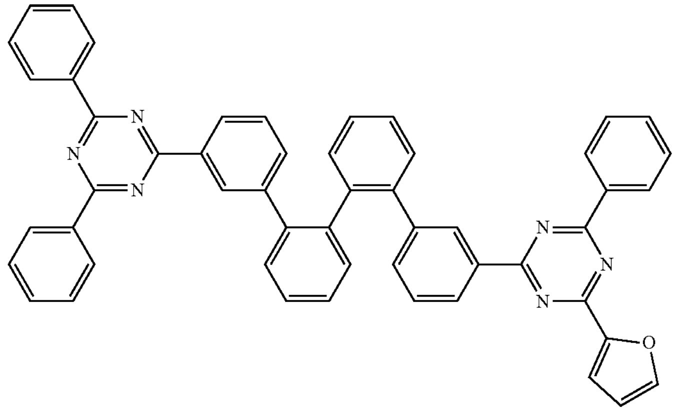
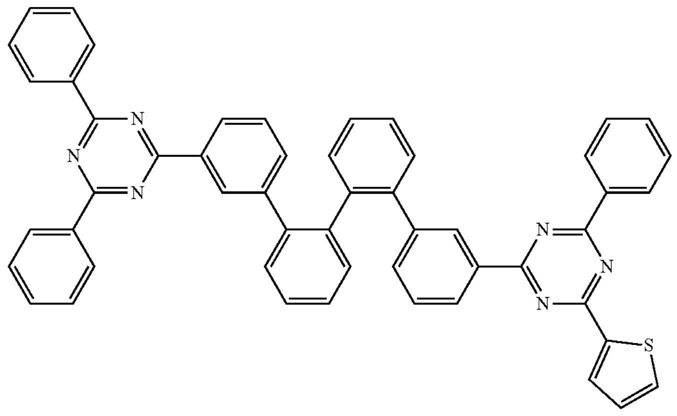

-continued
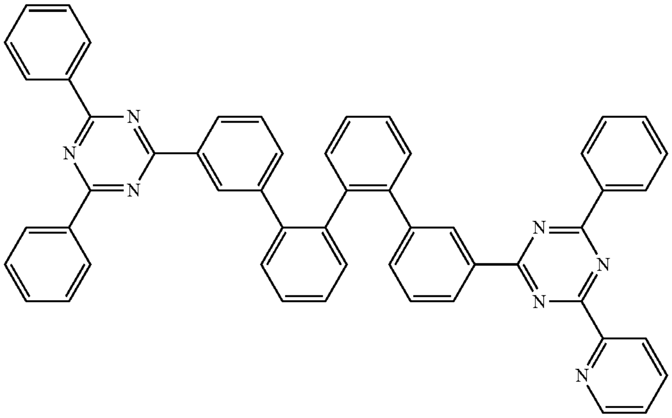
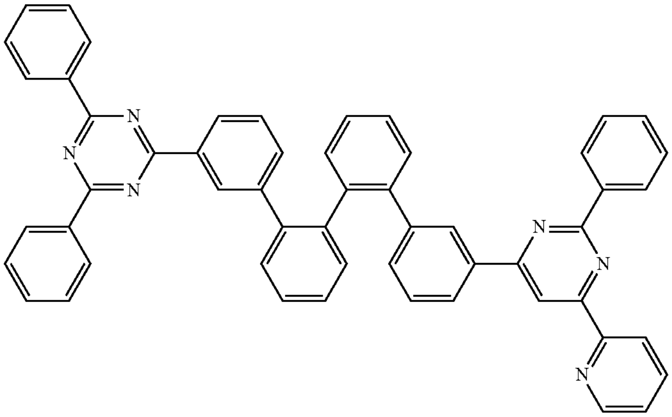
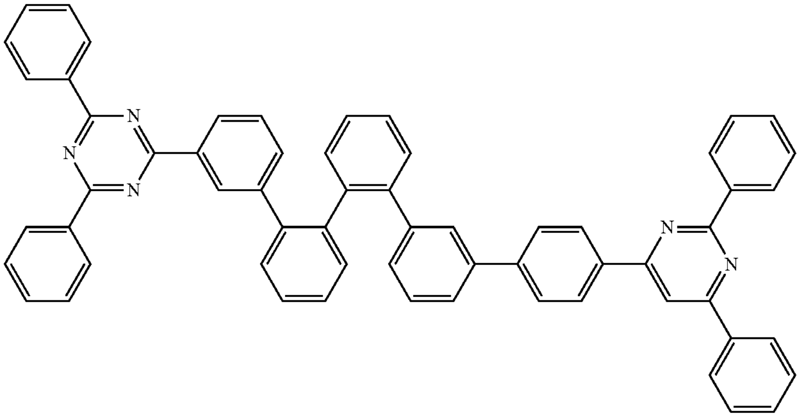
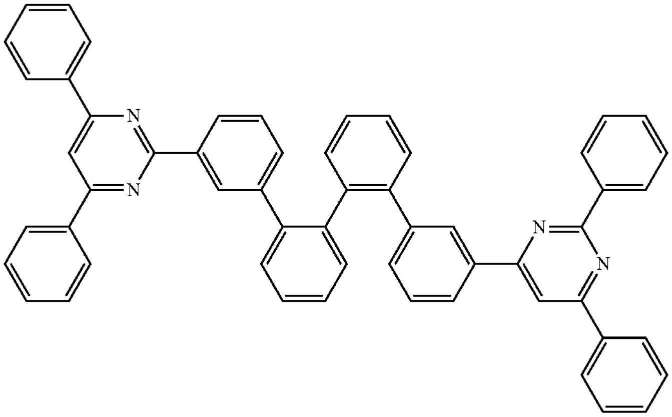

-continued
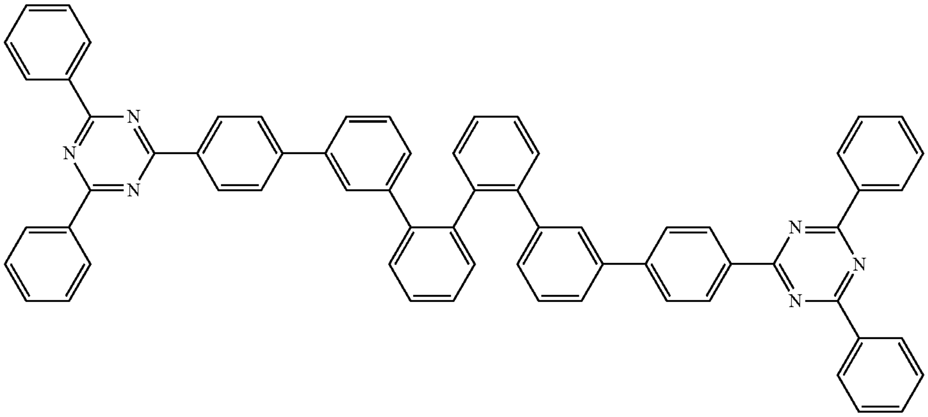
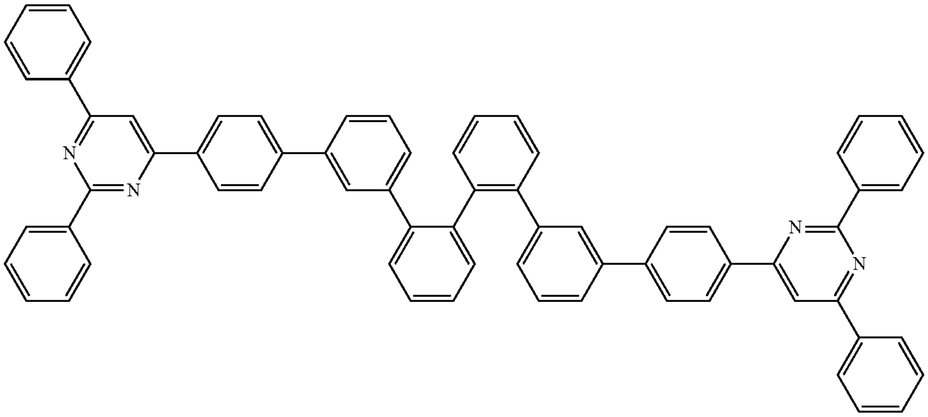
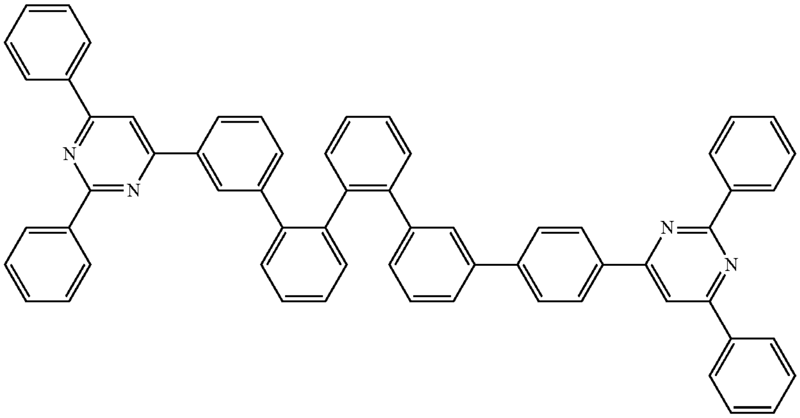
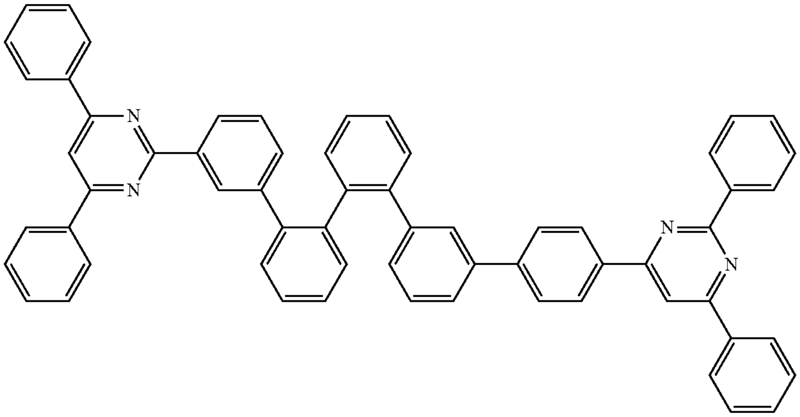

-continued
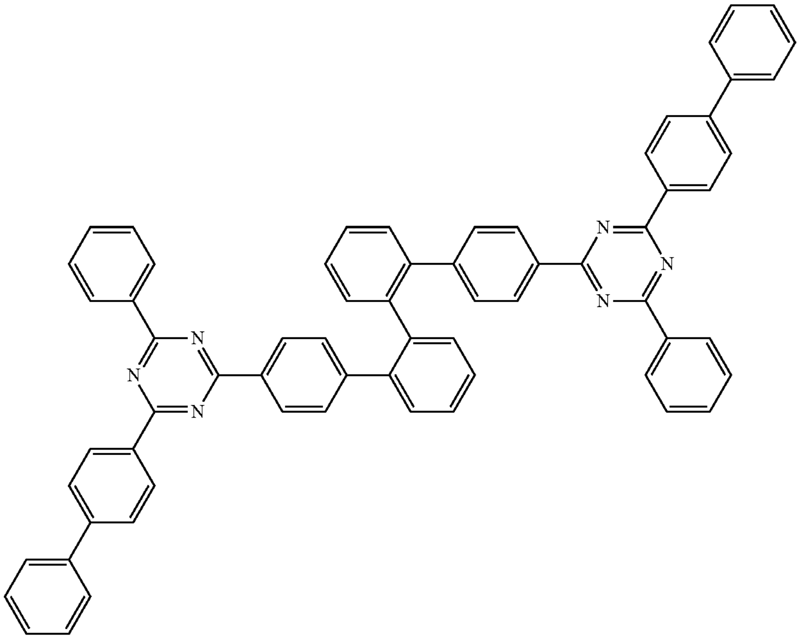
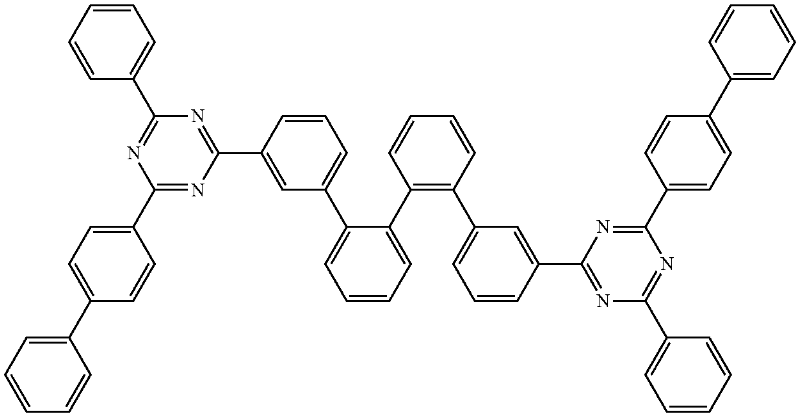
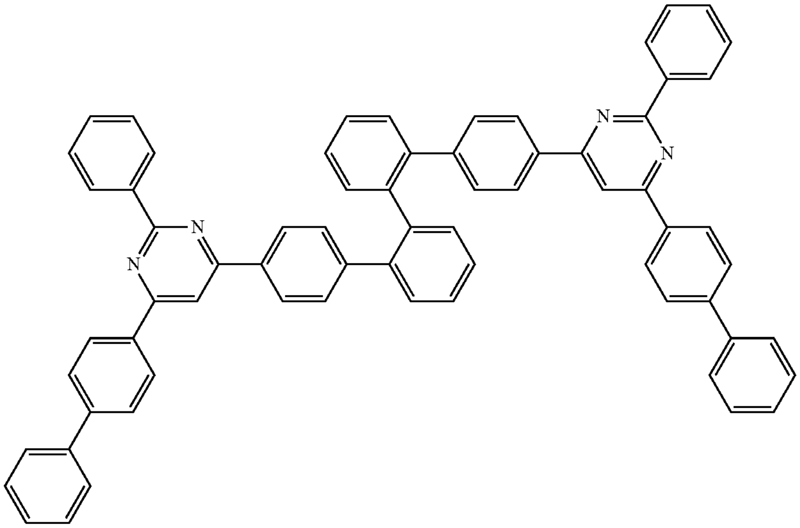

-continued
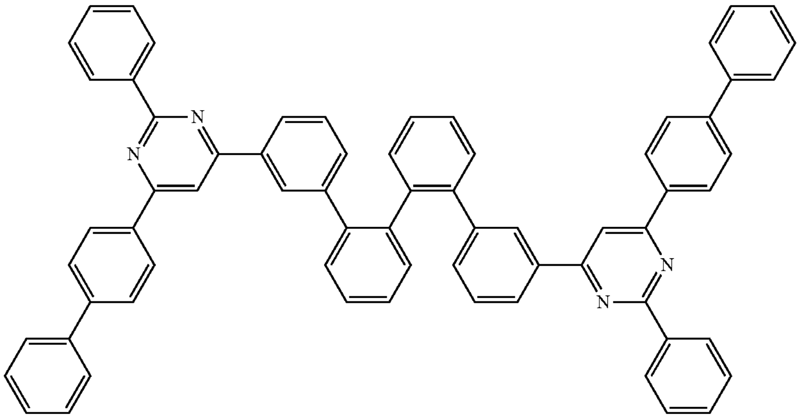
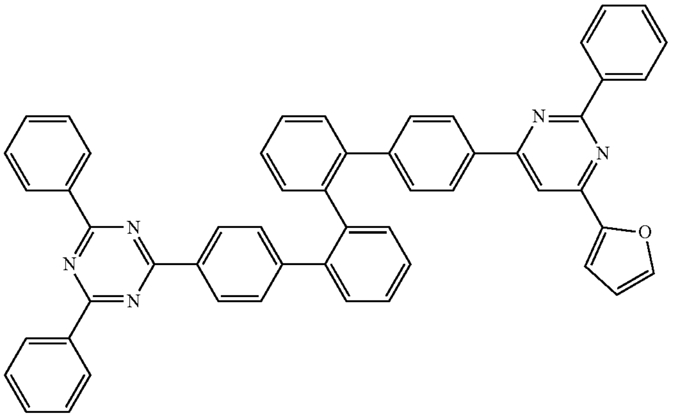
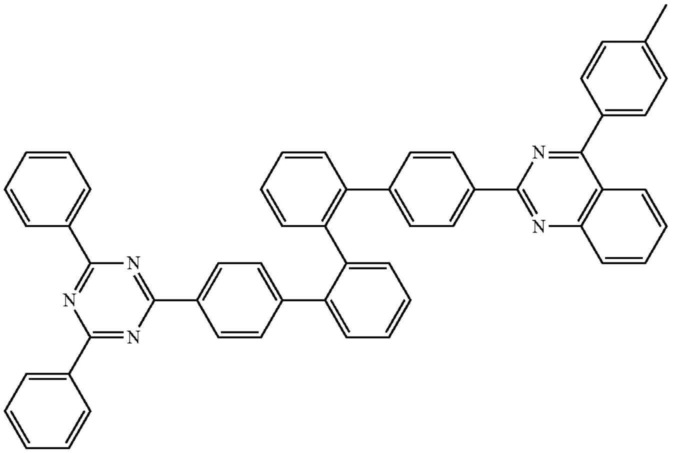
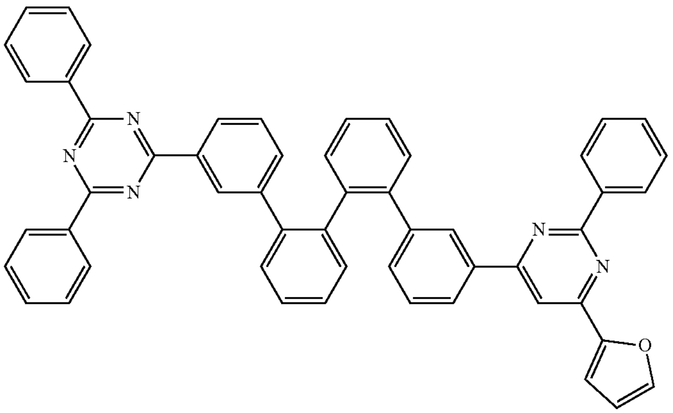

-continued
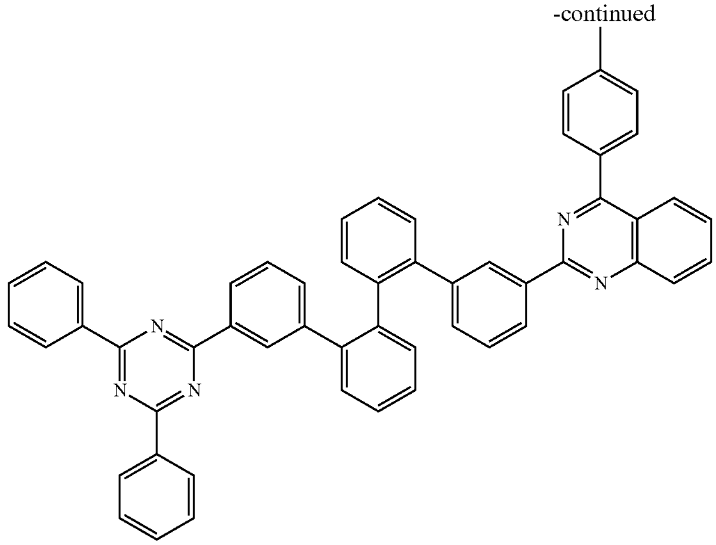
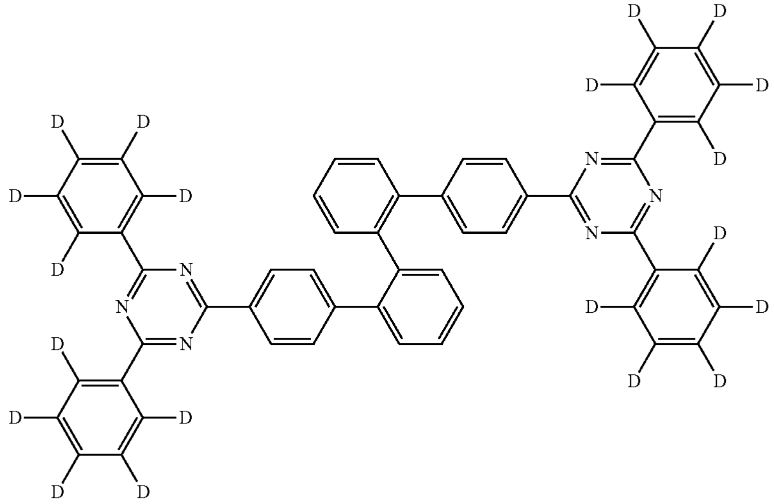
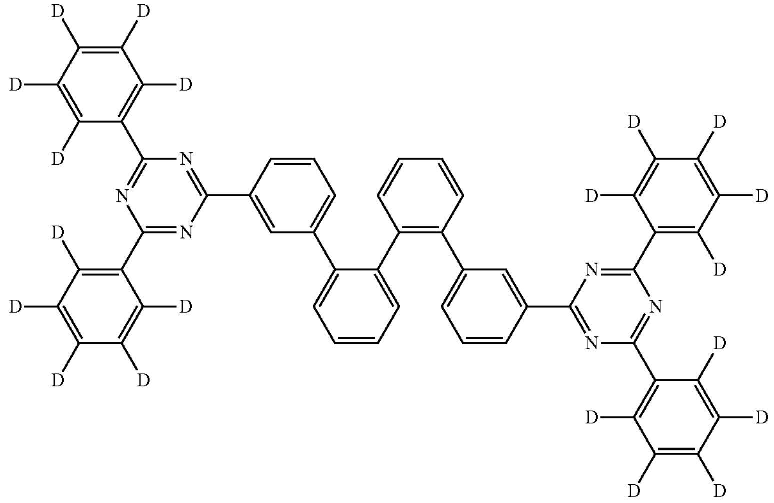

-continued
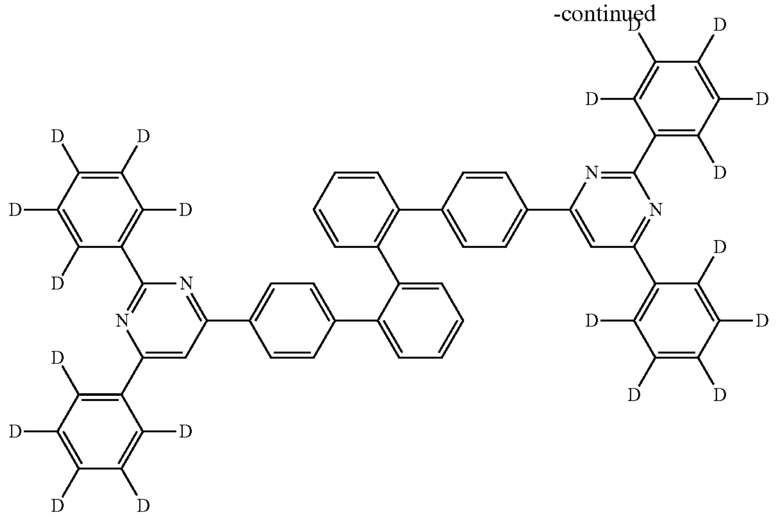
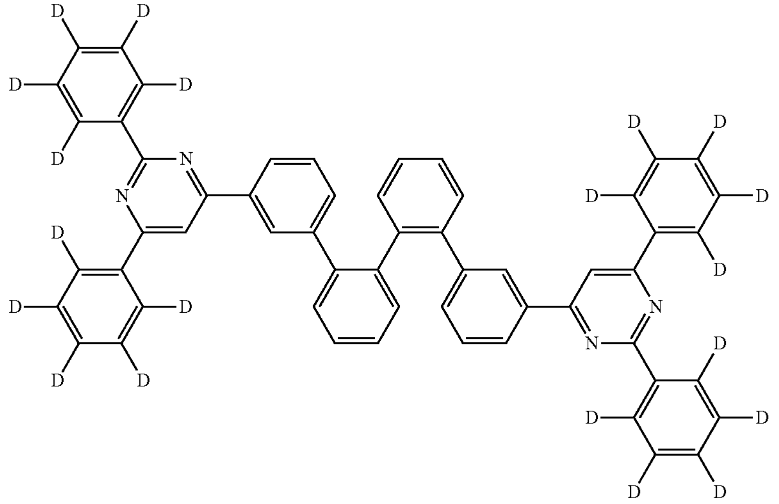
In addition, provided is a method for preparing a compound of Chemical Formula 1 or 2 as shown in Reaction Schemes 1 to 4 below.
[Reaction Scheme 1]
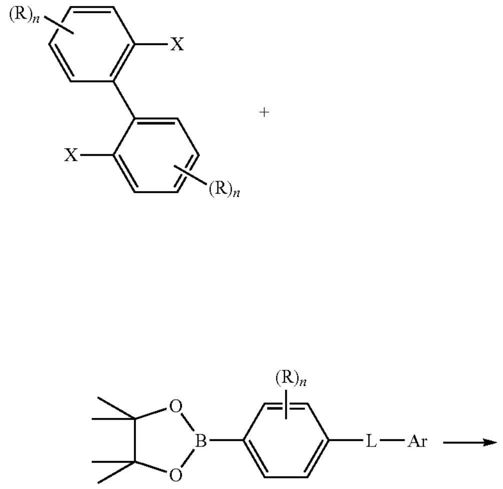
-continued
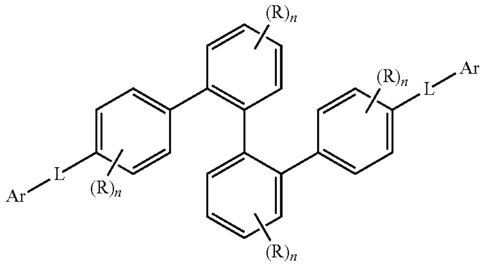
[Reaction Scheme 2]
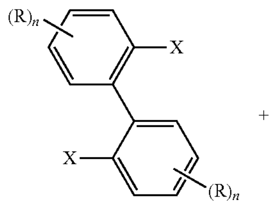

-continued

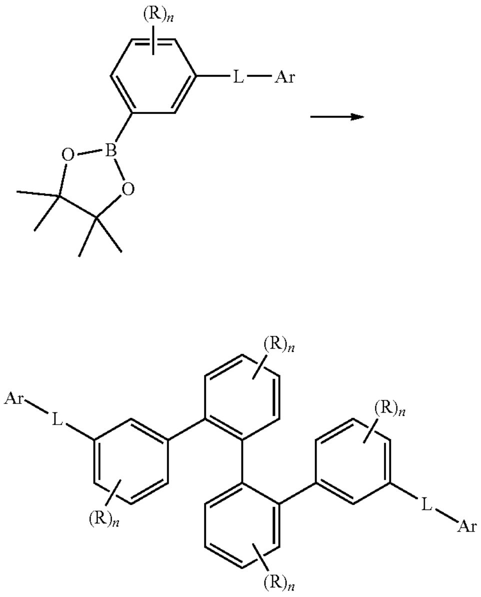

[Reaction Scheme 3]

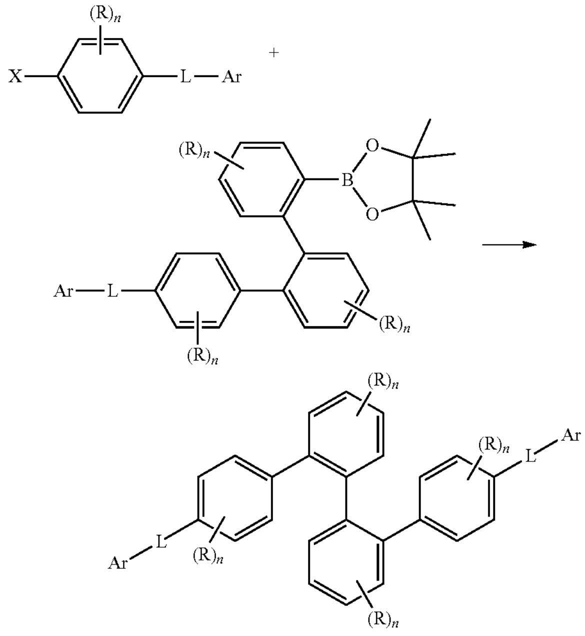

[Reaction Scheme 4]

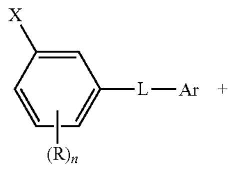

-continued

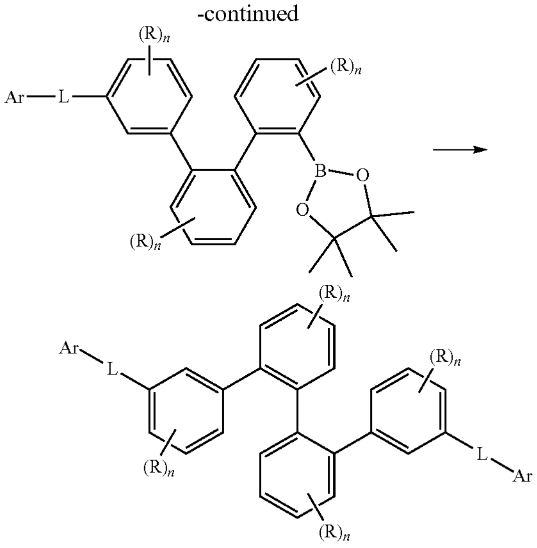

In the Reaction Schemes 1 to 4, each L is independently $L_1$ or $L_2$; each Ar is independently $Ar_1$ or $Ar_2$; each R is independently any one of $R_1$ to $R_4$; and each n is independently any one of n1 to n4. In addition, $L_1$, $L_2$, $Ar_1$, $Ar_2$, $R_1$ to $R_4$, and n1 to n4 are as defined above, and X is halogen, preferably bromo, or chloro.

(Organic Light Emitting Device)

In addition, according to another aspect of the present disclosure, provided is an organic light emitting device including at least one of the compound of Chemical Formula 1 and the compound of Chemical Formula 2. As an example, provided is an organic light emitting device including: a first electrode; a second electrode that is provided opposite to the first electrode; and one or more organic material layers that are provided between the first electrode and the second electrode, wherein at least one layer of the organic material layers includes at least one of the compound of Chemical Formula 1 and the compound of Chemical Formula 2.

The organic material layer of the organic light emitting device of the present disclosure can have a single-layer structure, or it can have a multilayered structure in which two or more organic material layers are stacked. For example, the organic light emitting device of the present disclosure can have a structure including a hole injection layer, a hole transport layer, an electron blocking layer, a light emitting layer, an electron transport layer, an electron injection layer, and the like as the organic material layer. However, the structure of the organic light emitting device is not limited thereto, and it can include a smaller number of organic material layers.

In addition, the organic material layer can include a hole injection layer, a hole transport layer, or a hole injection and transport layer, and the hole injection layer, the hole transport layer, or the hole injection and transport layer can include at least one of the compound of Chemical Formula 1 and the compound of Chemical Formula 2.

In addition, the organic material layer can include a light emitting layer, and the light emitting layer can include at least one of the compound of Chemical Formula 1 and the compound of Chemical Formula 2.

In addition, the organic material layer can include an electron transport layer or an electron injection layer, and the electron transport layer or the electron injection layer can include at least one of the compound of Chemical Formula 1 and the compound of Chemical Formula 2.

In addition, the electron transport layer, the electron injection layer, or the electron transport and injection layer can include at least one of the compound of Chemical Formula 1 and the compound of Chemical Formula 2.

The organic material layer can include an electron blocking layer, and the electron blocking layer is included between the anode and the light emitting layer. The electron blocking layer can include at least one of the compound of Chemical Formula 1 and the compound of Chemical Formula 2.

In addition, the organic material layer can include a light emitting layer and an electron transport layer, and the electron transport layer can include at least one of the compound of Chemical Formula 1 and the compound of Chemical Formula 2.

The organic material layer can include a hole blocking layer, and the hole blocking layer is included between the cathode and the light emitting layer. The hole blocking layer serves to improve the efficiency of an organic light emitting device by suppressing holes injected from the anode from being transferred to the cathode without recombination in the light emitting layer. The hole blocking layer can include at least one of the compound of Chemical Formula 1 and the compound of Chemical Formula 2.

Preferably, the organic material layer is an electron transport layer, an electron injection layer, or an electron transport and injection layer.

Preferably, the electron transport layer, the electron injection layer, or the electron transport and injection layer can further include a compound of Chemical Formula 4:

[Chemical Formula 4]

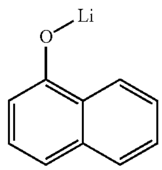

Further, the organic light emitting device according to the present disclosure can be a normal type organic light emitting device in which an anode, one or more organic material layers and a cathode are sequentially stacked on a substrate. Further, the organic light emitting device according to the present disclosure can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 to 3.

FIG. 1 shows an example of an organic light emitting device including a substrate 1, an anode 2, a light emitting layer 3, and a cathode 4. In such a structure, at least one of the compound of Chemical Formula 1 and the compound of Chemical Formula 2 can be included in the light emitting layer.

FIG. 2 shows an example of an organic light emitting device including a substrate 1, an anode 2, a hole injection layer 5, a hole transport layer 6, a light emitting layer 7, an electron transport and injection layer 8, and a cathode 4. In such a structure, at least one of the compound of Chemical Formula 1 and the compound of Chemical Formula 2 can be included in at least one layer of the hole injection layer, the hole transport layer, the light emitting layer, and the electron transport and injection layer.

FIG. 3 shows an example of an organic light emitting device including a substrate 1, an anode 2, a hole injection layer 5, a hole transport layer 6, an electron blocking layer 9, a light emitting layer 7, a hole blocking layer 10, an electron transport and injection layer 8, and a cathode 4. In such a structure, at least one of the compound of Chemical Formula 1 and the compound of Chemical Formula 2 can be included in at least one layer of the hole injection layer, the hole transport layer, the electron blocking layer, the light emitting layer, the hole blocking layer, and the electron transport and injection layer.

The organic light emitting device according to the present disclosure can be manufactured using materials and methods known in the art, except that at least one layer of the organic material layers includes at least one of the compound of Chemical Formula 1 and the compound of Chemical Formula 2. Moreover, when the organic light emitting device includes a plurality of organic material layers, the organic material layers can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, at least one of the compound of Chemical Formula 1 and the compound of Chemical Formula 2 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

For example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

In addition, the hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is suitably a material capable of emitting light in a visible ray region by receiving holes and electrons from the hole transport layer and the electron transport layer, respectively, to combine them, and having good quantum efficiency to fluorescence or phosphorescence. Specific examples thereof include 8-hydroxy-quinoline aluminum complex ($Alq_3$); a carbazole-based compound; a dimerized styryl compound; BAlq; a 10-hydroxybenzo quinoline-metal compound; a benzoxazole-, benzothiazole- and benzimidazole-based compound; a poly(p-phenylenevinylene) (PPV)-based polymer; a spiro compound; polyfluorene, rubrene, and the like, but are not limited thereto.

In addition, the light emitting layer can include a host material and a dopant material. The host material can be a fused aromatic ring derivative or a heterocycle-containing compound. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material used is suitably a material which can receive electrons well from a cathode and transfer the electrons to a light emitting layer and has large mobility for electrons. Specifically, examples thereof can include an Al complex of 8-hydroxyquinoline; a complex including $Alq_3$; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)-beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure can be a front side emission type, a backside emission type, or a double-sided emission type according to the used material.

In addition, the compound according to the present disclosure can be included in an organic solar cell or an organic transistor in addition to an organic light emitting device.

The preparation of the compound of Chemical Formula 1 or Chemical Formula 2 and the organic light emitting device including the same will be described in detail in the following examples. However, these examples are presented for illustrative purposes only, and are not intended to limit the scope of the present disclosure.

EXAMPLES

Example 1: Preparation of Compound E1

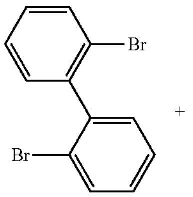

E1-A

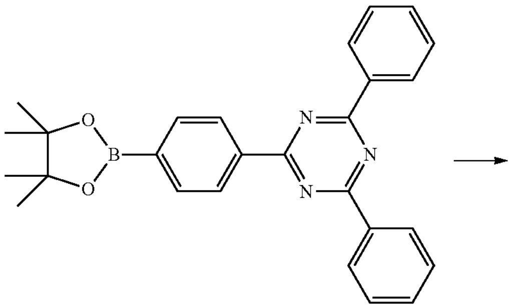

E1-B

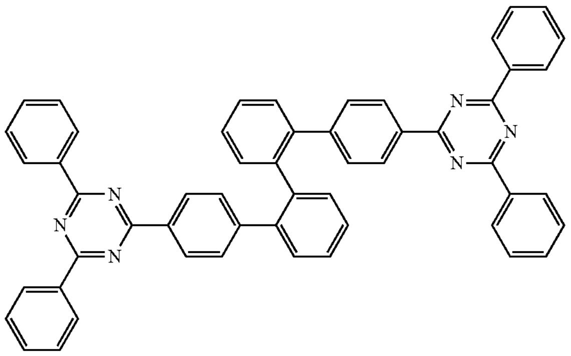

E1

E1-A (20 g, 64.1 mmol) and E1-B (55.8 g, 128.2 mmol) were added to tetrahydrofuran (400 ml) under a nitrogen atmosphere, and the mixture was stirred and refluxed. Then, potassium carbonate (26.6 g, 192.3 mmol) was dissolved in water (27 ml), and then added thereto. Thereafter, it was stirred sufficiently, followed by adding tetrakistriphenylphosphinopalladium (2.2 g, 1.9 mmol). After 1 hour of reaction, cooling was performed to room temperature. Then, the organic layer was separated from the water layer, and then the organic layer was distilled. Then, this was dissolved again in chloroform (20 times, 986 mL), and washed twice with water. Thereafter, the organic layer was separated, treated with anhydrous magnesium sulfate, stirred, then filtered, and the filtrate was distilled under reduced pressure. The concentrated compound was recrystallized with chloroform and ethyl acetate to prepare Compound E1 in the form of white solid (32.5 g, 66%).

MS: $[M+H]^+=769$

Example 2: Preparation of Compound E2

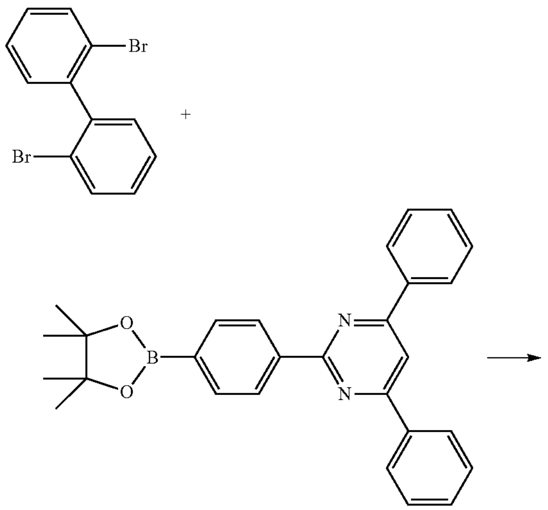

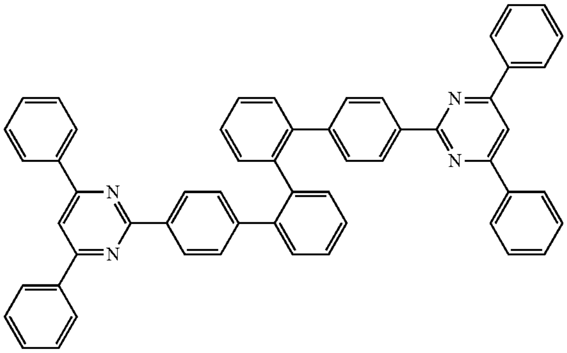

E2

Compound E2 was prepared in the same manner as in Example 1, except that each starting material was used as in the above reaction scheme.

MS: $[M+H]^+=767$

Example 3: Preparation of Compound E3

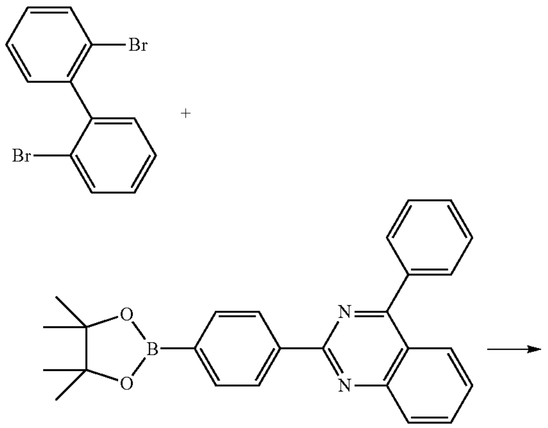

-continued

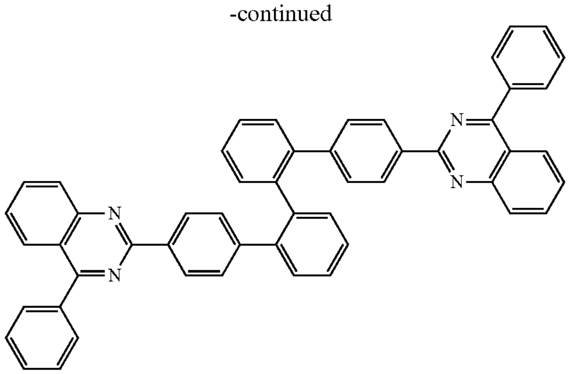

E3

Compound E3 was prepared in the same manner as in Example 1, except that each starting material was used as in the above reaction scheme.

MS: $[M+H]^+$=715

Example 4: Preparation of Compound E4

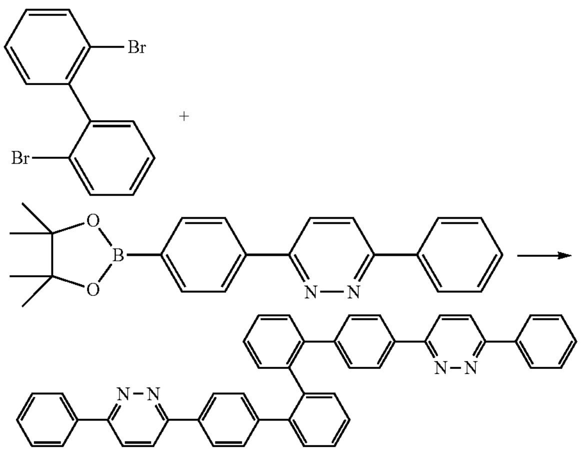

E4

Compound E4 was prepared in the same manner as in Example 1, except that each starting material was used as in the above reaction scheme.

MS: $[M+H]^+$=615

Example 5: Preparation of Compound E5

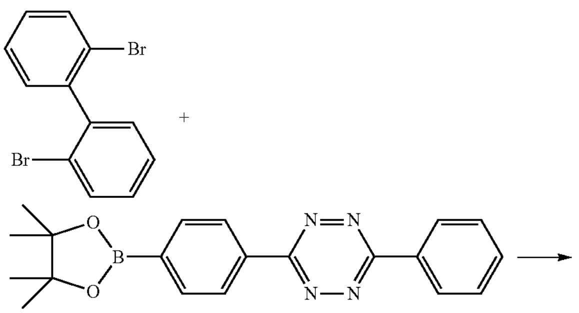

-continued

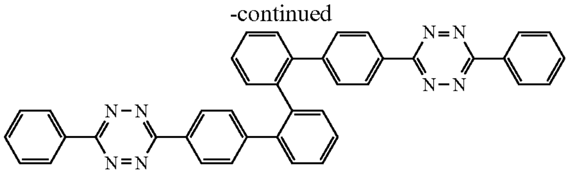

E5

Compound E5 was prepared in the same manner as in Example 1, except that each starting material was used as in the above reaction scheme.

MS: $[M+H]^+$=619

Example 6: Preparation of Compound E6

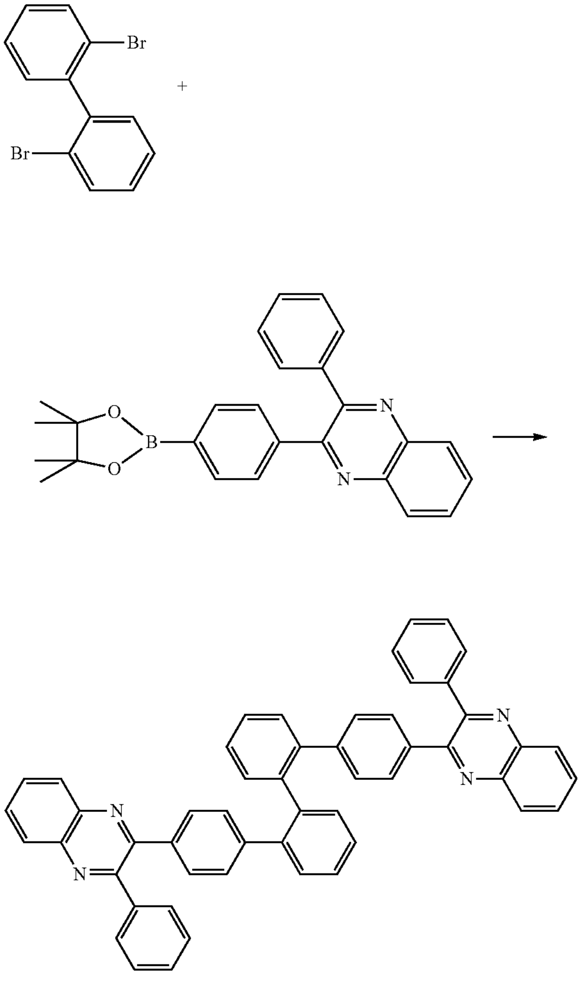

E6

Compound E6 was prepared in the same manner as in Example 1, except that each starting material was used as in the above reaction scheme.

MS: $[M+H]^+$=715

Example 7: Preparation of Compound E7
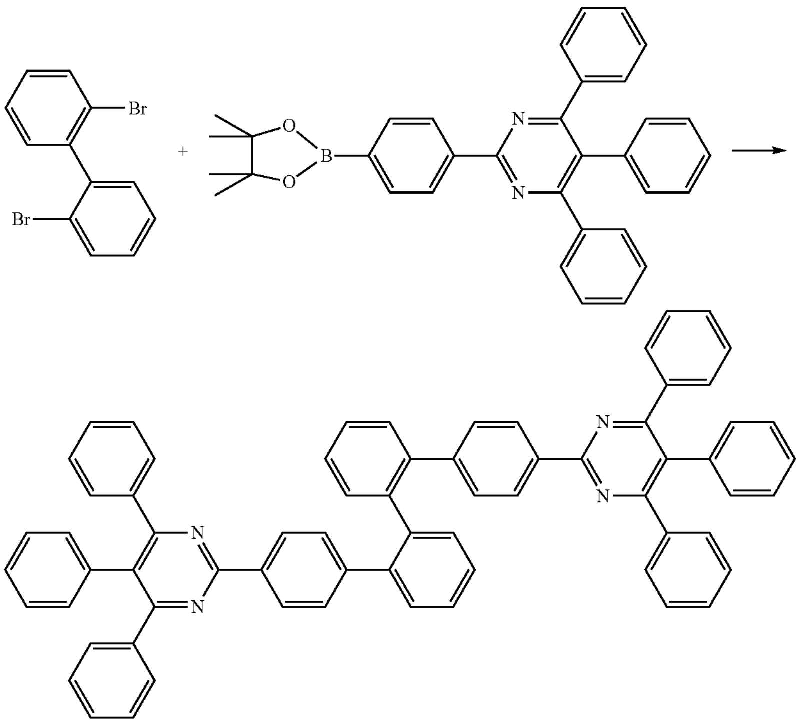
E7
Compound E7 was prepared in the same manner as in Example 1, except that each starting material was used as in the above reaction scheme.
MS: $[M+H]^+$=919
Example 8: Preparation of Compound E8
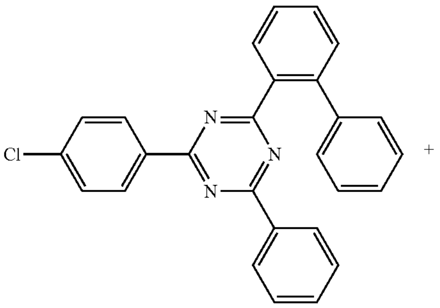
E8-A
-continued
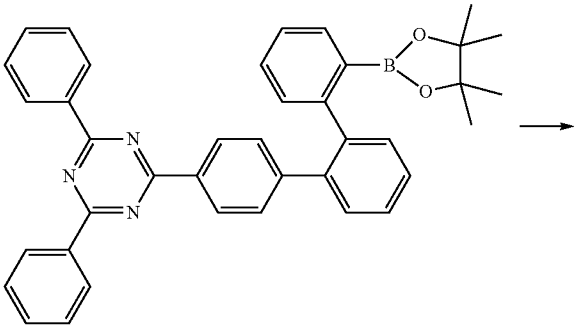
E8-B
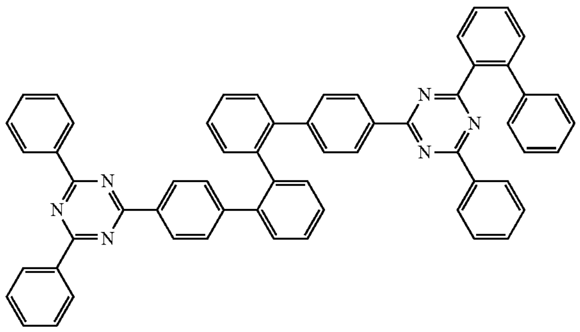
E8
E8-A (20 g, 47.6 mmol) and E8-B (28 g, 47.6 mmol) were added to 1,4-dioxane (400 ml) under a nitrogen atmosphere, and the mixture was stirred and refluxed. Then, tripotassium phosphate (30.3 g, 142.9 mmol) was dissolved in water (30 ml), and then added thereto. Thereafter, it was stirred sufficiently, followed by adding dibenzylidene acetone palladium (0.8 g, 1.4 mmol) and tricyclohexylphosphine (0.8 g, 2.9 mmol). After 5 hours of reaction, cooling was performed to room temperature, and the resulting solid was filtered. The resulting solid was dissolved again in chloroform (30 times, 1207 mL), and washed twice with water. Thereafter, the organic layer was separated, treated with anhydrous magnesium sulfate, stirred, then filtered, and the filtrate was distilled under reduced pressure. The concentrated compound was recrystallized with chloroform and ethyl acetate to prepare Compound E8 in the form of white solid (6 g, 15%).

MS: $[M+H]^+=845$

Example 9: Preparation of Compound E9

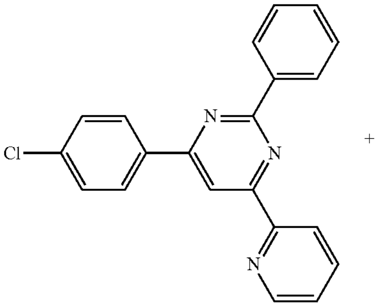

-continued

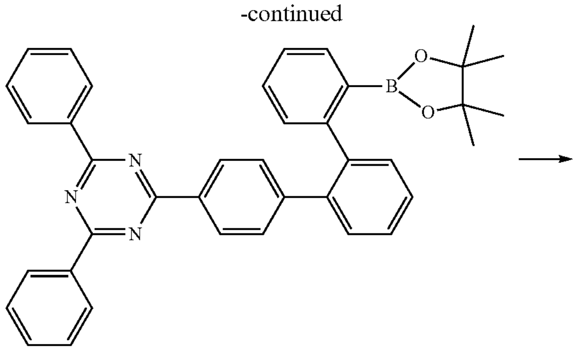

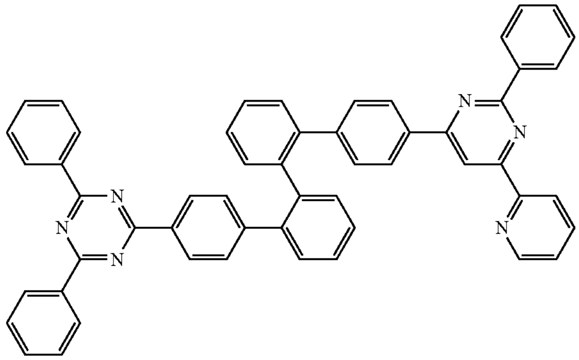

E9

Compound E9 was prepared in the same manner as in Example 8, except that each starting material was used as in the above reaction scheme.

MS: $[M+H]^+=769$

Example 10: Preparation of Compound E10

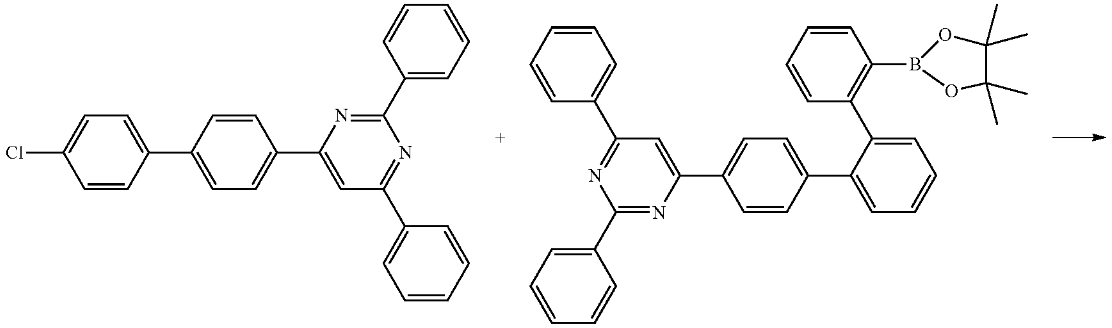

-continued

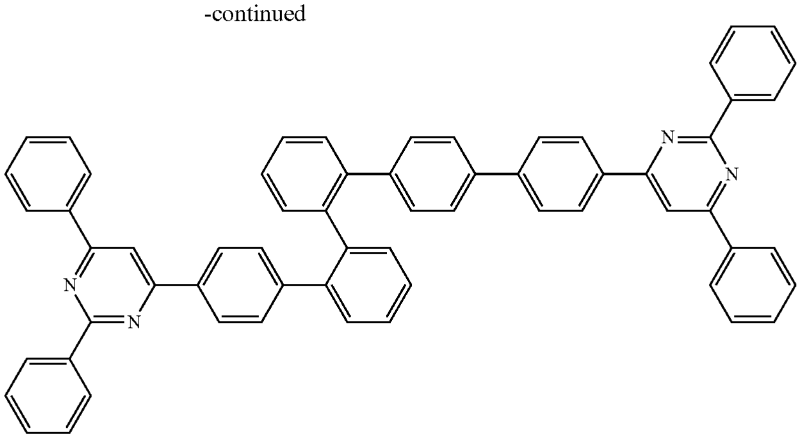

E10

Compound E10 was prepared in the same manner as in Example 8, except that each starting material was used as in the above reaction scheme.

MS: $[M+H]^+$=843

Example 11: Preparation of Compound E11

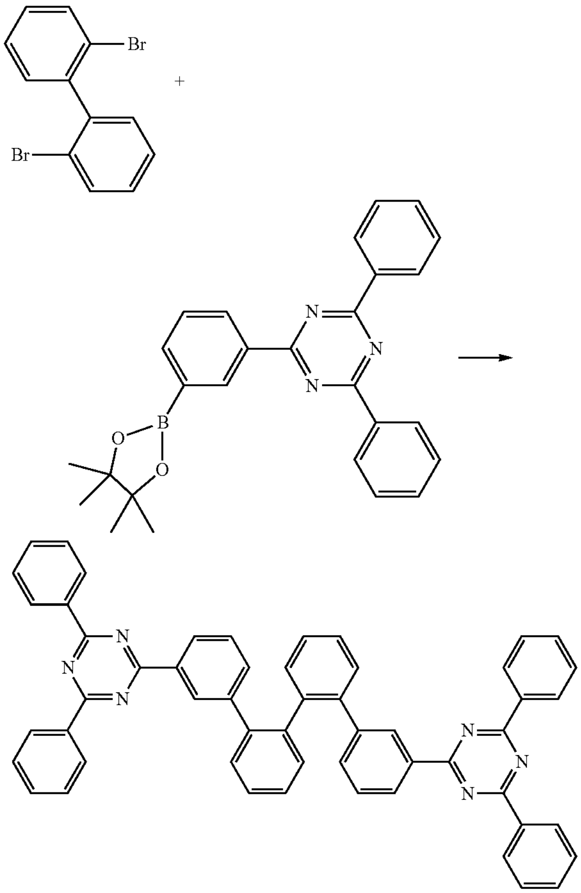

E11

Compound E11 was prepared in the same manner as in Example 1, except that each starting material was used as in the above reaction scheme.

MS: $[M+H]^+$=769

Example 12: Preparation of Compound E12

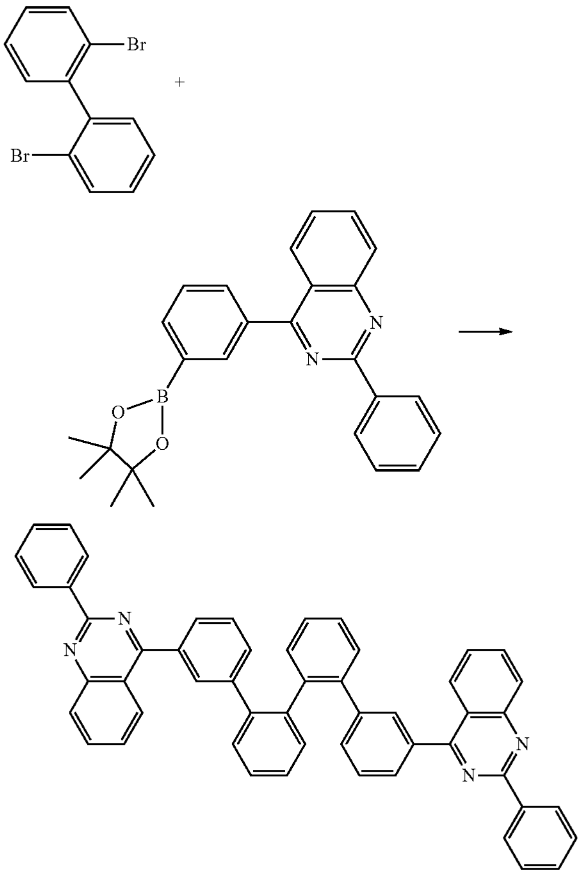

E12

Compound E12 was prepared in the same manner as in Example 1, except that each starting material was used as in the above reaction scheme.

MS: $[M+H]^+$=715

Example 13: Preparation of Compound E13

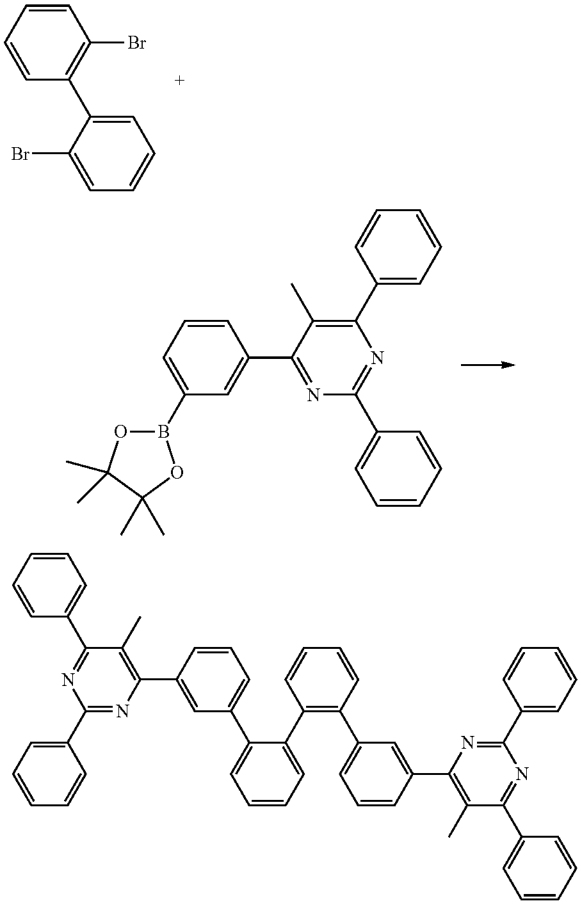

E13

Compound E13 was prepared in the same manner as in Example 1, except that each starting material was used as in the above reaction scheme.

MS: $[M+H]^+$=795

Example 14: Preparation of Compound E14

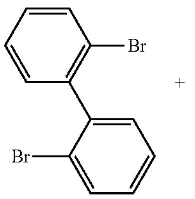

-continued

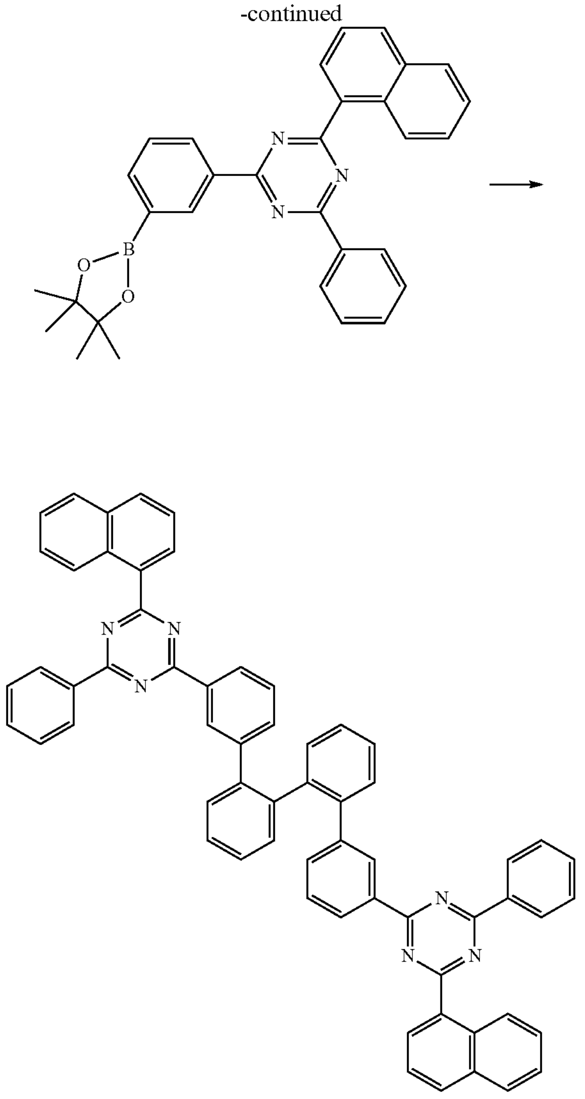

E14

Compound E14 was prepared in the same manner as in Example 1, except that each starting material was used as in the above reaction scheme.

MS: $[M+H]^+$=869

Example 15: Preparation of Compound E15

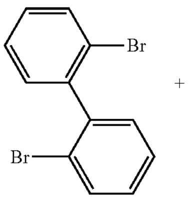

-continued

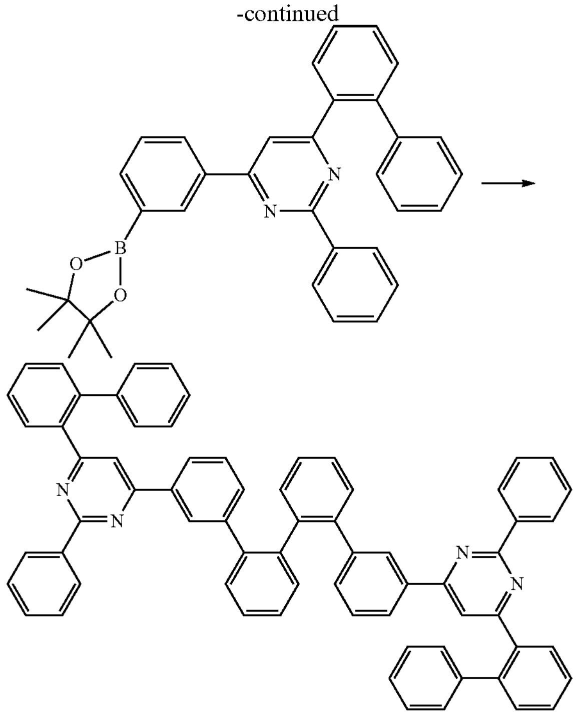

E15

Compound E15 was prepared in the same manner as in Example 1, except that each starting material was used as in the above reaction scheme.

MS: $[M+H]^+$=919

Example 16: Preparation of Compound E16

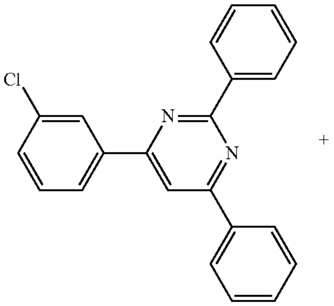

-continued

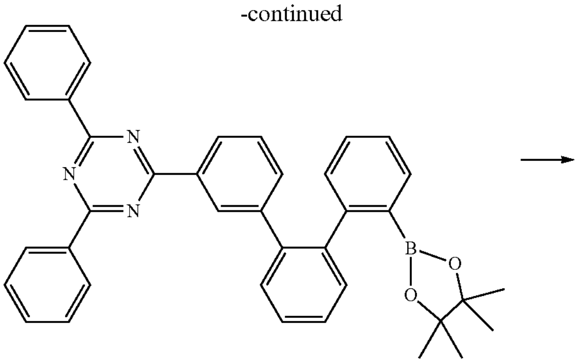

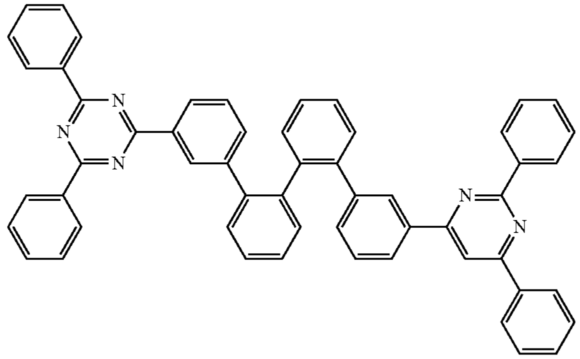

E16

Compound E16 was prepared in the same manner as in Example 8, except that each starting material was used as in the above reaction scheme.

MS: $[M+H]^+$=768

Example 17: Preparation of Compound E17

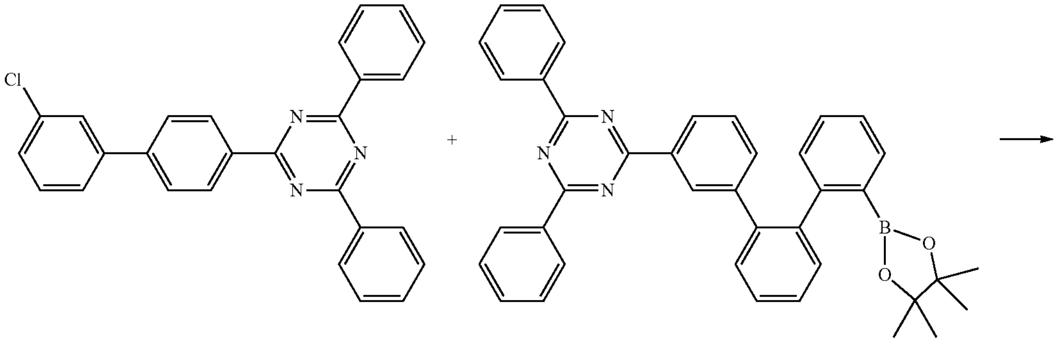

-continued

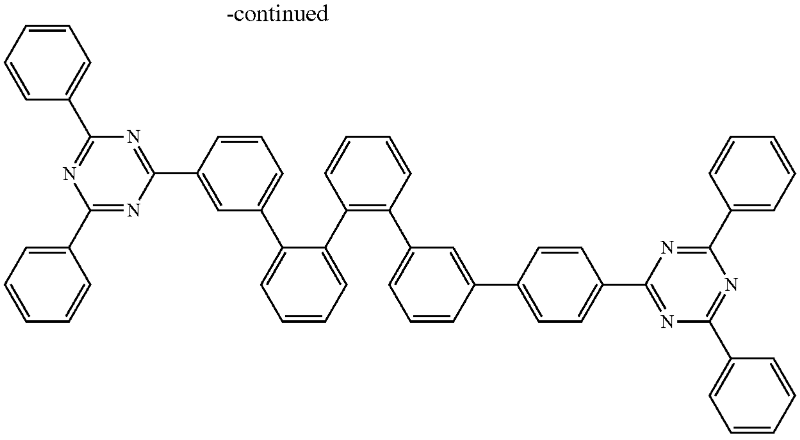

E17

Compound E17 was prepared in the same manner as in Example 8, except that each starting material was used as in the above reaction scheme.

MS: $[M+H]^+$=845

Example 18: Preparation of Compound E18

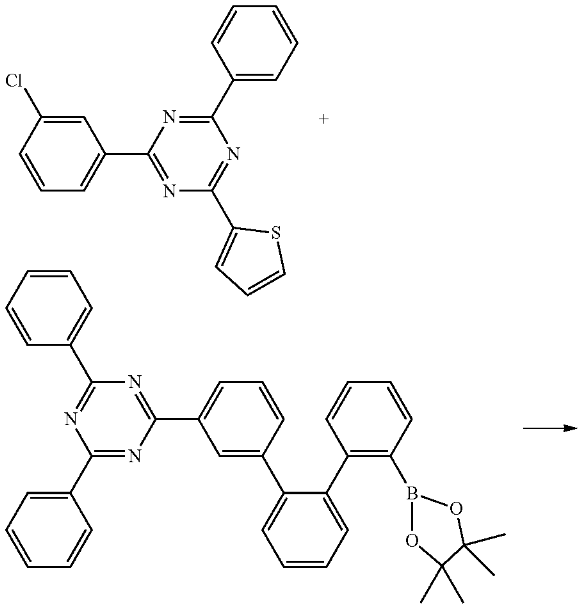

-continued

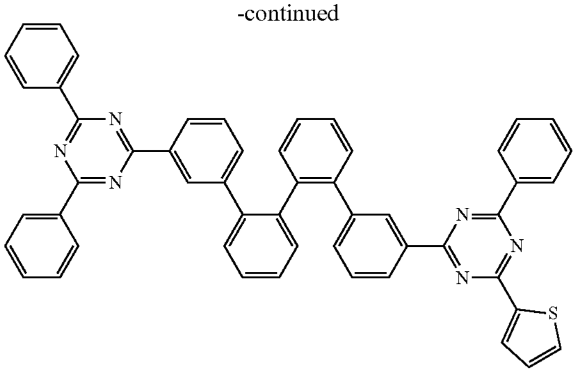

E18

Compound E18 was prepared in the same manner as in Example 8, except that each starting material was used as in the above reaction scheme.

MS: $[M+H]^+$=775

Example 19: Preparation of Compound E19

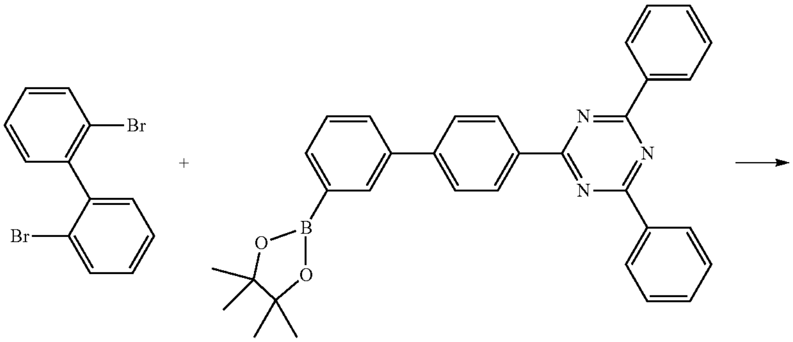

-continued
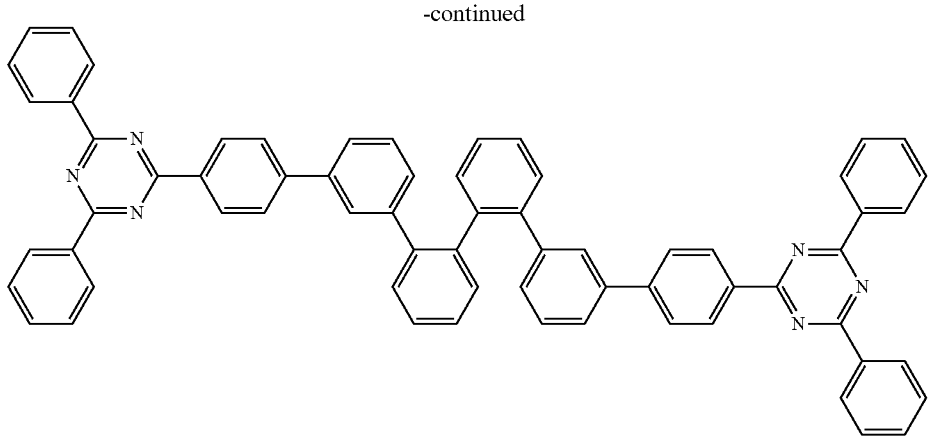
E19
Compound E19 was prepared in the same manner as in Example 1, except that each starting material was used as in the above reaction scheme.
MS: $[M+H]^+$=921
Example 20 Preparation of Compound E20
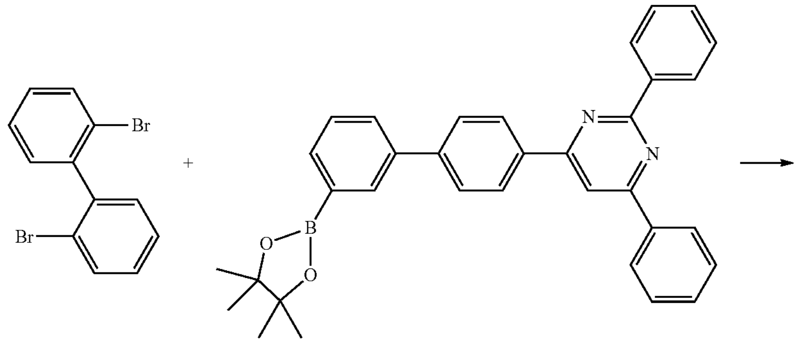
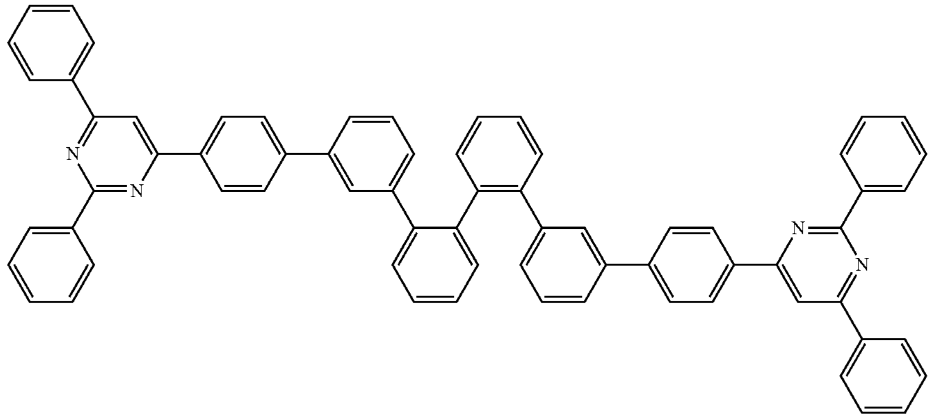
E20

Compound E20 was prepared in the same manner as in Example 1, except that each starting material was used as in the above reaction scheme.

MS: $[M+H]^+=919$

EXPERIMENTAL EXAMPLES

Experimental Example 1

A glass substrate on which ITO (Indium Tin Oxide) was coated as a thin film to a thickness of 1,000 Å was put into distilled water in which a detergent was dissolved, and ultrasonically cleaned. At this time, a product manufactured by Fischer Co. was used as the detergent, and distilled water filtered twice using a filter manufactured by Millipore Co. was used as the distilled water. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. Then, the substrate was cleaned for 5 minutes using oxygen plasma and then transferred to a vacuum depositor.

On the prepared ITO transparent electrode, the following Compound HI-A was thermally vacuum-deposited to a thickness of 600 Å to form a hole injection layer. On the hole injection layer, hexaazatriphenylene (HAT, 50 Å) with the following formula and the following Compound HT-A (600 Å) were sequentially vacuum-deposited to form a hole transport layer.

Then, the following Compounds BH and BD were vacuum-deposited on the hole transport layer at a weight ratio of 25:1 to a thickness of 200 Å to form a light emitting layer.

The Compound E1 of Example 1 and the following Compound LiQ (Lithium quinolate) were vacuum-deposited on the light emitting layer at a weight ratio of 1:1 to a thickness of 350 Å to form an electron transport and injection layer. On the electron transport and injection layer, lithium fluoride (LiF) and aluminum were sequentially deposited to a thickness of 10 Å and 1,000 Å, respectively to form a cathode.

HI-A

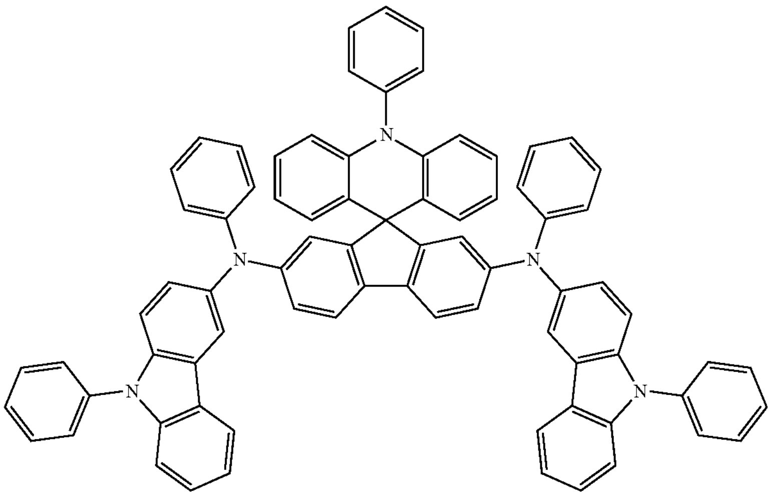

HAT

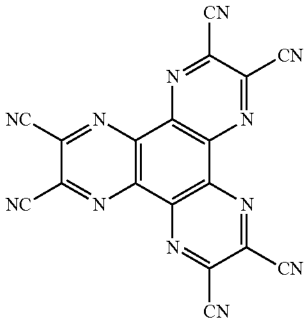

HT-A

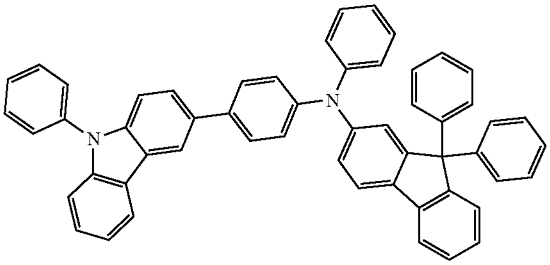

-continued

BH

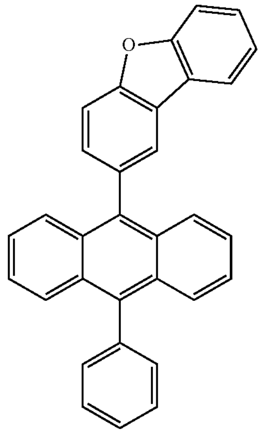

BD

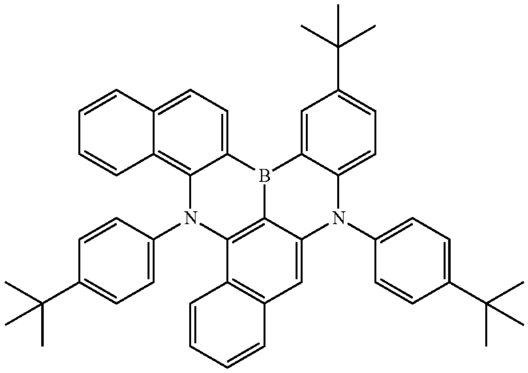

LiQ

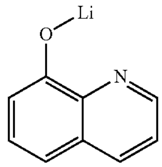

In the above process, the deposition rate of the organic material was maintained at 0.4 to 0.9 Å/sec, the deposition rate of lithium fluoride of the cathode was maintained at 0.3 Å/sec, and the deposition rate of aluminum was maintained at 2 Å/sec. In addition, the degree of vacuum during the deposition was maintained at $1\times10^{-7}$ to $5\times10^{-8}$ torr, thereby manufacturing an organic light emitting device.

Experimental Examples 2 to 20

An organic light emitting device was manufactured in the same manner as in Experimental Example 1, except that the compound shown in Table 1 was used instead of the compound of Example 1.

Comparative Experimental Examples 1 to 19

An organic light emitting device was manufactured in the same manner as in Experimental Example 1, except that the compound shown in Table 1 was used instead of the compound of Example 1. At this time, Compounds ET-1 to ET-19 listed in Table 1 are as follows.

ET-1

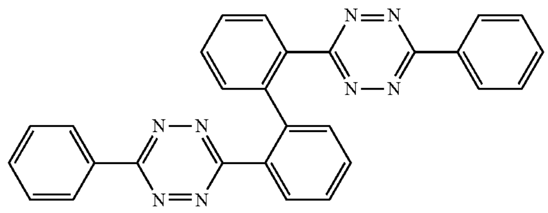

ET-2

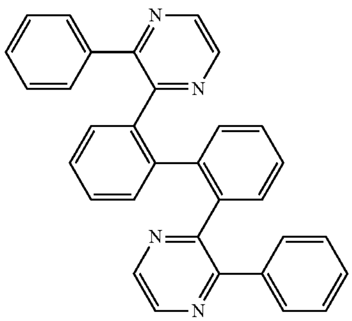

-continued
ET-3
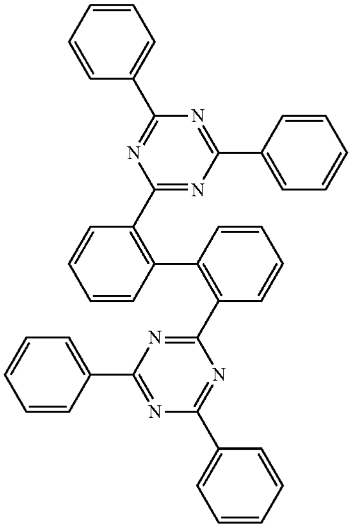
ET-4
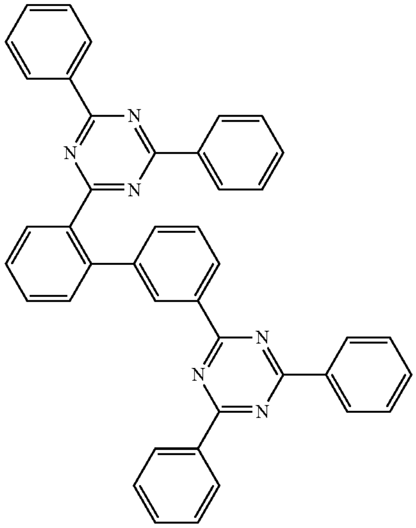
ET-5
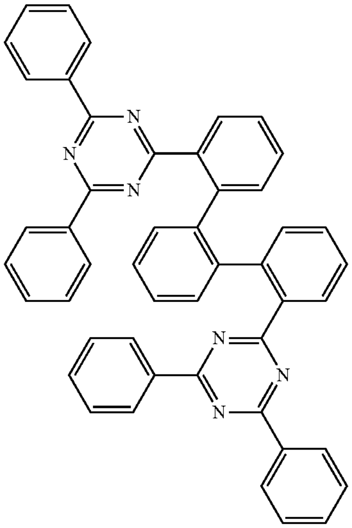
ET-6
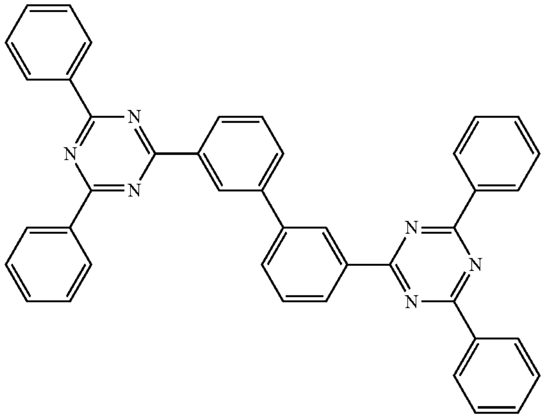
ET-7
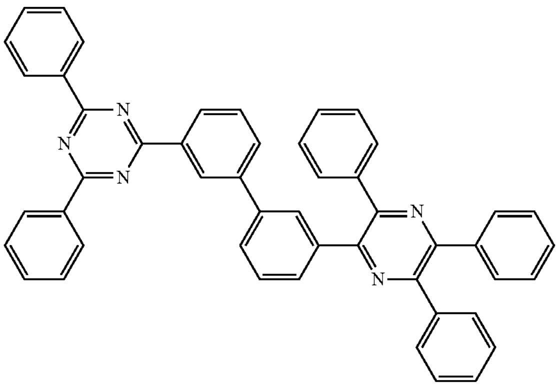
ET-8
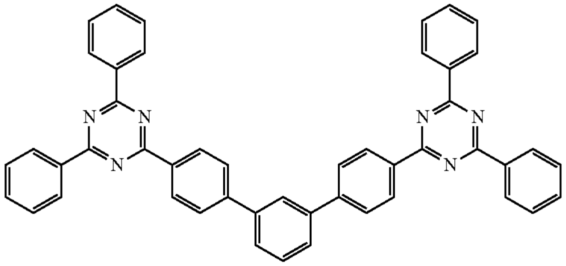

-continued
ET-9
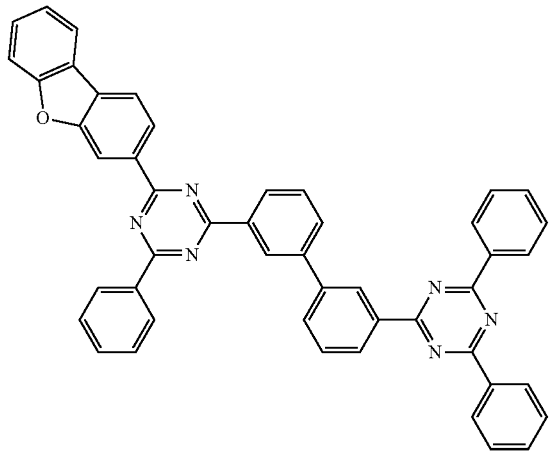
ET-10
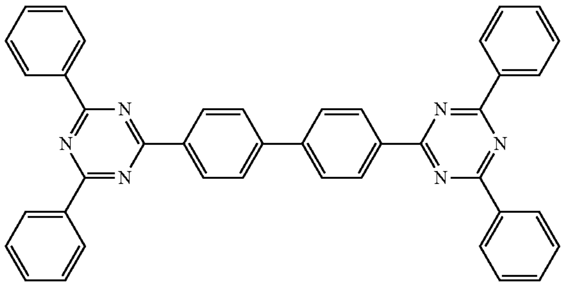
ET-11
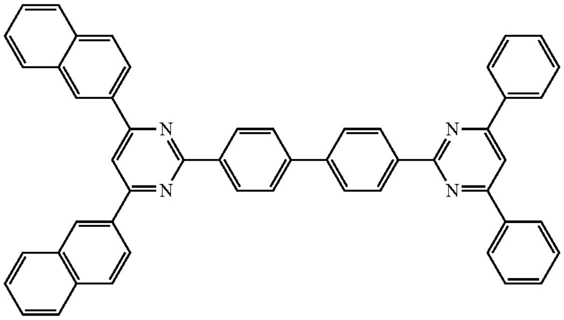
ET-12
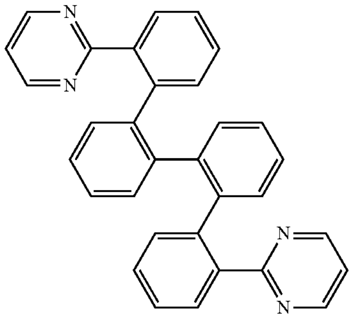
ET-13
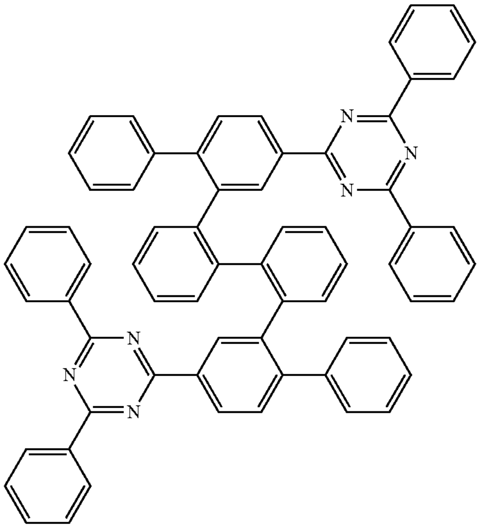
ET-14
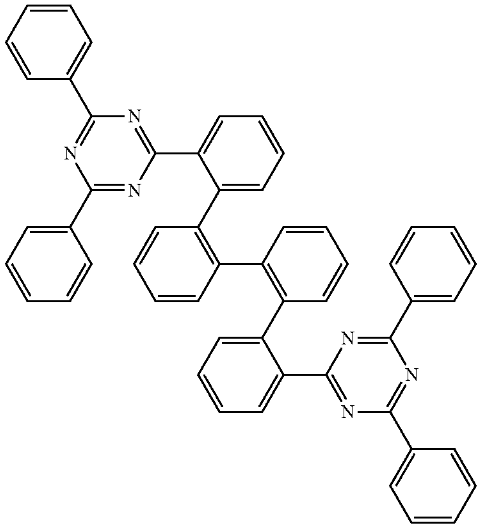

-continued
ET-15
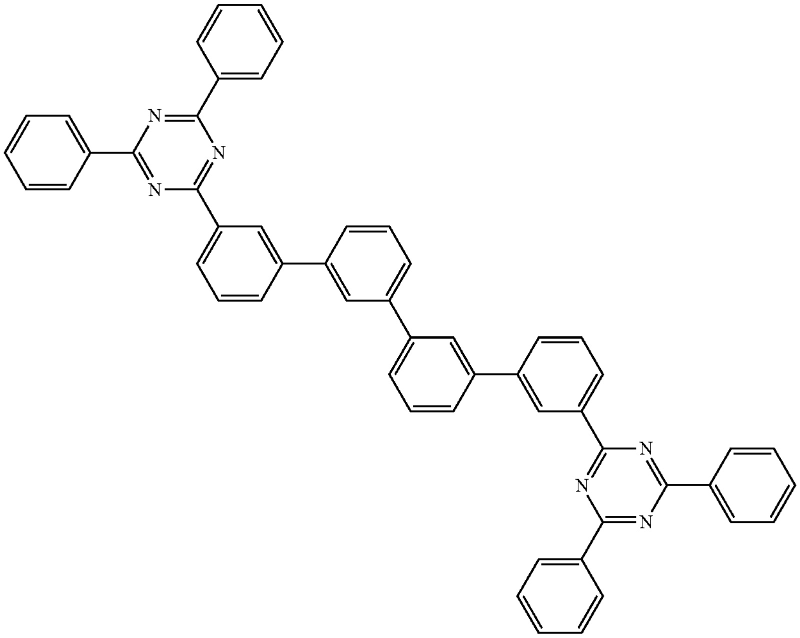
ET-16
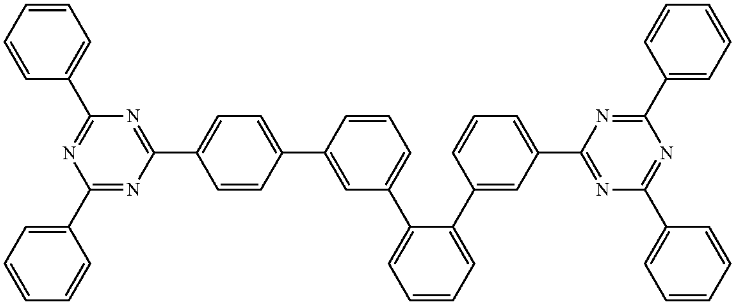
ET-17
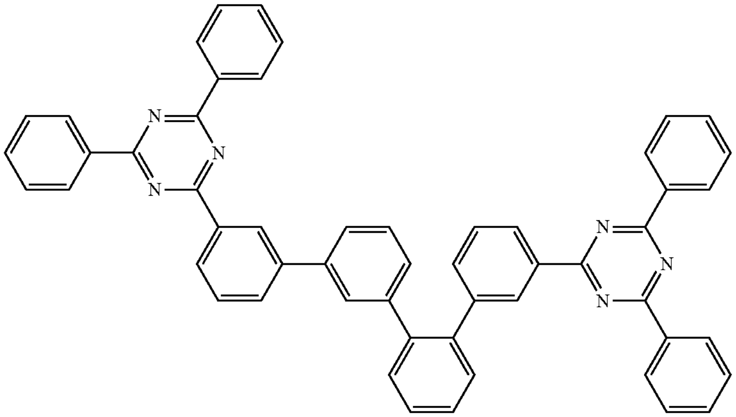

-continued

ET-18

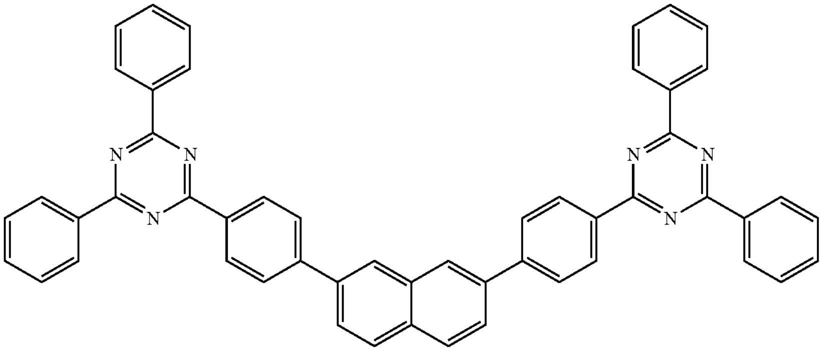

ET-19

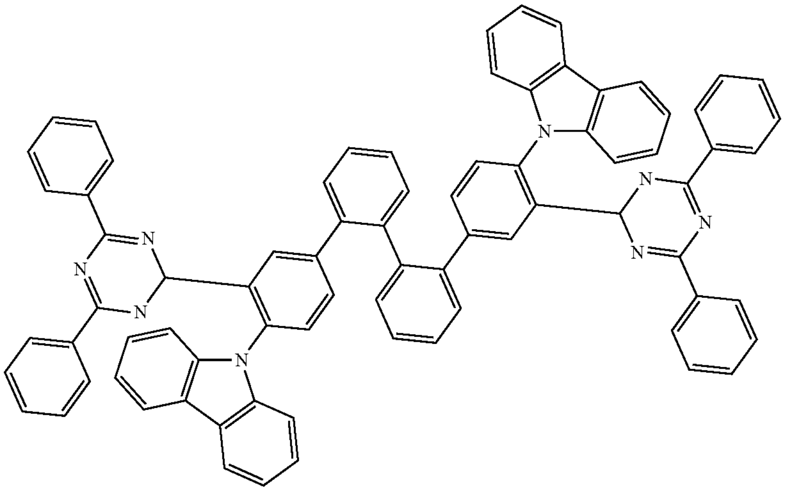

For the organic light emitting devices prepared in Experimental Examples and Comparative Experimental Examples, the driving voltage, luminous efficiency, and chromaticity coordinates were measured at a current density of 10 $mA/cm^2$. In addition, $T_{90}$, which is the time taken until the initial luminance decreases to 90% at a current density of 20 $mA/cm^2$, was measured. The results are shown in Table 1 below.

TABLE 1

| | Compound (Electron transport and injection layer) | Voltage (V@10 $mA/cm^2$) | Efficiency (cd/A@10 $mA/cm^2$) | Chromaticity coordinates (x, y) | $T_{90}$ (hr@20 $mA/cm^2$) |
|---|---|---|---|---|---|
| Experimental Example 1 | E1 | 3.62 | 4.70 | (0.133, 0.088) | 200 |
| Experimental Example 2 | E2 | 3.76 | 4.65 | (0.133, 0.088) | 184 |
| Experimental Example 3 | E3 | 3.80 | 4.56 | (0.133, 0.087) | 178 |
| Experimental Example 4 | E4 | 3.92 | 4.20 | (0.133, 0.088) | 164 |
| Experimental Example 5 | E5 | 3.99 | 4.15 | (0.135, 0.087) | 167 |
| Experimental Example 6 | E6 | 3.91 | 4.14 | (0.133, 0.088) | 160 |
| Experimental Example 7 | E7 | 3.80 | 4.61 | (0.133, 0.088) | 180 |
| Experimental Example 8 | E8 | 3.66 | 4.75 | (0.133, 0.087) | 194 |
| Experimental Example 9 | E9 | 3.69 | 4.61 | (0.133, 0.088) | 208 |
| Experimental Example 10 | E10 | 3.69 | 4.75 | (0.133, 0.088) | 188 |
| Experimental Example 11 | E11 | 3.66 | 4.65 | (0.133, 0.088) | 208 |
| Experimental Example 12 | E12 | 3.73 | 4.76 | (0.133, 0.088) | 180 |
| Experimental Example 13 | E13 | 3.77 | 4.66 | (0.133, 0.087) | 173 |
| Experimental Example 14 | E14 | 3.69 | 4.56 | (0.133, 0.088) | 220 |
| Experimental Example 15 | E15 | 3.73 | 4.57 | (0.133, 0.088) | 180 |
| Experimental Example 16 | E16 | 3.69 | 4.61 | (0.133, 0.088) | 204 |
| Experimental Example 17 | E17 | 3.67 | 4.65 | (0.133, 0.088) | 202 |
| Experimental Example 18 | E18 | 3.73 | 4.42 | (0.133, 0.087) | 188 |
| Experimental Example 19 | E19 | 3.69 | 4.61 | (0.133, 0.088) | 205 |
| Experimental Example 20 | E20 | 3.73 | 4.56 | (0.133, 0.088) | 203 |
| Comparative Experimental Example 1 | ET-1 | 4.47 | 1.66 | (0.133, 0.088) | 44 |
| Comparative Experimental Example 2 | ET-2 | 4.38 | 1.65 | (0.133, 0.087) | 42 |

TABLE 1-continued

| | Compound (Electron transport and injection layer) | Voltage (V@10 mA/cm$^2$) | Efficiency (cd/A@10 mA/cm$^2$) | Chromaticity coordinates (x, y) | $T_{90}$ (hr@20 mA/cm$^2$) |
|---|---|---|---|---|---|
| Comparative Experimental Example 3 | ET-3 | 4.05 | 1.88 | (0.133, 0.088) | 52 |
| Comparative Experimental Example 4 | ET-4 | 4.09 | 1.86 | (0.135, 0.087) | 51 |
| Comparative Experimental Example 5 | ET-5 | 4.01 | 2.26 | (0.133, 0.088) | 122 |
| Comparative Experimental Example 6 | ET-6 | 4.18 | 1.82 | (0.133, 0.088) | 78 |
| Comparative Experimental Example 7 | ET-7 | 4.22 | 1.81 | (0.133, 0.087) | 76 |
| Comparative Experimental Example 8 | ET-8 | 4.02 | 2.35 | (0.133, 0.088) | 140 |
| Comparative Experimental Example 9 | ET-9 | 4.30 | 1.79 | (0.135, 0.087) | 75 |
| Comparative Experimental Example 10 | ET-10 | 4.43 | 1.73 | (0.133, 0.088) | 147 |
| Comparative Experimental Example 11 | ET-11 | 4.69 | 1.72 | (0.133, 0.088) | 110 |
| Comparative Experimental Example 12 | ET-12 | 4.70 | 1.36 | (0.133, 0.087) | 32 |
| Comparative Experimental Example 13 | ET-13 | 4.23 | 3.32 | (0.133, 0.088) | 129 |
| Comparative Experimental Example 14 | ET-14 | 4.19 | 3.36 | (0.133, 0.088) | 116 |
| Comparative Experimental Example 15 | ET-15 | 4.44 | 3.26 | (0.133, 0.088) | 131 |
| Comparative Experimental Example 16 | ET-16 | 4.49 | 3.19 | (0.133, 0.087) | 132 |
| Comparative Experimental Example 17 | ET-17 | 4.53 | 3.09 | (0.133, 0.088) | 136 |
| Comparative Experimental Example 18 | ET-18 | 4.40 | 3.13 | (0.133, 0.088) | 135 |
| Comparative Experimental Example 19 | ET-19 | 4.42 | 1.81 | (0.133, 0.088) | 100 |

As shown in Table 1, the compound of Chemical Formula 1 or 2 of the present disclosure can be used in an organic material layer capable of simultaneously performing electron transport and electron injection of an organic light emitting device.

When comparing Experimental Examples 1 to 20 and Comparative Experimental Examples 1 to 11 of Table 1, it was confirmed that the organic light emitting device including the heterocyclic compound of Chemical Formula 1 or 2 of the present disclosure had significantly superior efficiency and lifespan than the organic light emitting device including a compound in which a phenyl group less than quaterphenyl is substituted between $Ar_1$ and $Ar_2$.

When comparing Experimental Examples 1 to 20 and Comparative Experimental Examples 12 to 17 of Table 1, it was confirmed that the organic light emitting device including the heterocyclic compound of Chemical Formula 1 or 2 of the present disclosure had significantly superior efficiency and lifespan than the organic light emitting device including a compound in which quaterphenyl is substituted at a different substitution position from the present disclosure.

When comparing Experimental Examples 1 to 20 and Comparative Experimental Example 18 of Table 1, it was confirmed that the organic light emitting device including the heterocyclic compound of Chemical Formula 1 or 2 of the present disclosure had significantly superior efficiency and lifespan than the organic light emitting device including a compound in which naphthalene is substituted between $Ar_1$ and $Ar_2$.

When comparing Experimental Examples 1 to 20 and Comparative Experimental Example 19 of Table 1, it was confirmed that the organic light emitting device including the heterocyclic compound of Chemical Formula 1 or 2 of the present disclosure had significantly superior efficiency and lifespan than the organic light emitting device including a compound in which heteroaryl is additionally substituted to quaterphenylene.

[DESCRIPTION OF SYMBOLS]

| | |
|---|---|
| 1: Substrate | 2: Anode |
| 3: Light emitting layer | 4: Cathode |
| 5: Hole injection layer | 6: Hole transport layer |
| 7: Light emitting layer | 8: Electron transport and injection layer |
| 9: Electron blocking layer | 10: Hole blocking layer |

The invention claimed is:

1. A compound of Chemical Formula 1 or 2:

[Chemical Formula 1]

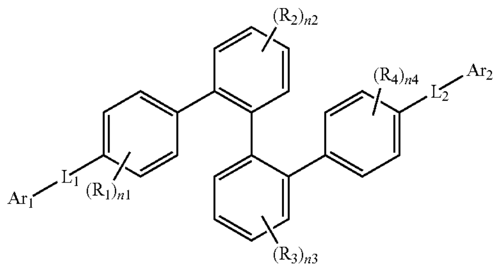

-continued

[Chemical Formula 2]

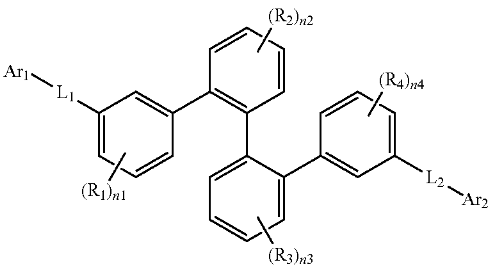

wherein in Chemical Formula 1 or 2:

$R_1$ to $R_4$ are each independently hydrogen or deuterium;

n1 to n4 are an integer of 1 to 4;

$L_1$ and $L_2$ are each independently a direct bond or a substituted or unsubstituted $C_{6-60}$ arylene; and $Ar_1$ and $Ar_2$ are each independently a substituent of Chemical Formula 3,

[Chemical Formula 3]

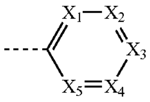

wherein in Chemical Formula 3:

$X_1$ to $X_5$ are each independently N or $C(R_5)$, wherein at least two of $X_1$ to $X_5$ are N; and each $R_5$ is independently hydrogen, deuterium, a substituted or unsubstituted $C_{1-20}$ alkyl, a substituted or unsubstituted $C_{6-60}$ aryl, or a substituted or unsubstituted $C_{2-60}$ heteroaryl containing at least one heteroatom selected from the group consisting of N, O and S, or two adjacent $R_5$s are combined to form a benzene ring.

2. The compound of claim 1, wherein Chemical Formula 1 is the following Chemical Formula 1-1, and Chemical Formula 2 is the following Chemical Formula 2-1:

[Chemical Formula 1-1]

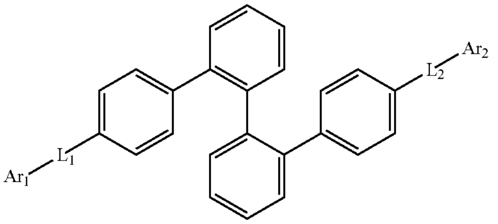

[Chemical Formula 2-1]

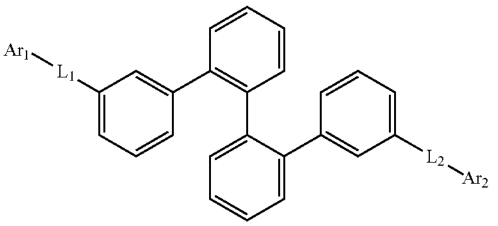

wherein in the Chemical Formula 1-1 or 2-1, $L_1$, $L_2$, $Ar_1$ and $Ar_2$ are as defined in claim 1.

3. The compound of claim 1, wherein $L_1$ and $L_2$ are each independently a direct bond, phenylene, or biphenyldiyl.

4. The compound of claim 1, wherein $Ar_1$ and $Ar_2$ are each independently any one selected from the group consisting of:

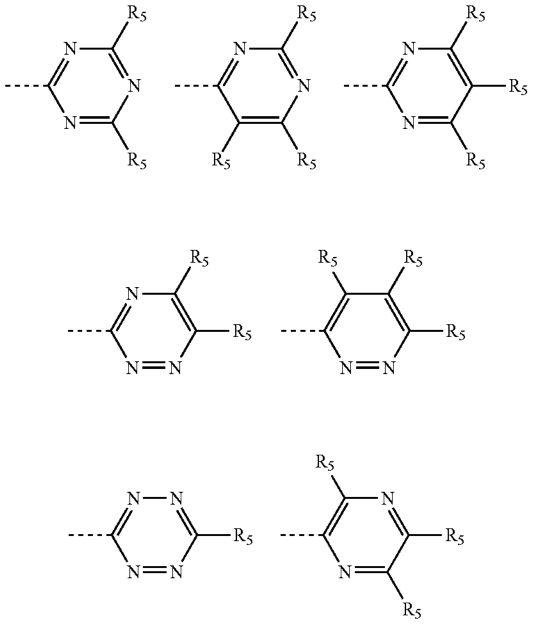

wherein in the above group, $R_5$ is as defined in claim 1.

5. The compound of claim 1, wherein;

each $R_5$ is independently hydrogen, deuterium, methyl, tert-butyl, phenyl, biphenylyl, terphenylyl, naphthyl, pyridinyl, furanyl, or thiophenyl, or two adjacent $R_5$s are combined to form a benzene ring; and the phenyl, biphenylyl, terphenylyl, naphthyl, pyridinyl, furanyl, or thiophenyl is each independently unsubstituted or substituted with deuterium, methyl, or tert-butyl.

6. The compound of claim 1, wherein $Ar_1$ and $Ar_2$ are each independently any one selected from the group consisting of:

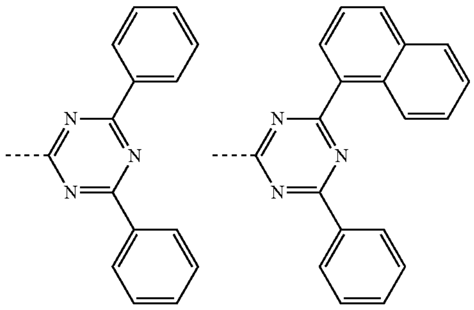

-continued
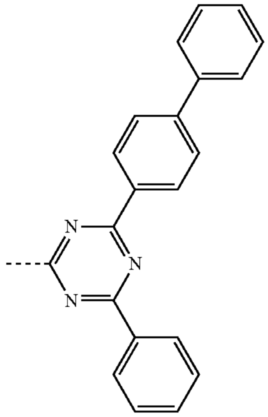
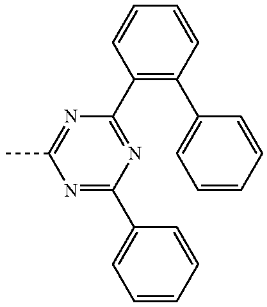
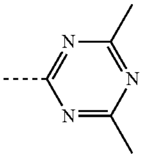
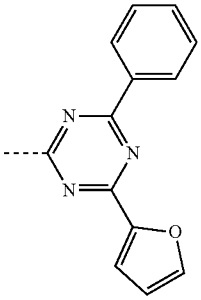
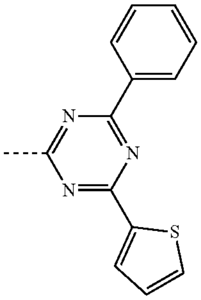
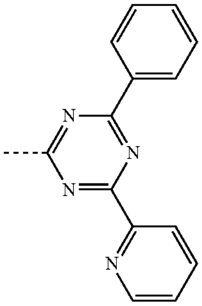
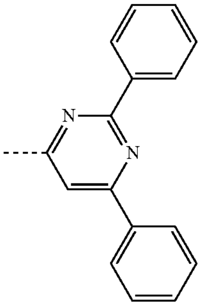
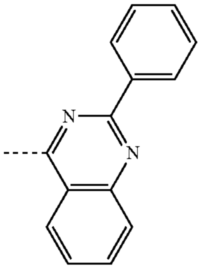
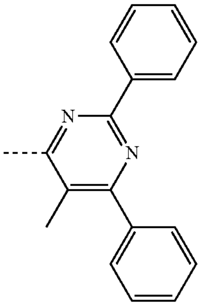
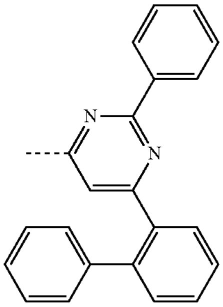
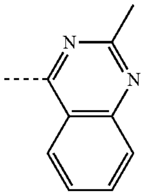
-continued
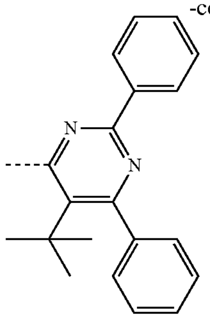
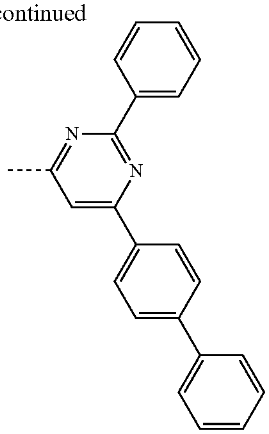
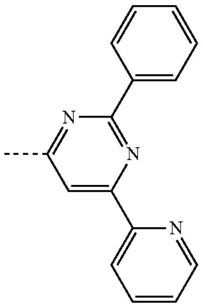
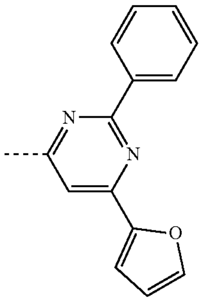
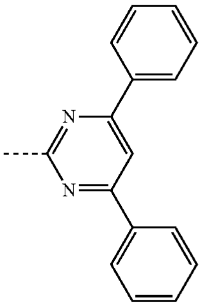
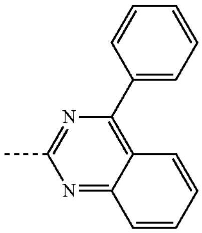
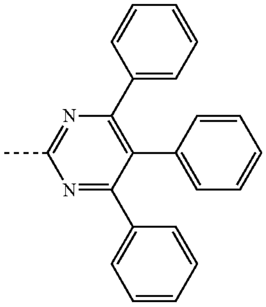
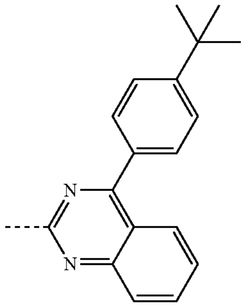
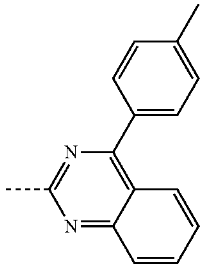
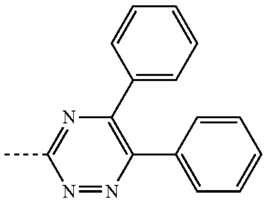

-continued
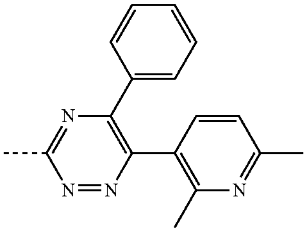
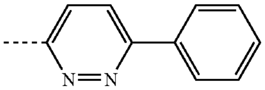
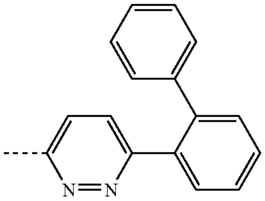
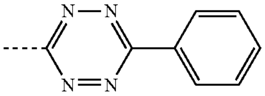
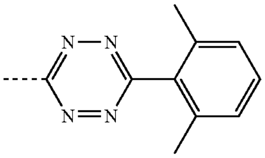
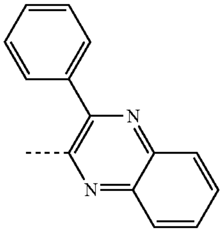
-continued
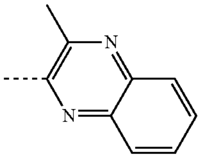
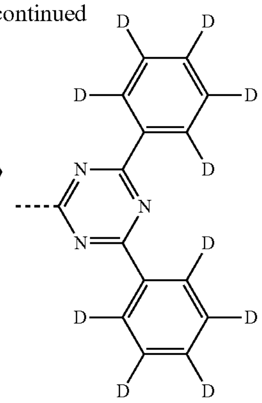
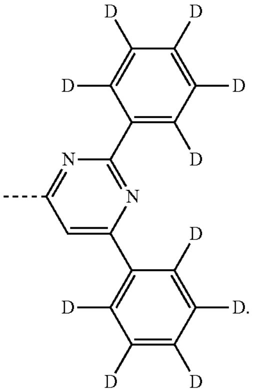
7. The compound of claim 1, wherein the compound of Chemical Formula 1 or 2 is any one compound selected from the group consisting of the following compounds:
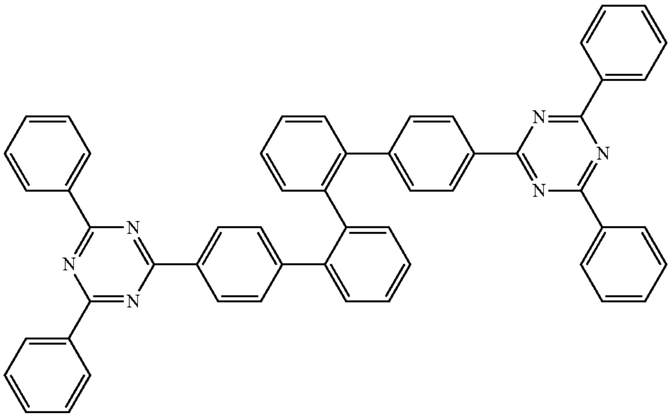

-continued
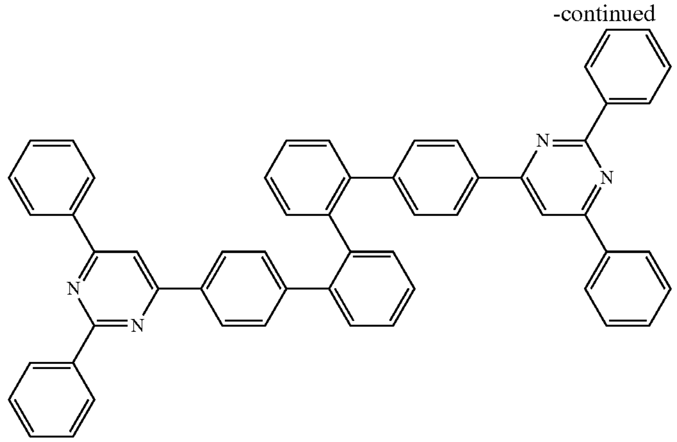
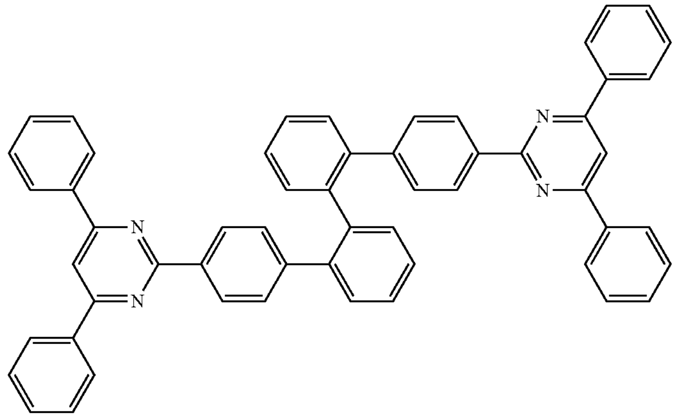
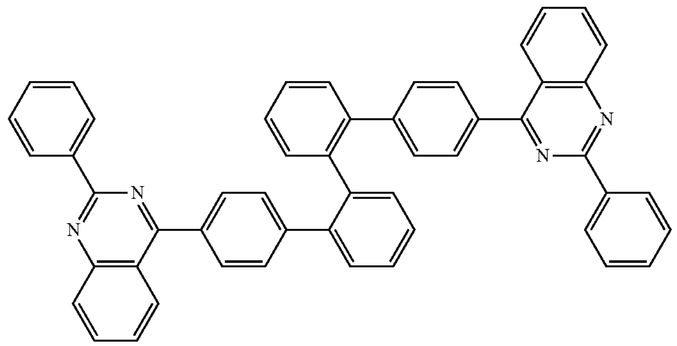
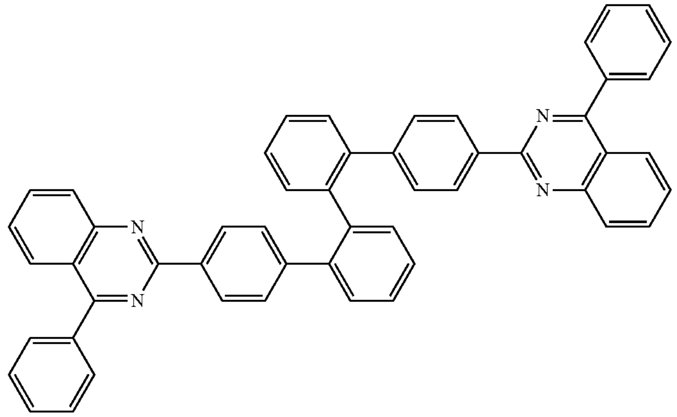

-continued
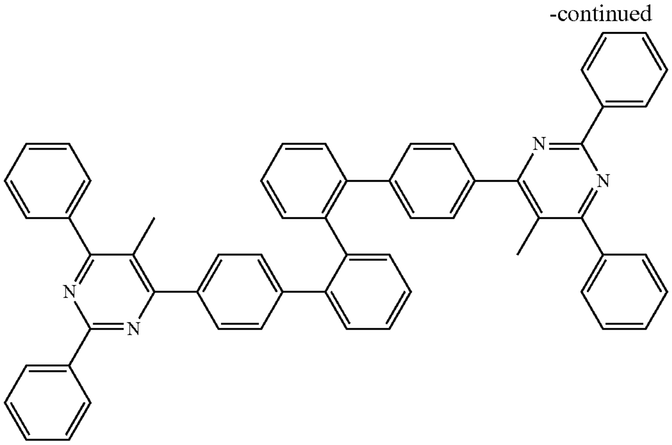
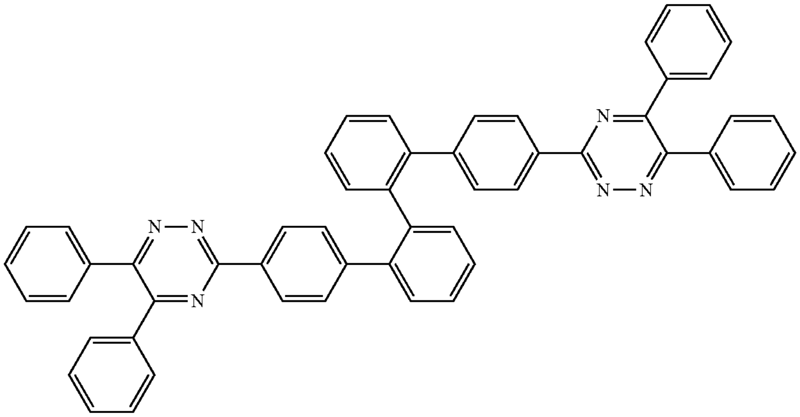
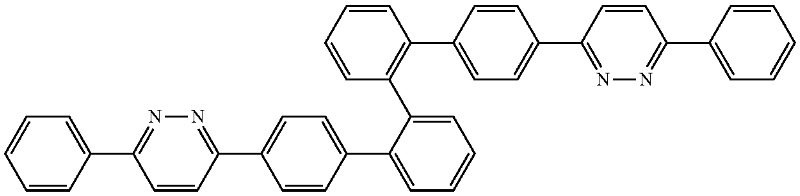
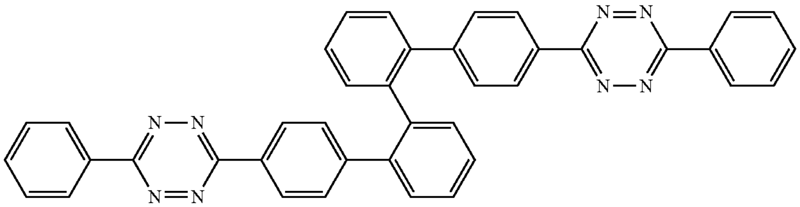
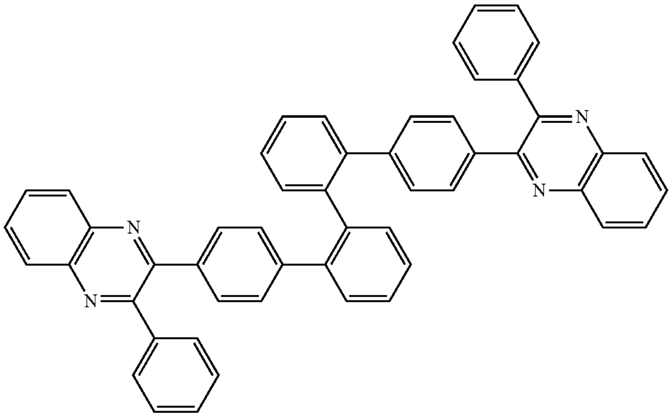

-continued
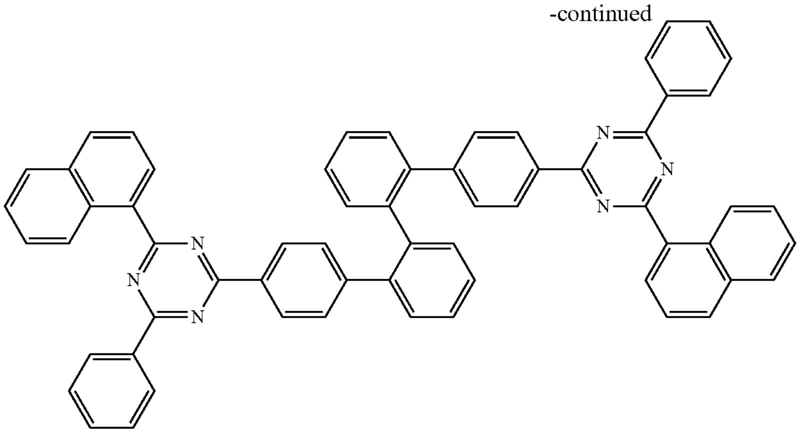
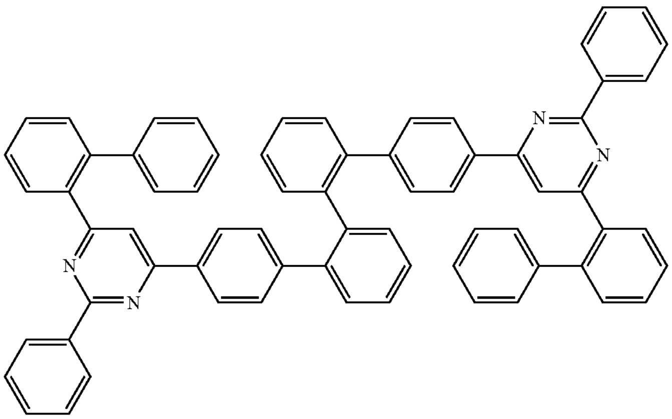
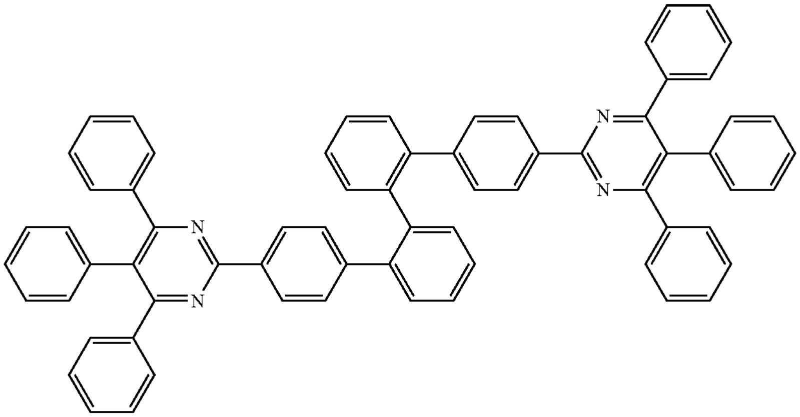
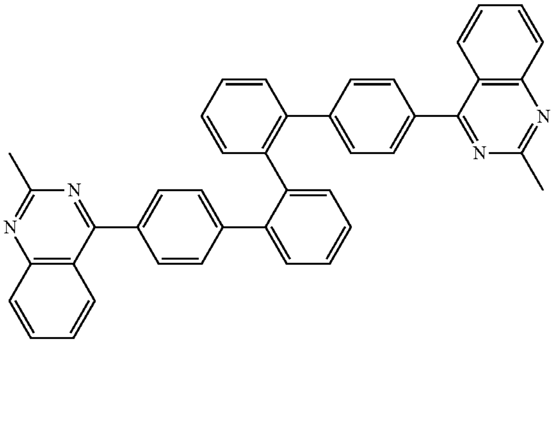

-continued
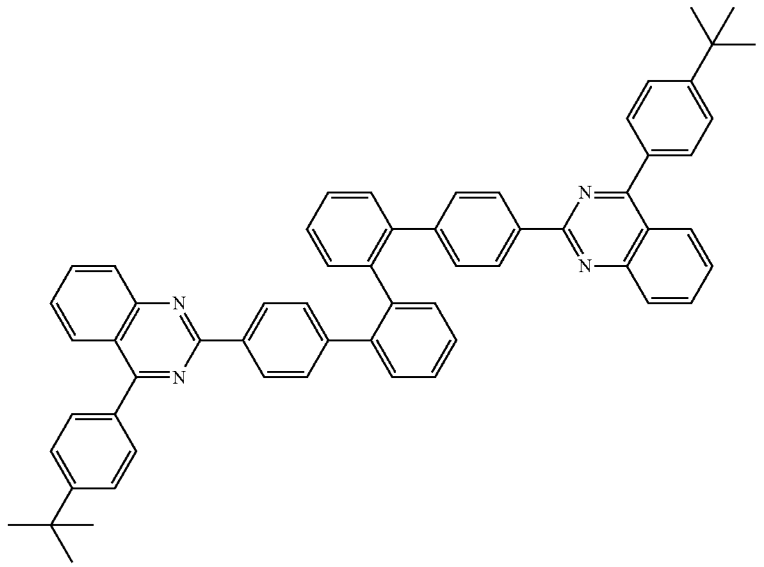
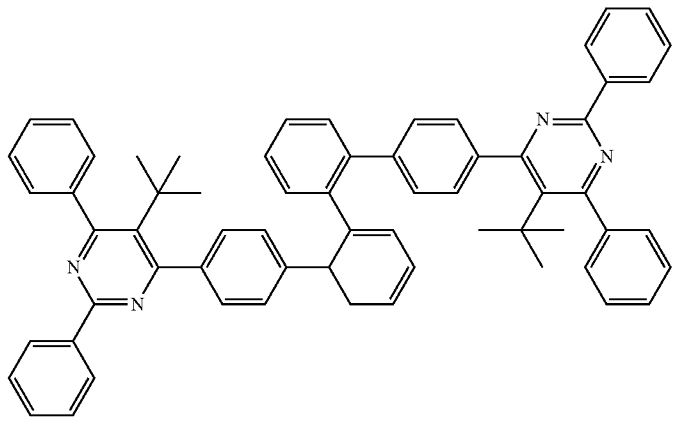
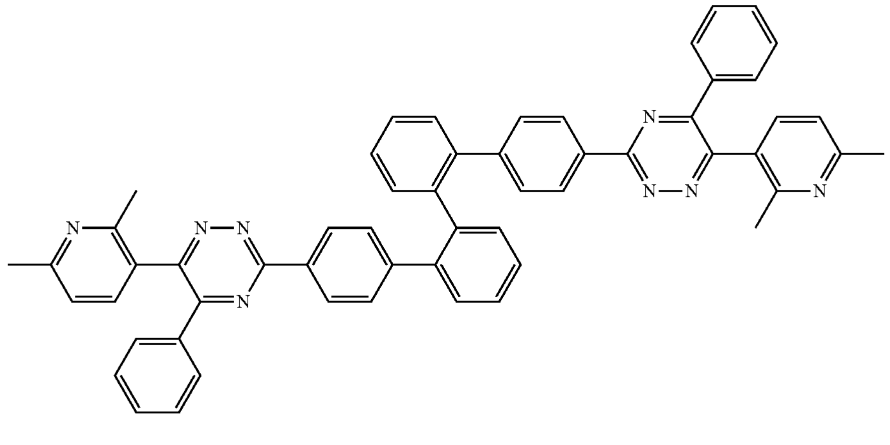

-continued
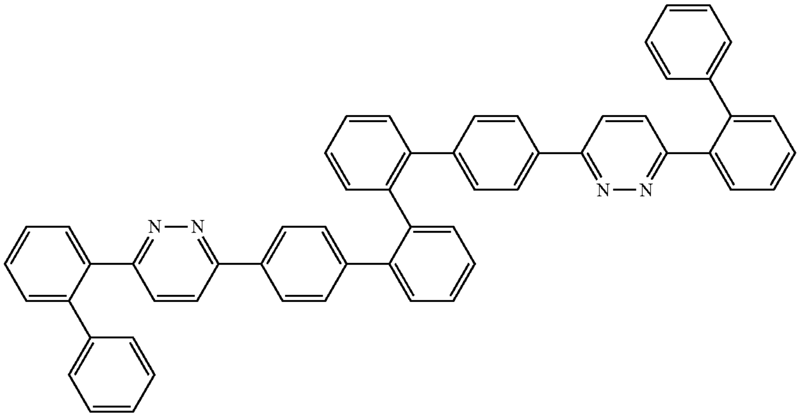
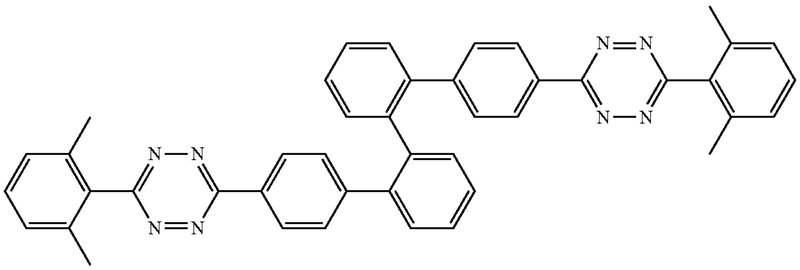
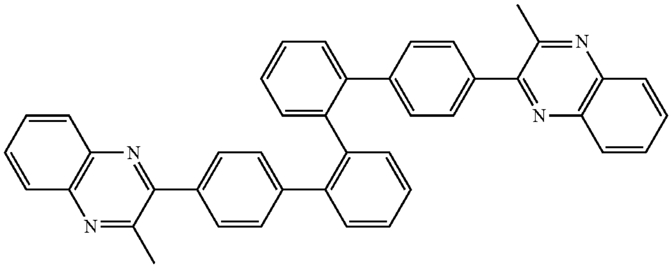
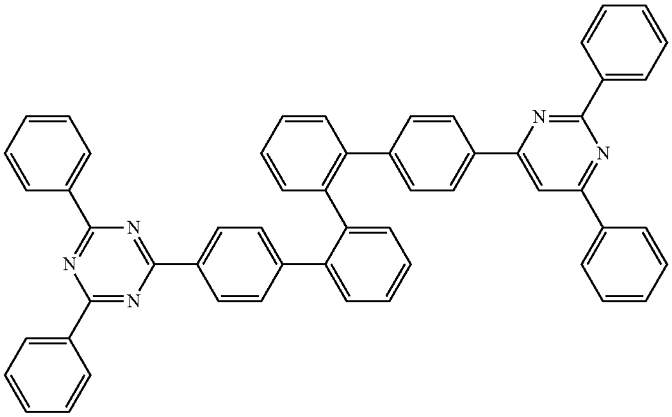

-continued
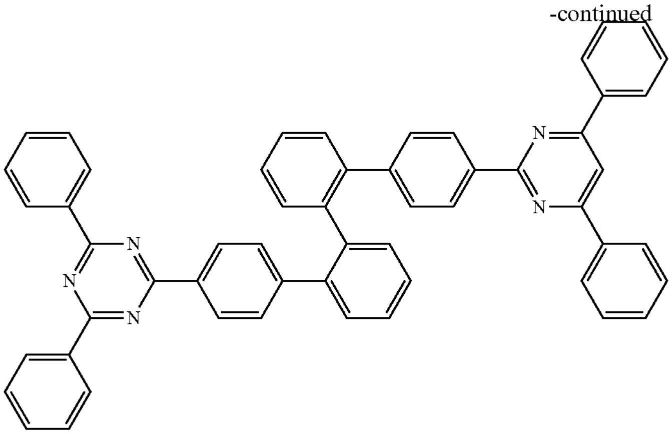
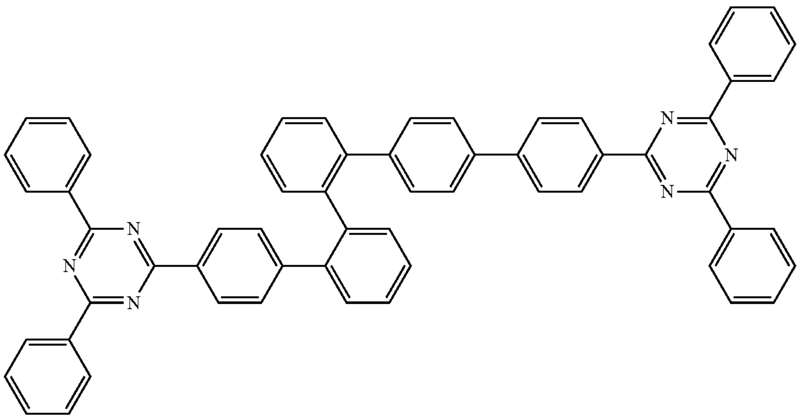
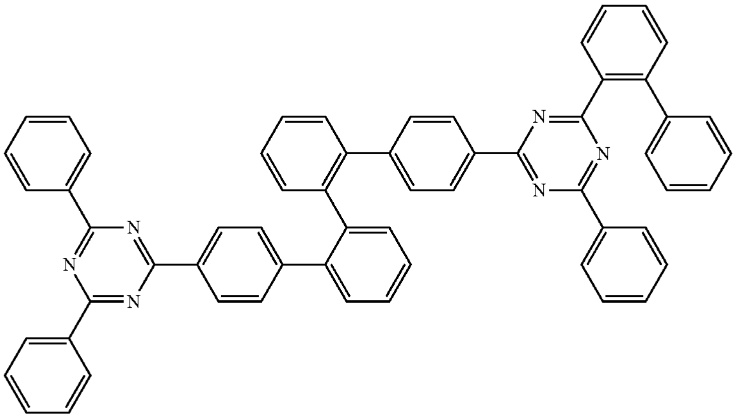
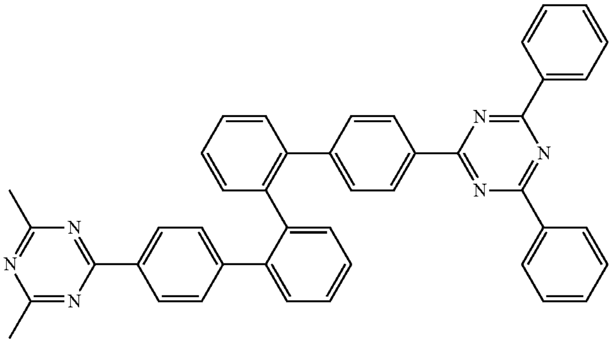

-continued
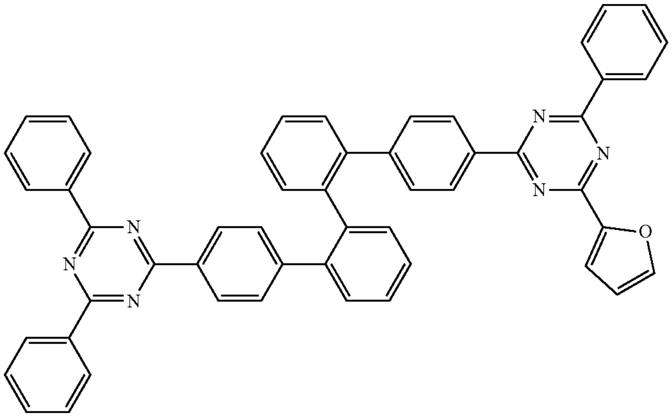
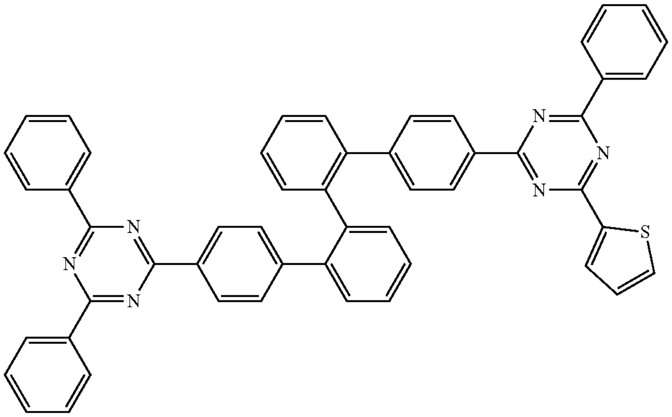
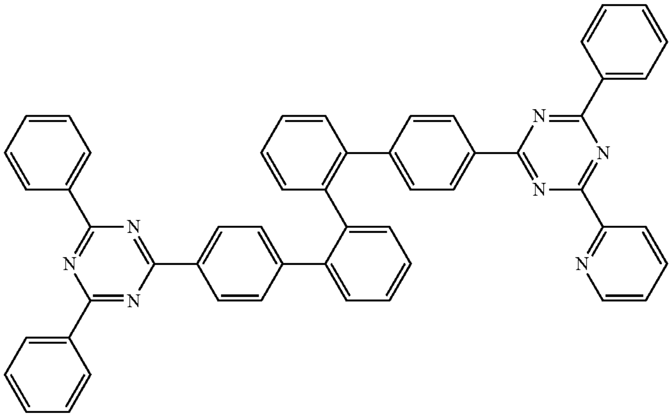
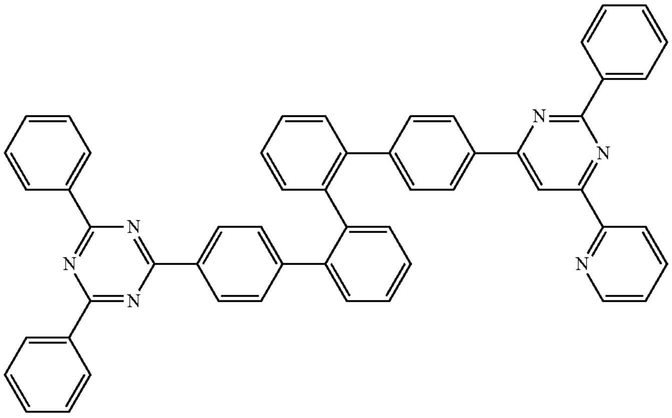

-continued
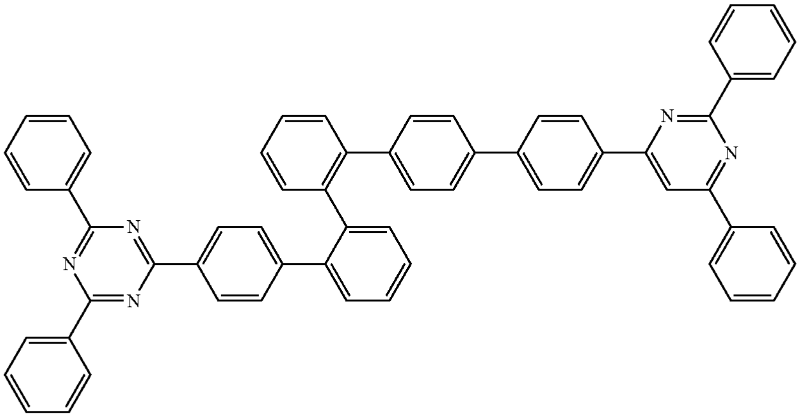
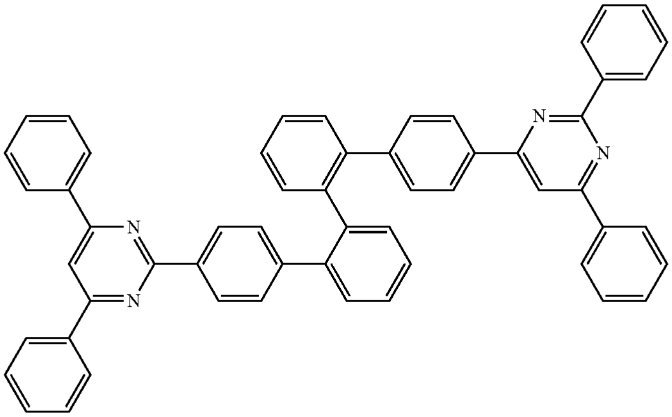
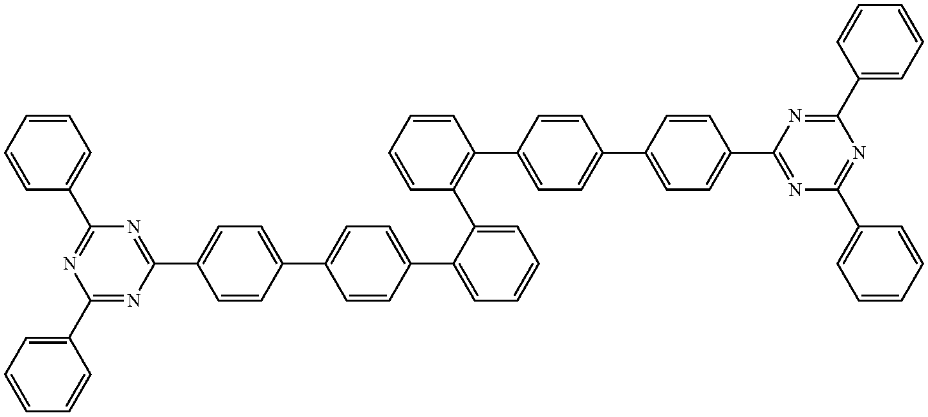
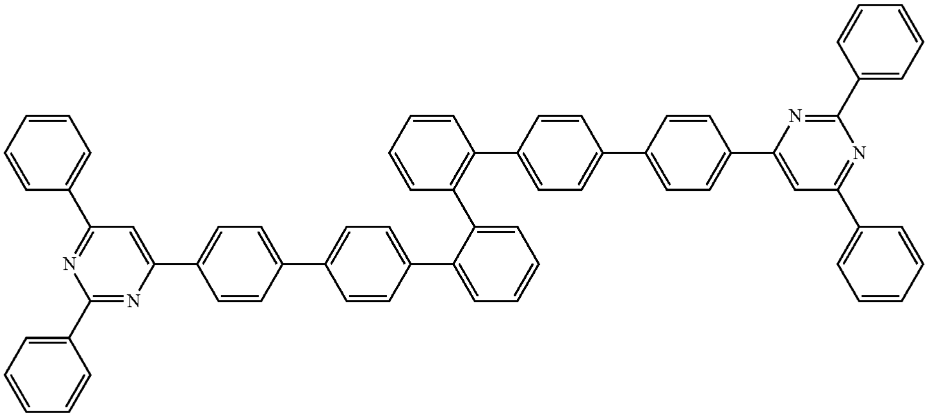

-continued
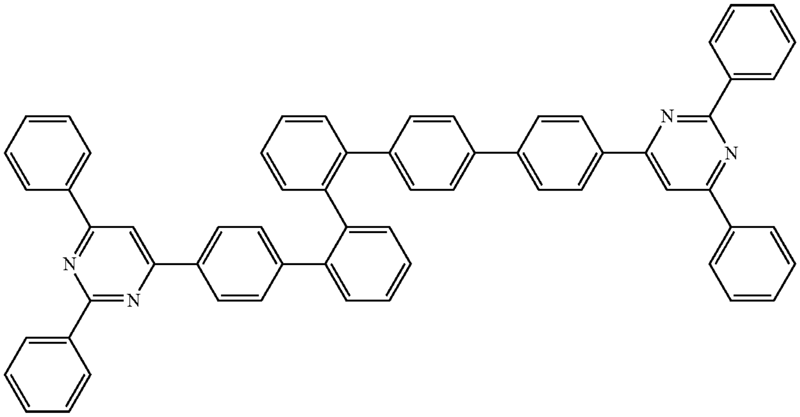
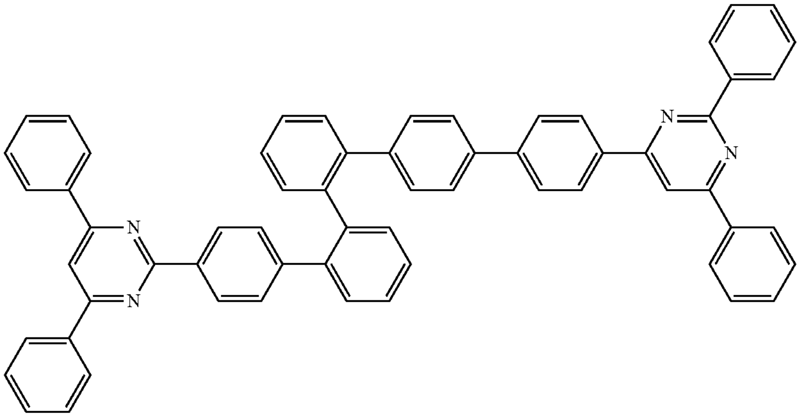
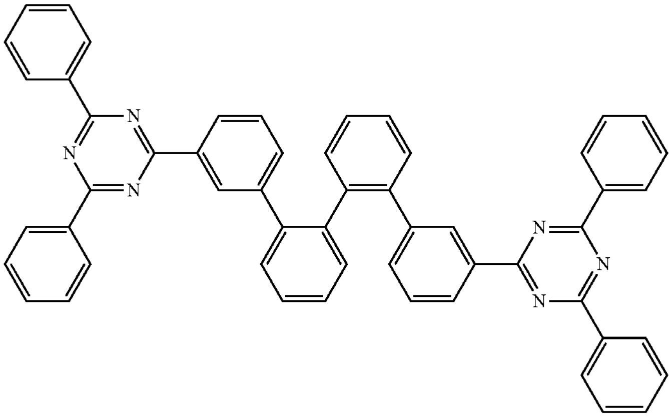
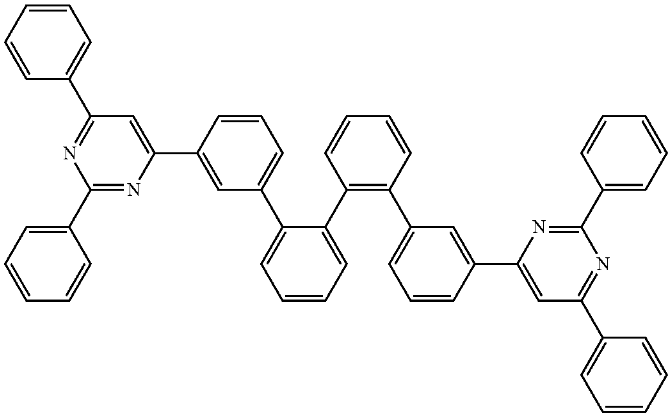

-continued
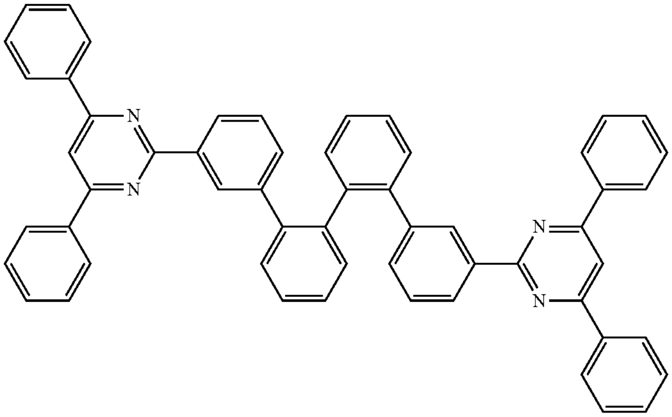
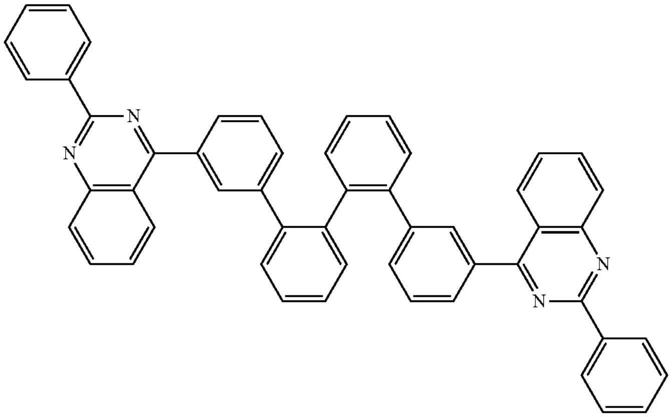
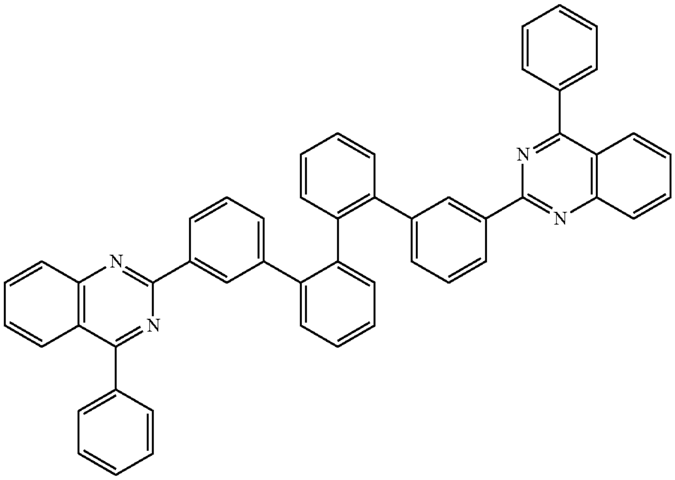
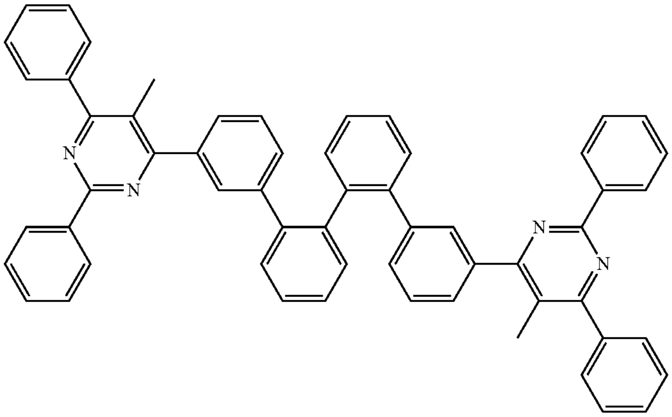

-continued
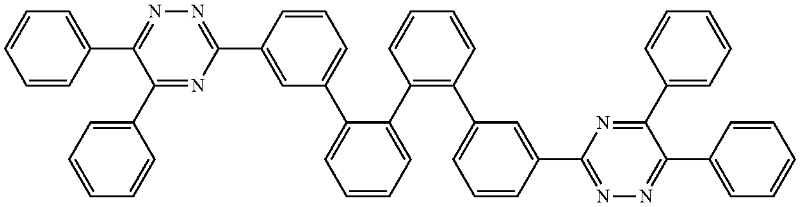
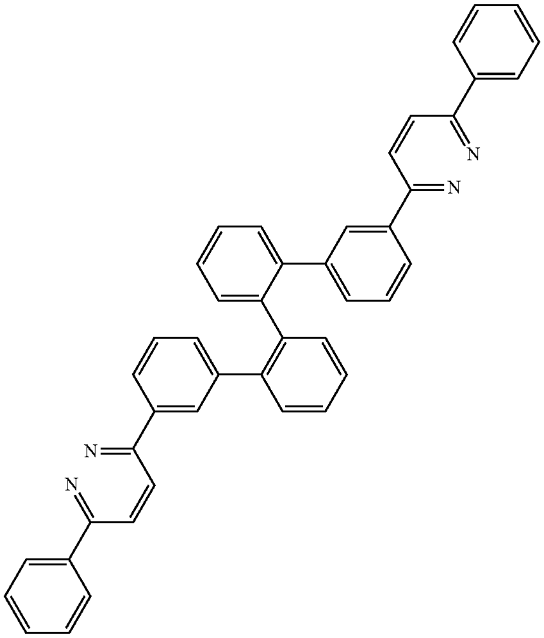
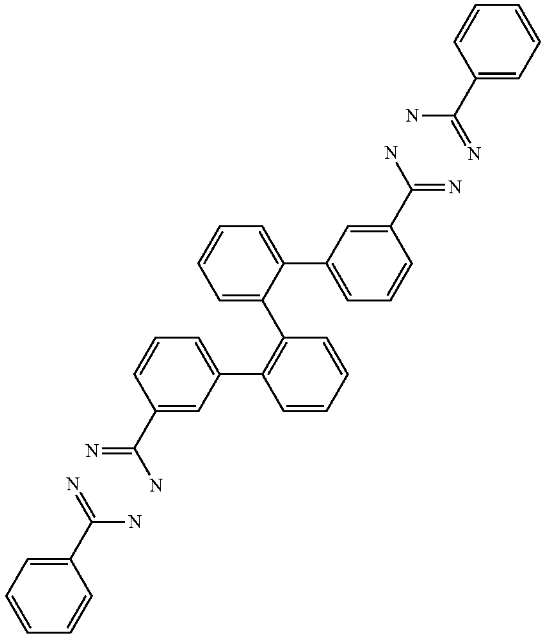
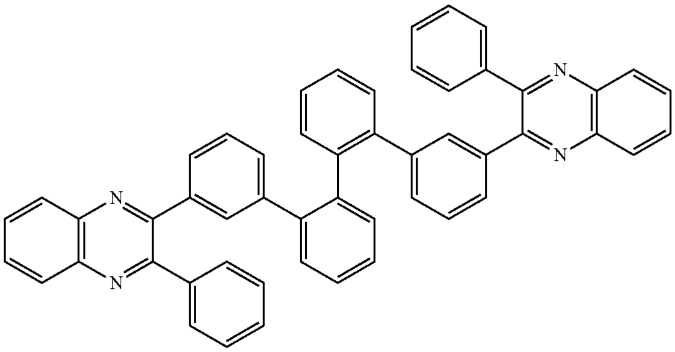

-continued
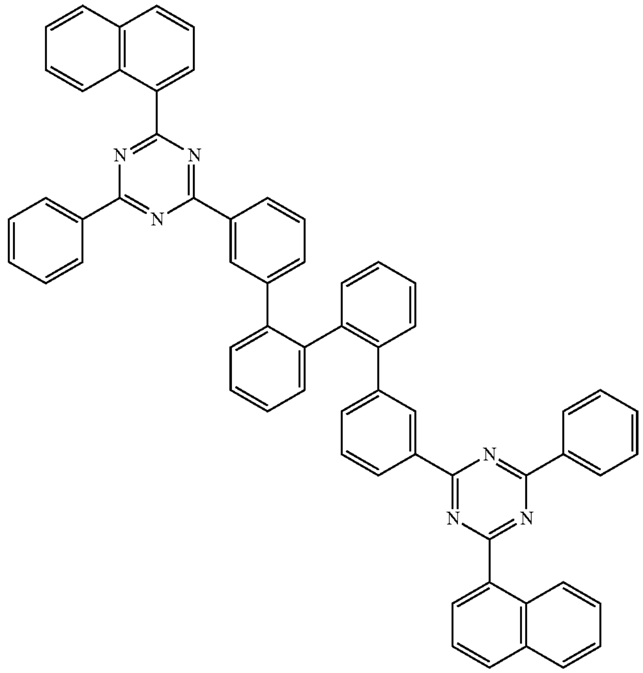
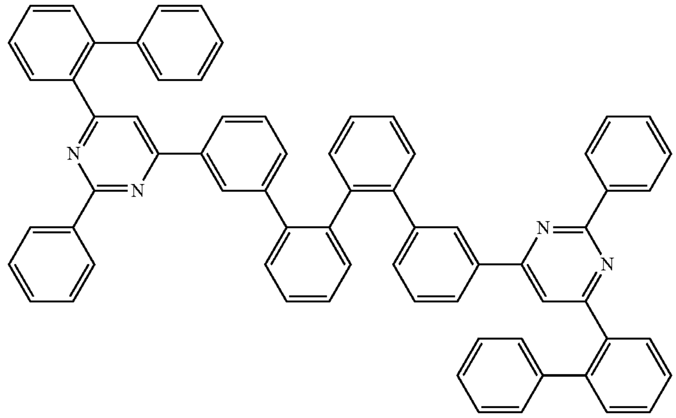
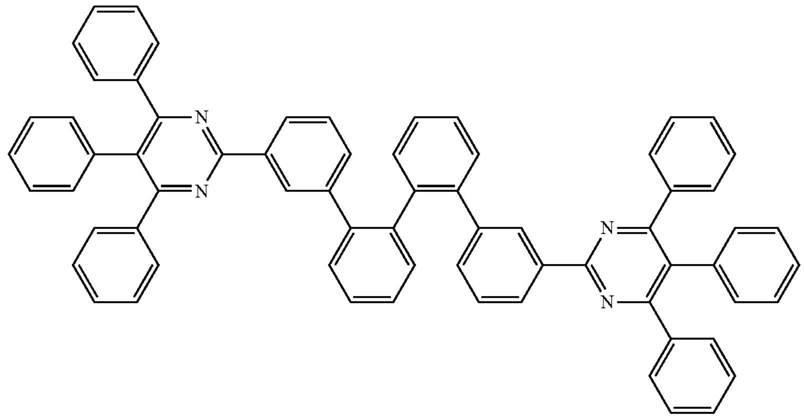

-continued
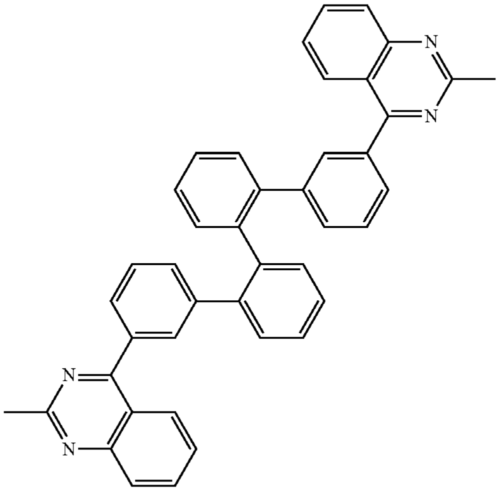
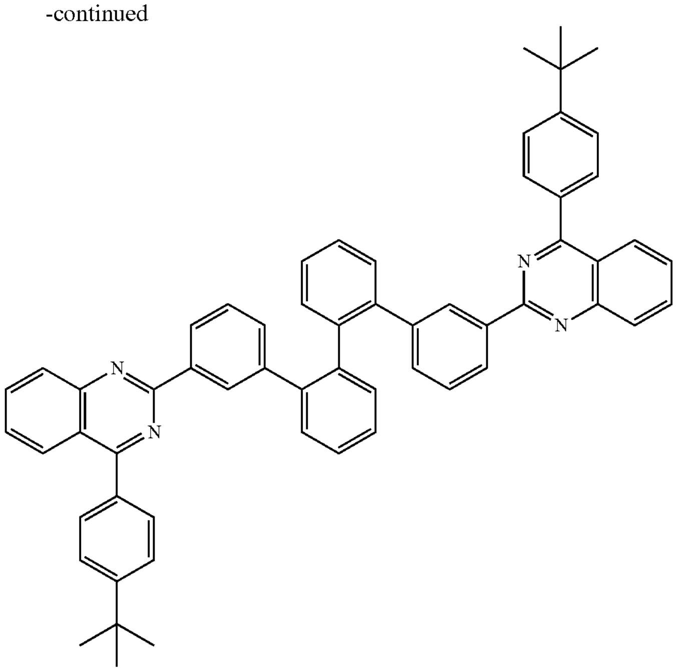
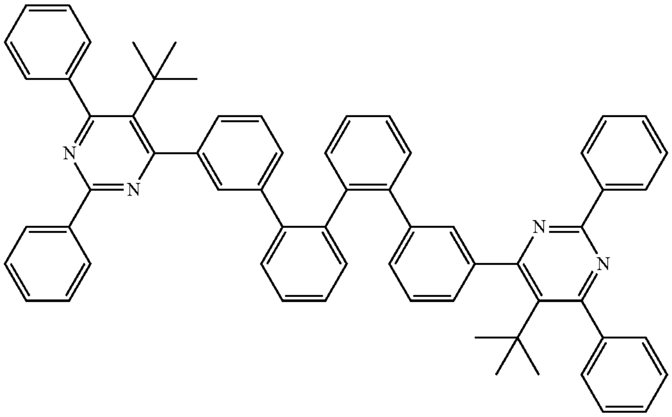
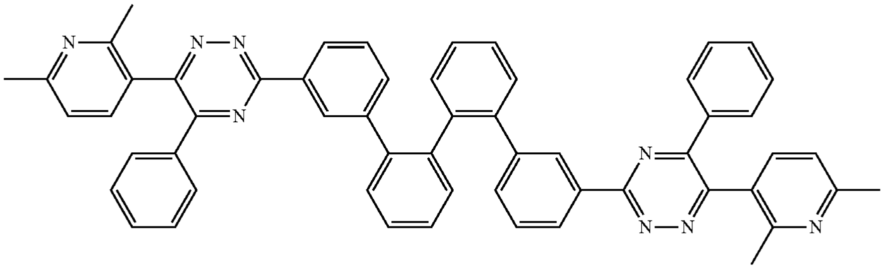
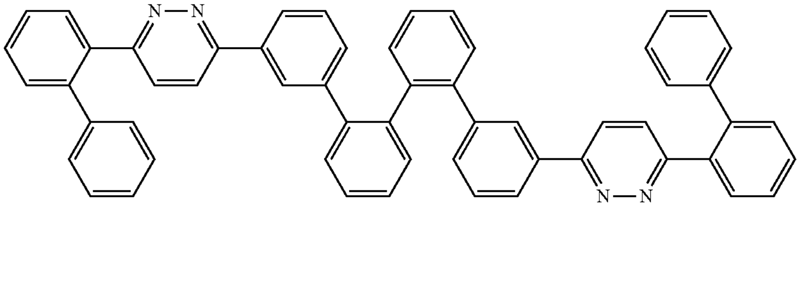

-continued
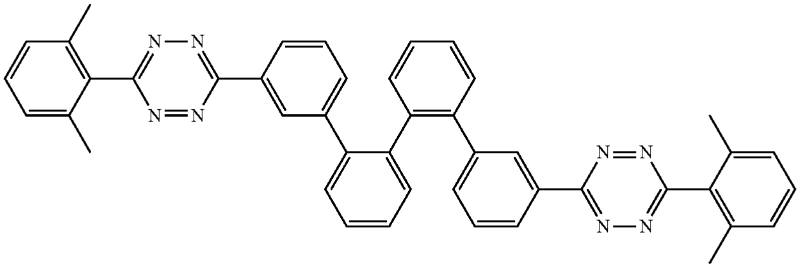
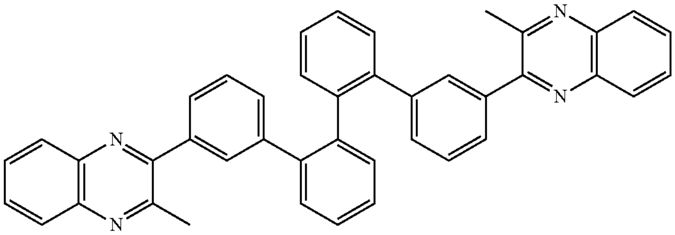
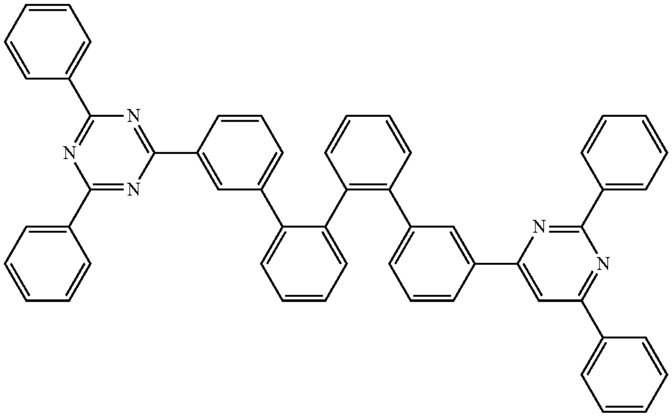
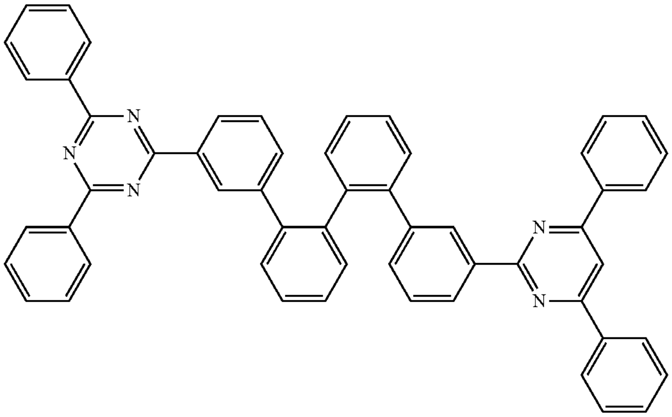

-continued
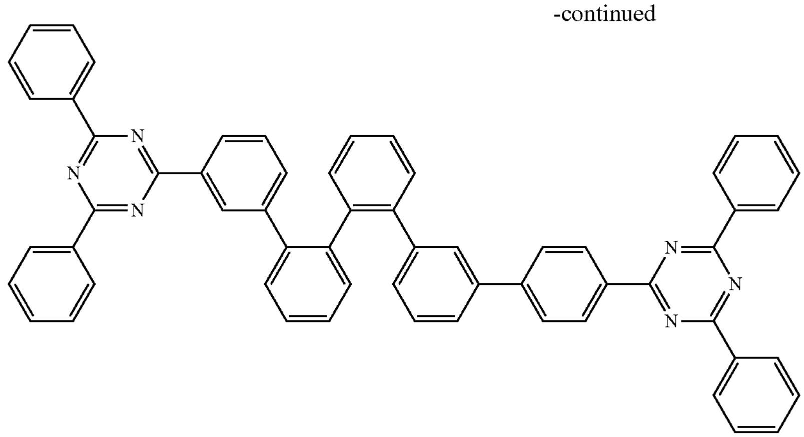
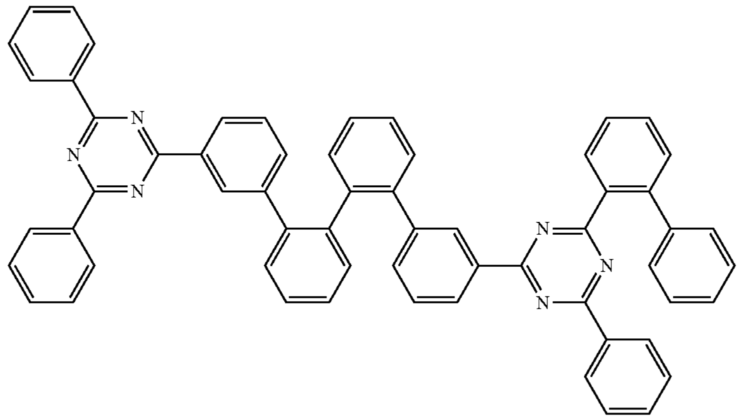
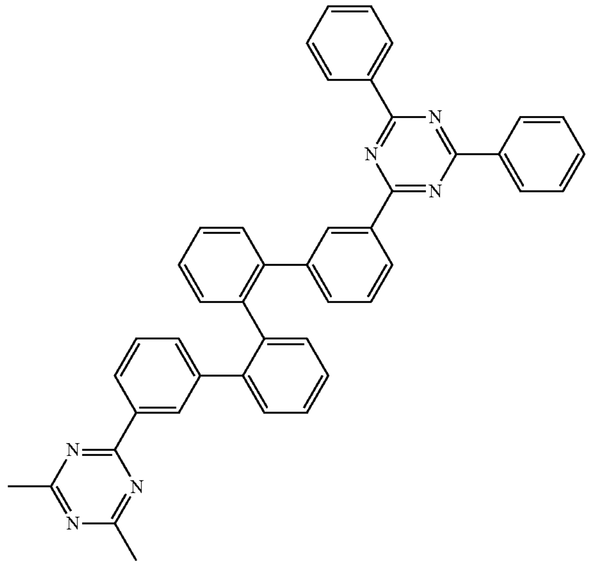

-continued
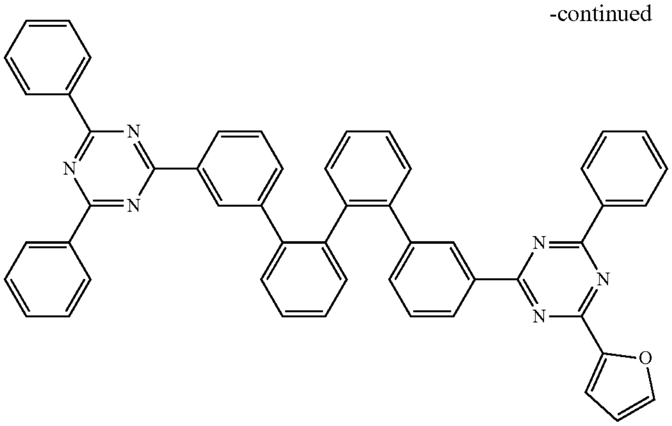
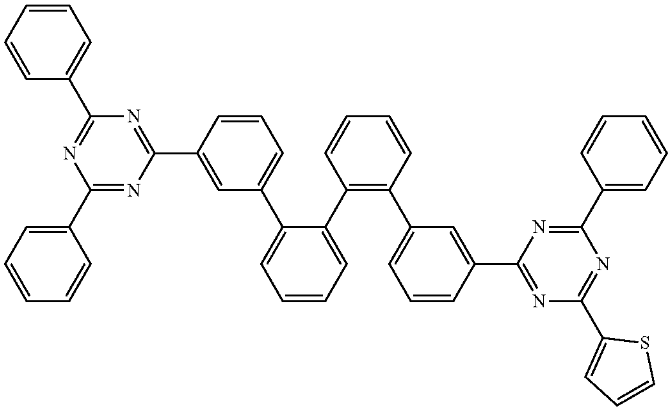
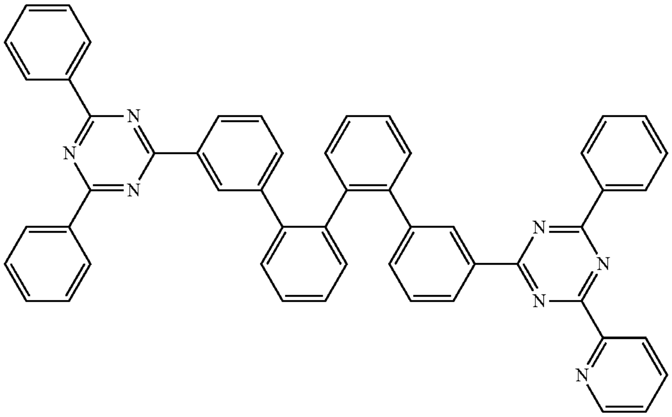
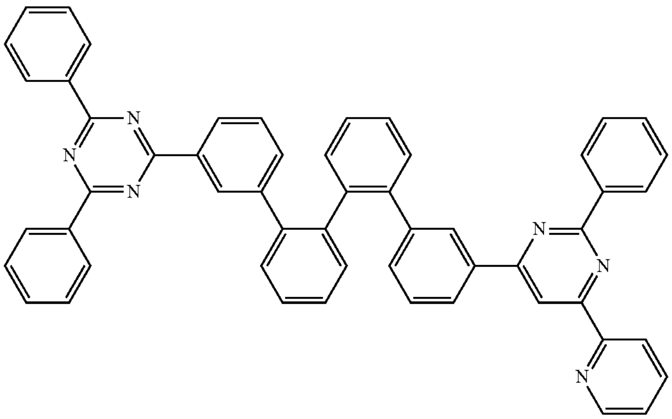

-continued
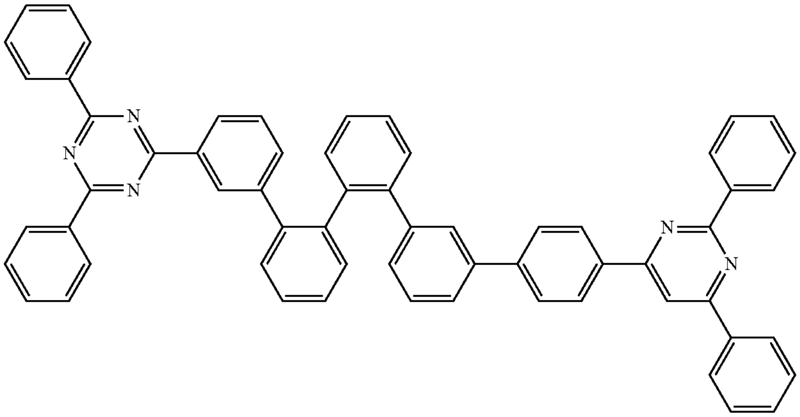
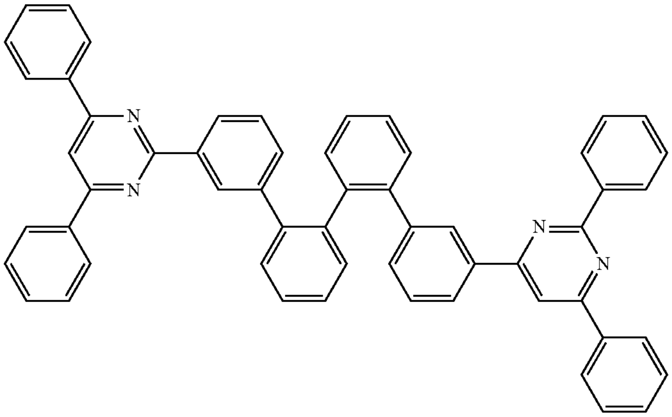
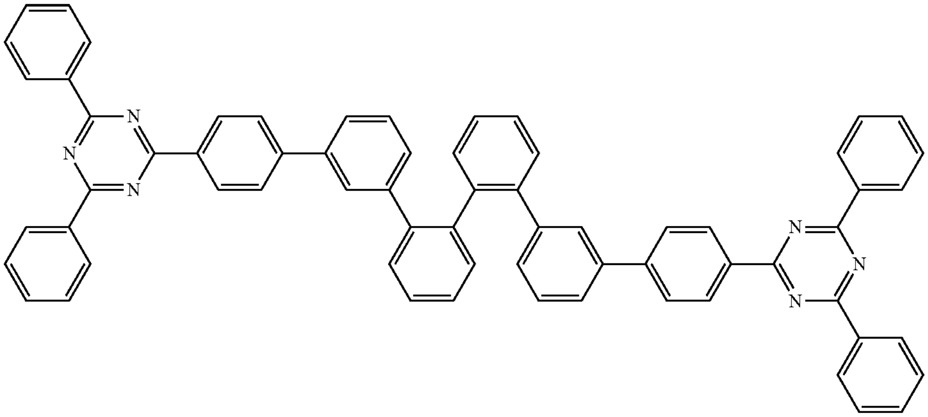
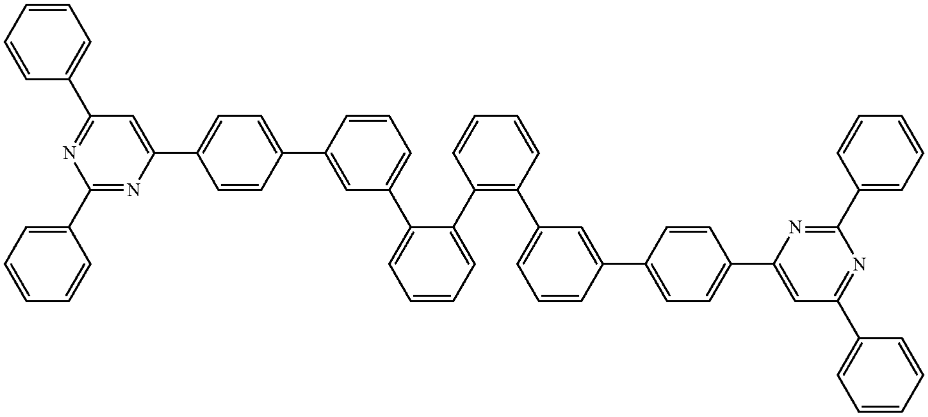

-continued
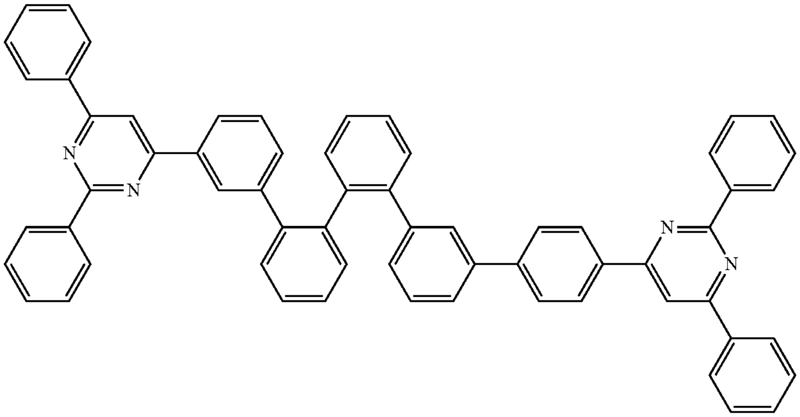
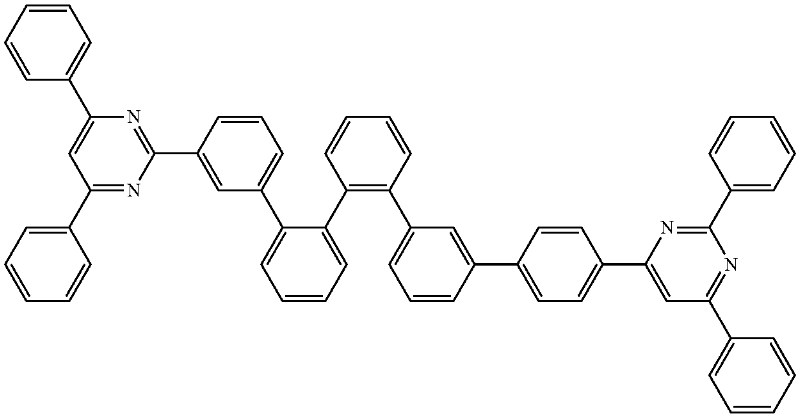
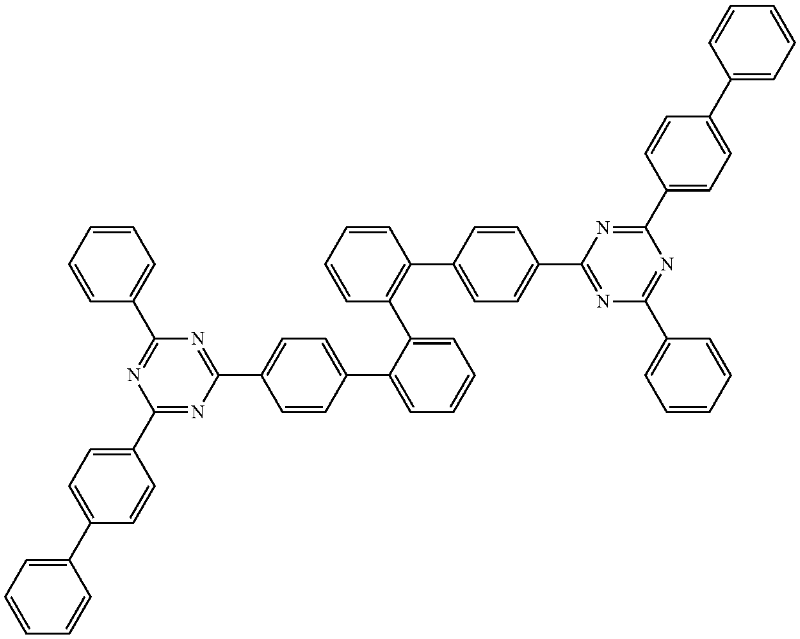

-continued
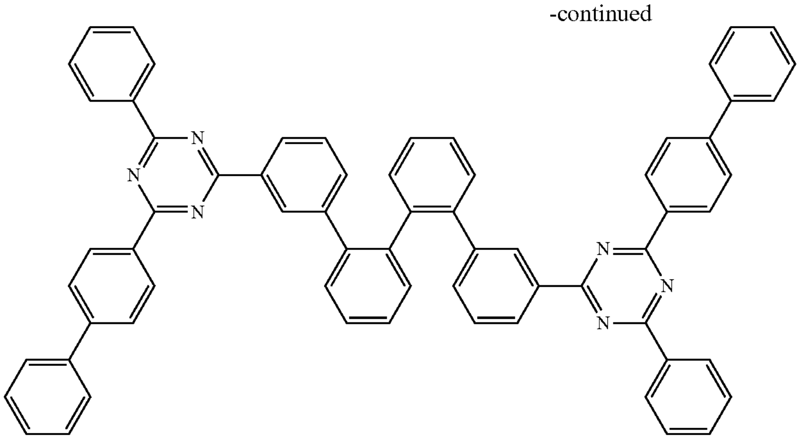
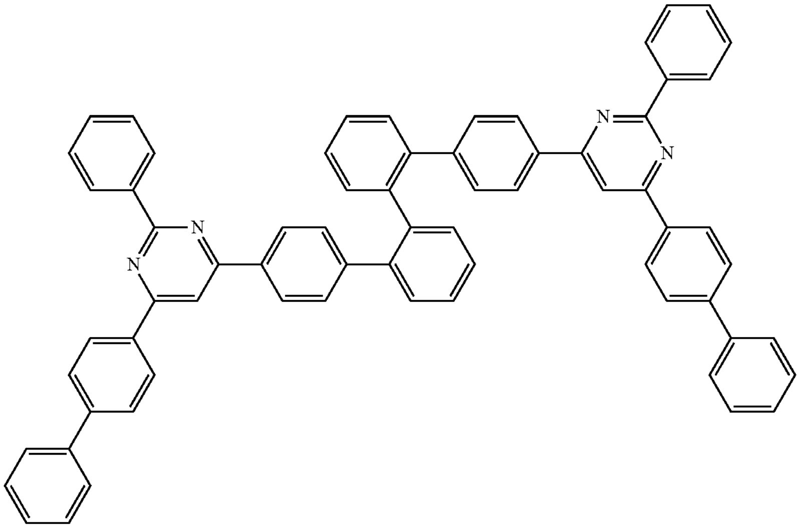
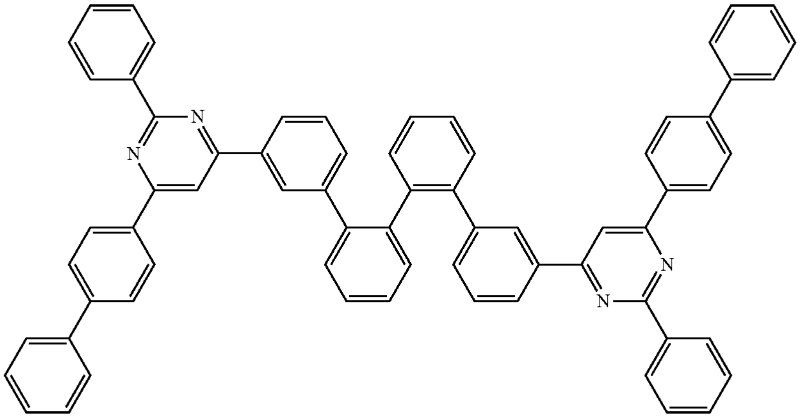

-continued
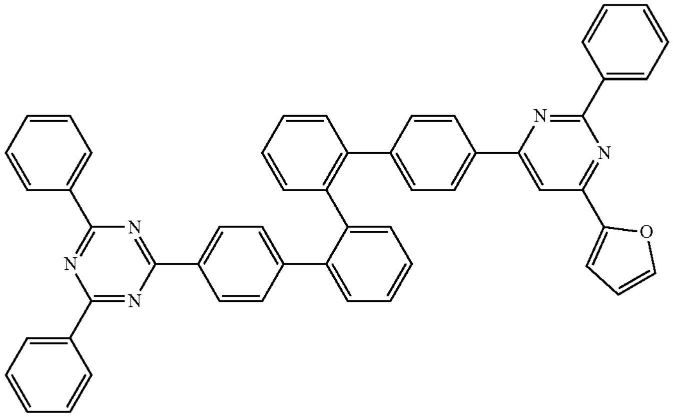
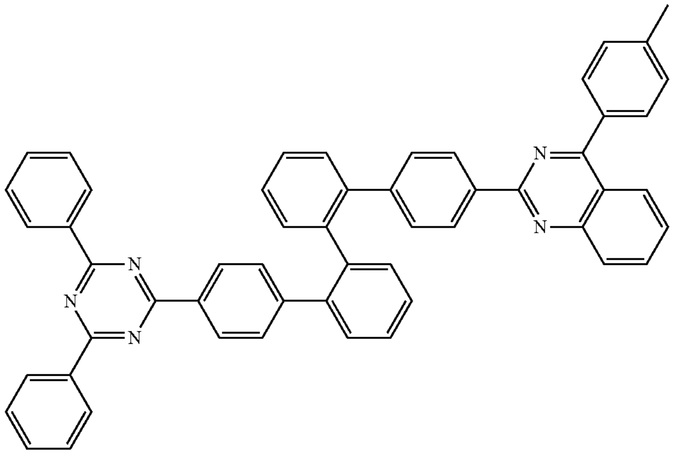
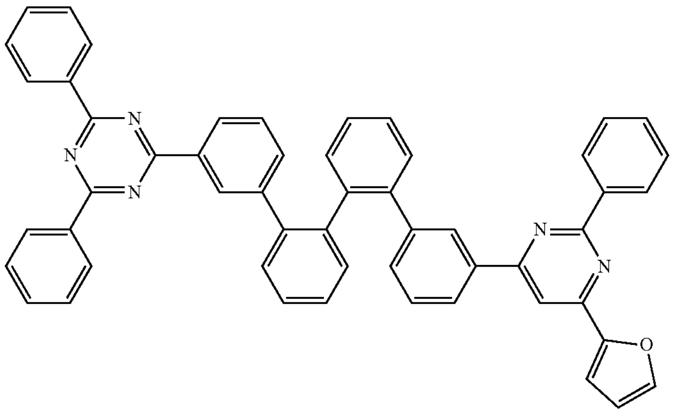

-continued
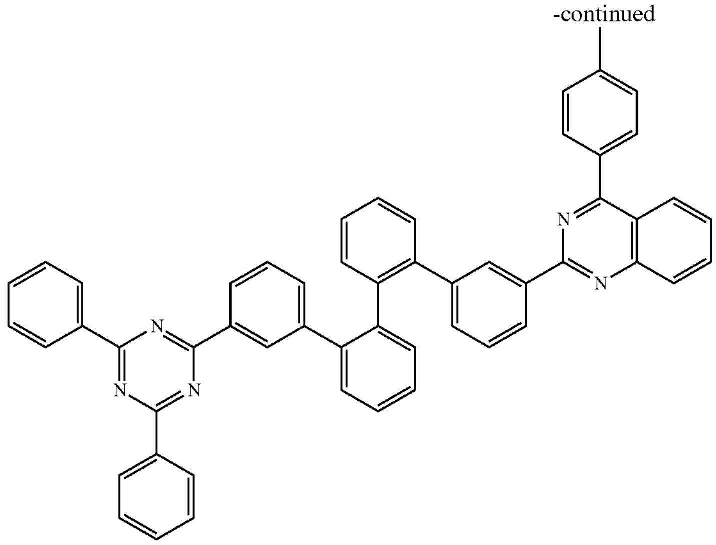
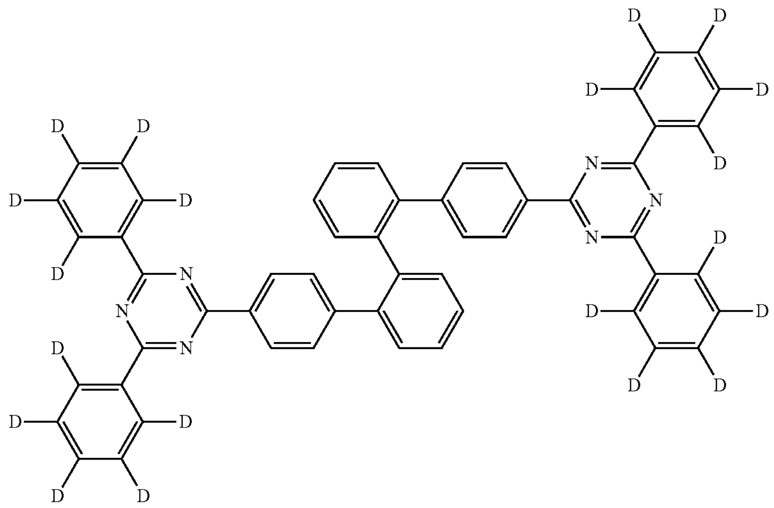
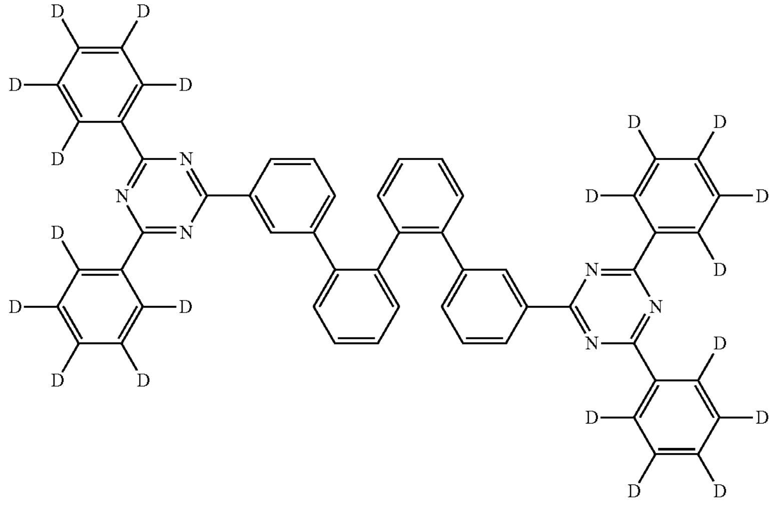

-continued

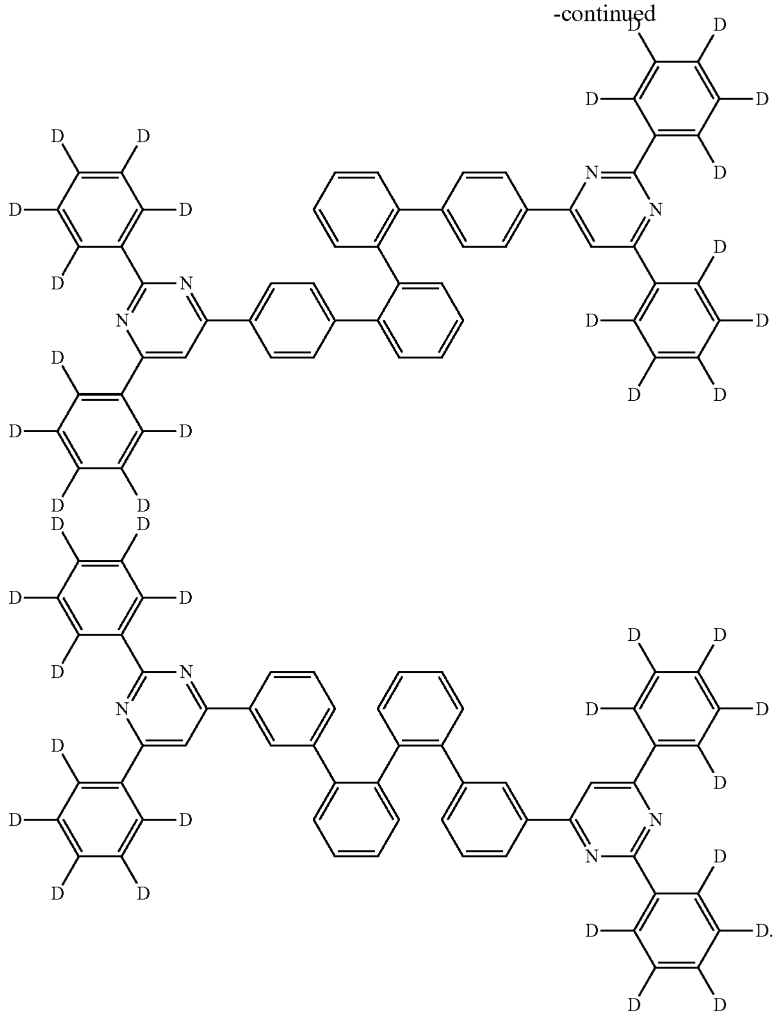

8. An organic light emitting device comprising:

a first electrode;

a second electrode that is opposite to the first electrode; and one or more organic material layers that are between the first electrode and the second electrode, wherein at least one layer of the one or more organic material layers comprises the compound according to claim 1.

9. The organic light emitting device of claim 8, wherein the organic material layer is an electron transport layer, an electron injection layer, or an electron transport and injection layer.

10. The organic light emitting device of claim 9, wherein the electron transport layer, the electron injection layer, or the electron transport and injection layer further comprises a compound of Chemical Formula 4:

[Chemical Formula 4]

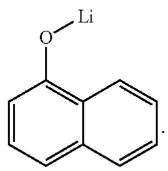

.

* * * * *